(12) United States Patent
Strano et al.

(10) Patent No.: US 11,155,509 B2
(45) Date of Patent: Oct. 26, 2021

(54) MATERIALS EXHIBITING BIOMIMETIC CARBON FIXATION AND SELF-REPAIR

(71) Applicant: MASSACHUSETTS INSTITUTE OF TECHNOLOGY, Cambridge, MA (US)

(72) Inventors: Michael S. Strano, Lexington, MA (US); Seonyeong Kwak, Cambridge, MA (US); Dorsa Parviz, Cambridge, MA (US); Daniel James Lundberg, Cambridge, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 162 days.

(21) Appl. No.: 16/591,596

(22) Filed: Oct. 2, 2019

(65) Prior Publication Data

US 2020/0102260 A1 Apr. 2, 2020

Related U.S. Application Data

(60) Provisional application No. 62/740,376, filed on Oct. 2, 2018.

(51) Int. Cl.
| | |
|---|---|
| *C08J 7/12* | (2006.01) |
| *C07C 45/00* | (2006.01) |
| *C12P 7/24* | (2006.01) |
| *C08G 65/16* | (2006.01) |
| *C07C 273/18* | (2006.01) |

(52) U.S. Cl.
CPC ........ *C07C 45/00* (2013.01); *C07C 273/1809* (2013.01); *C08G 65/16* (2013.01); *C08J 7/123* (2013.01); *C12P 7/24* (2013.01); *C08J 2300/00* (2013.01)

(58) Field of Classification Search
CPC ... C07C 45/00; C07C 273/1809; C08G 65/16; C08J 7/123; C12P 7/24
See application file for complete search history.

(56) References Cited

U.S. PATENT DOCUMENTS

2019/0136272 A1* 5/2019 Otte ........................ C12N 9/004

* cited by examiner

*Primary Examiner* — Edward J Cain
(74) *Attorney, Agent, or Firm* — Honigman LLP

(57) ABSTRACT

A composition can photocatalytically reduce carbon dioxide.

9 Claims, 55 Drawing Sheets

A

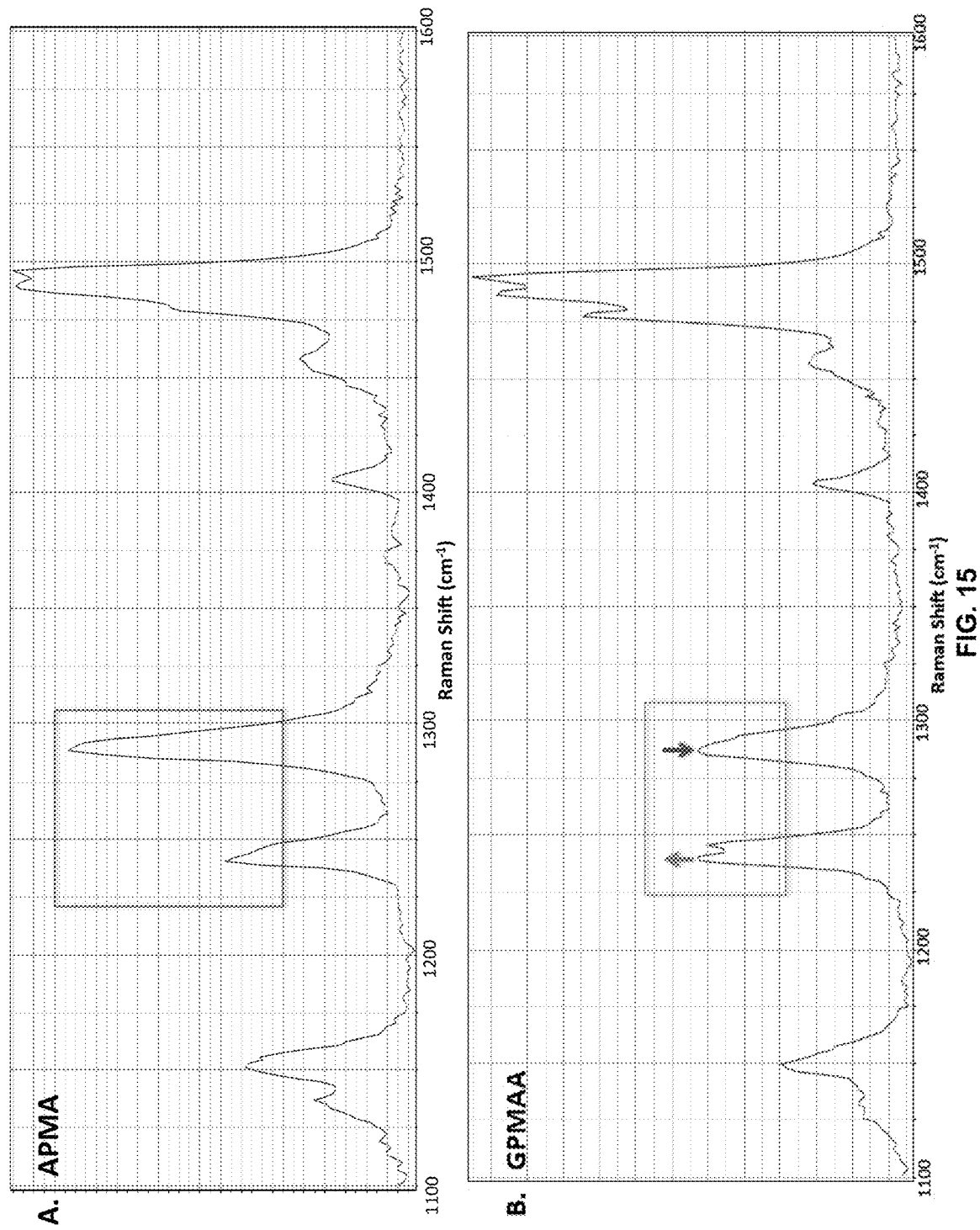

Table 2. Rate constants of reactions involved in RXN1, RXN2, and RXN3 estimated by fitting kinetic models to experimental data obtained from literature.

| $K_1$ (1/s) | $K_2$ (1/s) | $K_3$ (1/s) | $K_4$ (1/s) | $K_5$ (1/s) | $K_6$ (1/s) | $K_7$ (1/s) | $K_{r7}$ (1/s) | $K_8$ (1/s M) | $K_{r8}$ (1/s) | $K_9$ (1/s M) | $K_{r9}$ (1/s) | $K_{r10}$ (1/s) | $K_{r11}$ (1/s M²) |
|---|---|---|---|---|---|---|---|---|---|---|---|---|---|
| 9.72 e-7 | 4.86 e-8 | 3.78 e-5 | 2.48 e-5 | 2.66 e-4 | 1.10 e-4 | 1.50 | 8.39 e-3 | 3.35 e-2 | 2.03 e-3 | 6.58 e-2 | 1.05 e-2 | 7.68 e-7 | 9.97 e-7 | 2.85 e-3 | ern
MATERIALS EXHIBITING BIOMIMETIC CARBON FIXATION AND SELF-REPAIR

CLAIM OF PRIORITY

This application claims priority to U.S. Provisional Patent No. 62/740,376, filed Oct. 2, 2018, which is incorporated by reference in its entirety.

GOVERNMENT SPONSORSHIP STATEMENT

This invention was made with Government support under Grant No. DE-FG02-08ER46488 awarded by the Department of Energy (DOE). The Government has certain rights in the invention.

FIELD OF THE INVENTION

The invention relates to materials capable of carbon dioxide fixation.

BACKGROUND

Carbon dioxide is the main source for production of many chemicals including methanol and methane. Strategies for $CO_2$ reduction yield various products with different yield and selectivity. However, these approaches share the high energy consumption rates, using valuable reactants such as $H_2$, and possibly emitting more net $CO_2$ to atmosphere.

SUMMARY

In one aspect, a method of sequestering carbon dioxide can include exposing a composition including a catalyst to carbon dioxide, and reducing the carbon dioxide with the catalyst with light energy, chemical energy or electrical energy to form formaldehyde or a formaldehyde product.

In another aspect, a method of self-healing a polymer matrix can include exposing a polymer matrix including a catalyst to carbon dioxide and an energy source and generating additional material to the polymer matrix from the carbon dioxide.

In another aspect, a composition can include a polymer matrix including a catalyst configured to generate additional material to the polymer matrix from carbon dioxide with light energy, chemical energy or electrical energy to form formaldehyde or a formaldehyde product.

In certain circumstances, the catalyst can include a chloroplast, a nanocatalyst, or a colloidal battery. For example, the composition can include a chloroplast in a hydrogel.

In certain circumstances, the composition can include a nanoparticle, for example, particles can have a size of 2 nm to 500 nm. The nanoparticle can include a metal oxide or metal sulfide, for example, titania or ceria.

In certain circumstances, the composition can include a polymer matrix.

In certain circumstances, the composition can include an enzyme. For example, the composition can include a glucosidase, a glucose dehydrogenase or a hexokinase.

In certain circumstances, the composition can include a substrate. For example, the substrate can be a graphene oxide.

In certain circumstances, the composition can include a monomer. For example, the monomer can include a styrene, an acrylate or an acrylamide.

In certain circumstances, the formaldehyde product can include a urea formaldehyde polymer, a trimethylene oxide, or polyoxymethylene.

Other aspects, embodiments, and features will be apparent from the following description, the drawings, and the claims.

BRIEF DESCRIPTION OF DRAWINGS

In FIG. 1A, GPMAA forms hydrogel as lightly cross-linked by hydrogen bonding in water. The hydrogel continuously grows, strengthens and self-repairs as long as chloroplasts carry out carbon fixation and export glucose. In FIG. 1B, chloroplasts transform solar energy and carbon dioxide into the chemical energy and the assimilated carbon in the form of triose phosphate during the day. Alternatively, chloroplasts export maltose and glucose resulting from the breakdown of starch through the translocators at night. Exported glucose and glucose from enzymatic hydrolysis of maltose are converted to gluconolactone (GL) by GOx, and subsequently react to primary amine functionalized methacrylamide (APMA) and polymerize to glucose-containing polymethacryamide (GPMAA) in the medium.

FIG. 2A shows FT-IR spectra of the mixture of GL and APMA at 0 h, GPMAA and GO-GPMAA in 5 h under the light. FIG. 2B shows rheology properties of GPMAA (squares) and graphene oxide (GO) containing GPMAA (triangles) at different reaction time. The data are expressed as the average±SD (n=3). FIG. 2C shows a schematic illustration on separation of GPMAA hydrogel. FIG. 2D shows formation of fibrillar structure during the separation process. Two separated thin GPMAA hydrogels are formed on the glass slides and then they are attached to each other. The glass slides are pulled separating the hydrogels at a rate of 0.04 mm/sec.

FIG. 3A shows glucose concentration with and without maltose hydrolysis by a-glucosidase (24 U mL−1) at light and dark period. Total incubation time is 8 h with 4 h of light and 4 h of dark. FIG. 3B shows glucose concentration in different illumination time; 12 h light and 12 h dark (black squares), continuous illumination for 24 h (blue circles), and 12 h light and 12 h dark with 5 mM Pi supply at the beginning of dark period (pink triangles). FIG. 3C shows an effect of chloroplast proton gradient or ATP on glucose export. Chloroplast medium is adjusted from optimum pH 7.6 (control, black squares) to pH 8.0 (pink triangles) to induce alkalinization of chloroplast stroma, and 2 mM ATP is added to the medium (blue circles) to enhance active transport mechanism of glucose. FIG. 3D shows a comparison of approaches to boost glucose export under presence or absence of external Pi supply. A mixture of hexokinase (10 U mL−1), 0.6 mM ATP, with 5 mM Pi (blue circles) or without additional Pi (pink triangles), or 5 mM Pi alone (black squares) is added to the chloroplast suspension medium at every hour during the dark period. Black arrows indicate the addition of 5 mM Pi. FIG. 3E shows an effect of nanoceria on glucose export after 12 h light period. Chloroplasts are incubated in presence of nanoceria 3 h prior to the light period. Final concentration of nanoceria is 5 μM (blue circles) or 50 μM (pink triangles). Control means chloroplast incubated for the experimental period without nanoceria (black squares). Green arrows indicate the addition of hexokinase reaction mixture. White or black rectangles on the top of each graph imply light or dark period, respectively. FIG. 3F shows GL concentration from chloroplasts incubated in the medium containing 20 U mL−1 GOx under the continuous illumination for 5 h. White or black rectangles on the top of each graph imply light or dark period, respectively. GL concentration is presented by gluconic acid after hydrolysis in 2M NaOH. The data are expressed as the average±S.D. (n=5-10). *P, **P<0.05 compared with control [Glucose] at 0 h.

FIG. 4A shows a microscope images of growing hydrogel near the isolated chloroplasts in the medium containing GOx (20 U mL−1) and 0.1% w/v APMA. Exposure conditions are ambient $CO_2$ and 18 h ambient illumination after 1 h dark period. Scale bars are 5 μm. FIG. 4B shows a schematic illustration of hydrogel formation on the graphene oxide film. Isolated chloroplasts are incubated with GOx immobilized graphene oxide film in the medium containing 0.1% APMA. Followed by glucose export from chloroplasts, glucose is converted into GL on the graphene oxide surface by GOx followed by reacting to APMA, which polymerizes to form GPMAA. FIG. 4C shows a characteristic Raman bands of GPMAA hydrogel. FIG. 4D shows an optical image of chloroplast embedded-GPMAA hydrogel (left) and Raman mapping (right) based on the characteristic Raman bands ratio between 1245 and 1290 $cm^{-1}$ under a laser excitation of 632 nm. Scale bars are 2 μm.

FIG. 5A shows partially repaired hydrogels by exposure to light overnight, hydrogels are dyed yellow and blue to allow for easily distinguished interface. FIG. 5B shows fully repaired hydrogels by addition of 1 M GL (5 μL) to the interface and exposure to light overnight. FIG. 5C shows shear strength restoration of hydrogels by physical attachment for 30 min (blue line) or exposure to light overnight after addition of GL (red line). Two separated thin GPMAA hydrogels are formed on the glass slides and then they are attached to each other. The glass slides are pulled separating the hydrogels at a rate of 0.04 mm/sec. FIG. 5D shows a schematic illustration of self-healing mechanism of chloroplast embedded hydrogel matrix. Glucose molecules supplied by chloroplasts repair the local damage by exceeding its own local material balance through the atmospheric $CO_2$ fixation.

FIGS. 8A-C show different time intervals, (FIG. 8A) 2 h, (FIG. 8B) 6 h, and (FIG. 8C) 18 h. Frequency sweep on GPMAA hydrogel shows a more solid-like behavior (G'>G"). FIG. 8D shows corresponding recovery of GPMAA hydrogel under shear stress (strain 100%, black) and after removal of shear stress (strain 1% black).

FIGS. 9A-9C show different time intervals, (FIG. 9A) 2 h, (FIG. 9B) 6 h, and (FIG. 9C) 18 h. Frequency sweep on GPMAA hydrogel shows a more solid-like behavior (G'>G"). FIG. 9D shows corresponding recovery of GPMAA hydrogel under shear stress (strain 100%, black) and after removal of shear stress (strain 1% black).

FIG. 10A shows a representative indentation curve for the swollen GPMAA gel with 50 wt % water content. FIG. 10B shows a representative indentation curve for the dry GPMAA. FIG. 10C shows Young's moduli measured with both sharp and colloidal probes (n=5). It is known that sharp probes result in small overestimation because the contact surface area is difficult to be precisely determined.

FIG. 11A shows a schematic layout showing a microfluidic chip with a chamber for chloroplasts (green ellipsoids) and microsieves to extract produced glucose (small red spheroids). FIG. 11B shows a photo of the microfluidic chip. Scale bar is 1 cm. FIG. 11C shows glucose concentration with or without nanoceria.

FIG. 15 depicts a comparison of Raman spectra between APMA and GPMAA.

DETAILED DESCRIPTION

Figure 1A:
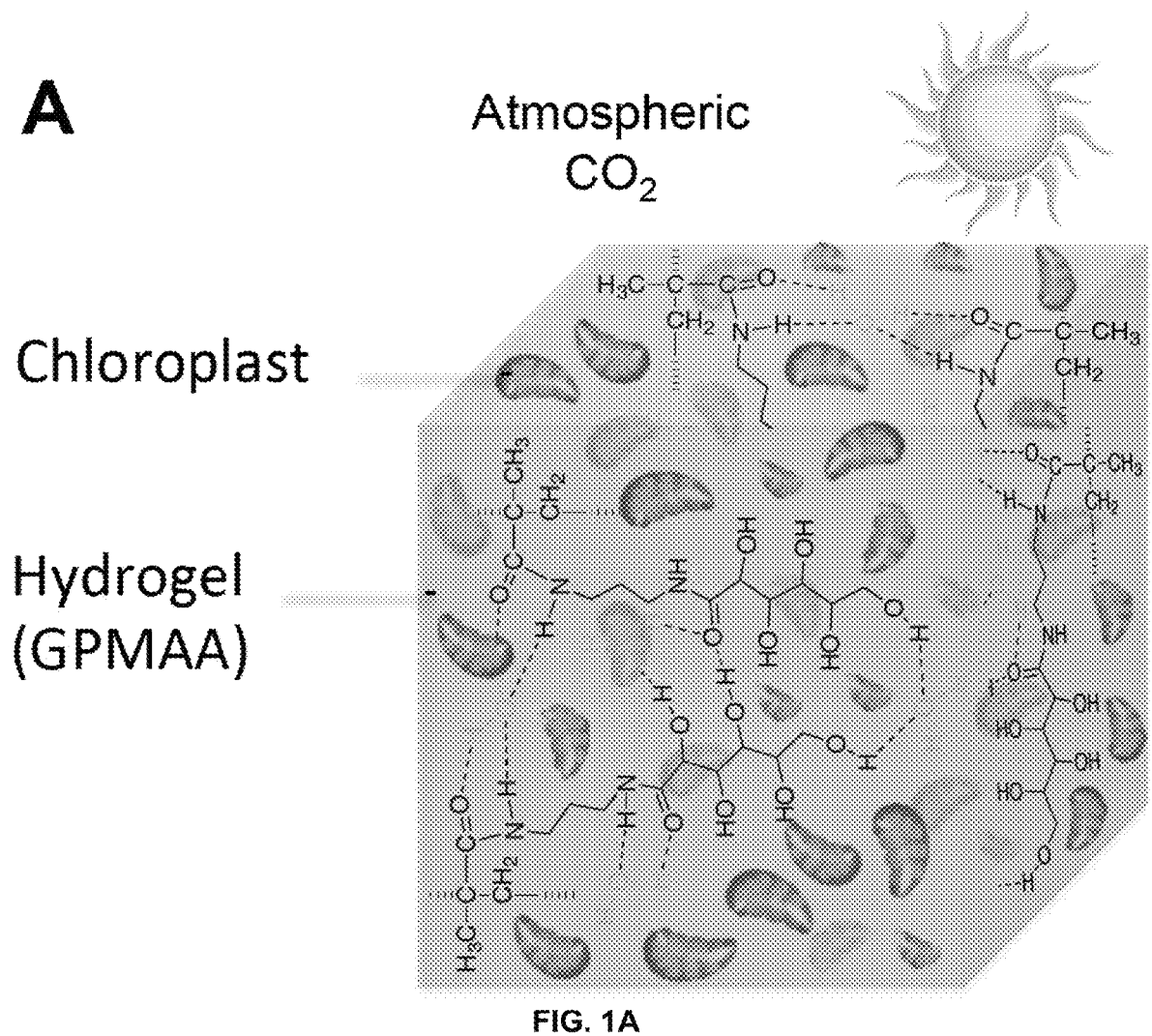
FIGS. 1A-1B depict a schematic illustration of a synthetic material that grows, strengthens and self-repairs with embedded plant chloroplasts.

In one example, one can learn from the mechanisms of self-assembly and self-repair displayed particularly in living plant systems to create human-synthesized analogs that benefit from these higher functions operating under non-biological conditions. Here, recent efforts in engineering biomimetic systems that exploit ambient solar energy harvesting and carbon dioxide conversion to high-energy products such as glucose and its polymeric derivatives are highlighted. By performing these reactions compartmentally, it is possible to create materials that grow and self-repair using carbon dioxide as a carbon source. Such materials would significantly benefit transportation and construct costs, as well as exhibit self-healing and densification over time. Two systems are detailed below.

The first involves the extraction of functional plant chloroplasts from biomass and using them as embedded, functional photocatalysts for the production of glucose and starches from ambient solar energy and atmospheric carbon dioxide. Glucose can be converted to gluconolactone (GL) by glucose oxidase (GOx), which can then readily react with nucleophiles, such as the primary amine group ($—NH_3$) to generate a growing polymer matrix. The importance of inorganic phosphate (Pi) concentration, glucose equilibrium across the chloroplast membrane, and the concentration of photo-generated reactive oxygen species (ROS) towards glucose export efficiency have been investigated. Glucose export from the isolated chloroplasts to gain quantifiable molecules for building of a self-growing material was enhanced. Isolated chloroplasts are placed on the GOx immobilized-graphene oxide film in buffer containing co-monomer, 6-aminopropyl methacrylamide (APMA). In the presence of ambient light and exposure to atmospheric carbon dioxide for 18 hours at room temperature, the formation of hydrogel-like material was observed around the chloroplast membrane as confirmed by Raman spectroscopy 3D mapping. These efforts have benefited from a new technique, Lipid Exchange Envelope Penetration (LEEP) developed at MIT for the incorporation of nanoparticles into living plants, protoplasts and chloroplasts in vivo. This method allows for the incorporation of chemo-protective, stabilizing and photoactive nanoparticles into the chloroplast to preserve and extend its catalytic function.

In one aspect, a method of sequestering carbon dioxide can include exposing a composition including a catalyst to carbon dioxide, and reducing the carbon dioxide with the catalyst with light energy, chemical energy or electrical energy to form formaldehyde or a formaldehyde product.

In another aspect, a method of self-healing a polymer matrix can include exposing a polymer matrix including a catalyst to carbon dioxide and an energy source and generating additional material to the polymer matrix from the carbon dioxide.

In another aspect, a composition can include a polymer matrix including a catalyst configured to generate additional material to the polymer matrix from carbon dioxide with light energy, chemical energy or electrical energy to form formaldehyde or a formaldehyde product.

The enzymes or other additives can remove photo-generated reactive oxygen species inside chloroplasts can extend the lifetime of isolated chloroplasts, which ultimately translates into higher glucose accumulation in the medium. In another example, glucose export increases only after the addition of hexokinase, which acts as a sink for this flux outside of the chloroplast.

Embedded, extracted chloroplasts can be carbon-fixing photocatalysts, which utilize abundant atmospheric carbon dioxide and solar energy to produce reduction products. The material that can autonomously grow, strengthen and repair itself in response to certain types of damage. For example, separated hydrogels are able to seamlessly recombine upon light exposure (FIGS. 5A-5D).

In certain circumstances, the catalyst can include a chloroplast, a nanocatalyst, or a colloidal battery. For example, the composition can include a chloroplast in a hydrogel.

In certain circumstances, the composition can include a nanoparticle, for example, particles can have a size of 2 nm to 500 nm. The nanoparticle can include a metal oxide or metal sulfide, for example, titania or ceria.

In certain circumstances, the composition can include a polymer matrix.

In certain circumstances, the composition can include an enzyme. For example, the composition can include a glucosidase ($\alpha$-glucosidase), a glucose dehydrogenase or a hexokinase.

In certain circumstances, the composition can include a substrate. For example, the substrate can be a graphene oxide.

In certain circumstances, the composition can include a monomer. For example, the monomer can include a styrene, an acrylate or an acrylamide.

In certain circumstances, the formaldehyde product can include a urea formaldehyde polymer, a trimethylene oxide, or polyoxymethylene. The composition generates formaldehyde, thus, under reaction with urea, formaldehyde can produce Urea formaldehyde (UF), also known as ureamethanal.

As a next generation material system, the function of the chloroplast with a semiconducting photocatalyst such as $TiO_2$ or graphitic $C_3N_4$ for direct $CO_2$ reduction to formaldehyde was replaced. Domains performing this chemistry under ambient conditions can be coupled into a material with differing pH to generate 1,3,5-trioxane and polymerize to linear polyoxymethylene with a boron trifluoride ($BF_3$) or boron trifluoride diethyl etherate ($BF_3OEt_2$) as initiator. This system uses atmospheric $CO_2$ and converts it rapidly, avoiding the problem of intermediate storage of the carbon from $CO_2$ and the associated energy expenditure. The final product is a lightweight, portable polymeric structure that can react with atmospheric $CO_2$, densify, and self-repair in the presence of sunlight. Synthetic efforts going forward examine hierarchical integration and self-healing of both systems, coupled to a theoretical framework within which the design and function of these fundamentally new types of materials is explored. The mechanistic details of Systems I and II are described below.

System 1: Materials with Embedded, Functional Plant Chloroplasts as Photocatalysts for Glucose to Monomer to Polymer Matrix Production from Ambient Solar Energy and $CO_2$ Materials capable of dynamic self-repair are commonly found among living scaffolds and tissues. Correcting damage through self-repair mechanisms promise enhanced material lifetimes and increased resistance from fatigue and acute mechanical stress. There has been a concerted research effort to develop synthetic materials mimicking aspects this natural property by dynamic chemistry based on either covalent bonds or non-covalent interactions that form or break reversibly. However, an important distinction can be made here. These dynamic chemical approaches necessarily require one or more external stimuli such as heating, pH, mechanical stress, UV light, and external chemical treatment. Alternatively, autonomous systems, defined as materials that themselves can detect and respond to damage, have been recently introduced. An encapsulated-monomer approach was first reported by White and co-workers in 2001, in which reservoirs of a monomer and a polymerization initiator or catalyst are contained within the bulk of the material. A variant approach using bacteria (Bacillus sphaericus)-induced carbonate precipitation was utilized for micro-cracks healing on a concrete material, but bacteria action was limited due to lack of the local energy sources and low survivability in concrete. The energy source limitation may in-fact translate into a fundamental one for the use of heterotrophic living organisms in materials.

Figure 1B:
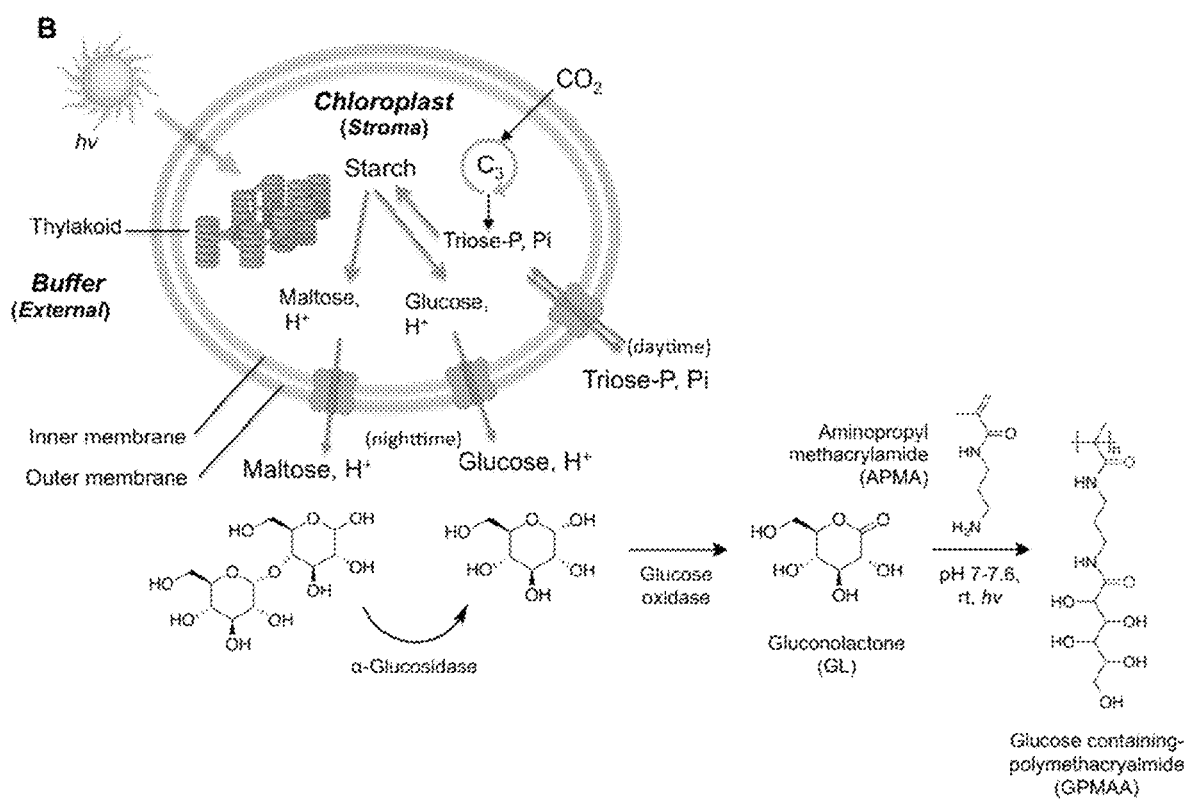

Herein, a new direction in self-healing materials as combining the autonomy of damage response with the ability to exceed the material's own local material balance has been identified. To this end, a novel class of material designed to grow, repair and strengthen through carbon fixation was created. By using embedded, extracted chloroplasts as carbon-fixing photocatalysts, utilize abundant atmospheric $CO_2$ and solar energy (FIGS. 1A-1B) as drivers. The chemistry of material synthesis to use glucose, a saccharide exported from chloroplasts, for facile reaction under relatively mild conditions was designed. Several strategies are systematically investigated to improve glucose export from isolated chloroplasts, shown to be the limiting factor in the growth and repair rate of the material. The exported glucose is converted to GL, which subsequently reacts with primary amine-functionalized acrylamide monomers, 3-aminopropyl methacrylamide (APMA), to build a polymer matrix. The chloroplast embedded-gel matrix, containing lightly crosslinked polymer networks that swell in water, continually grows, strengthens, and self-repairs using fixation of atmospheric $CO_2$ as a regeneration source under ambient illumination was demonstrated.

Hydrogel Composite Design and Synthesis

Figure 2A:
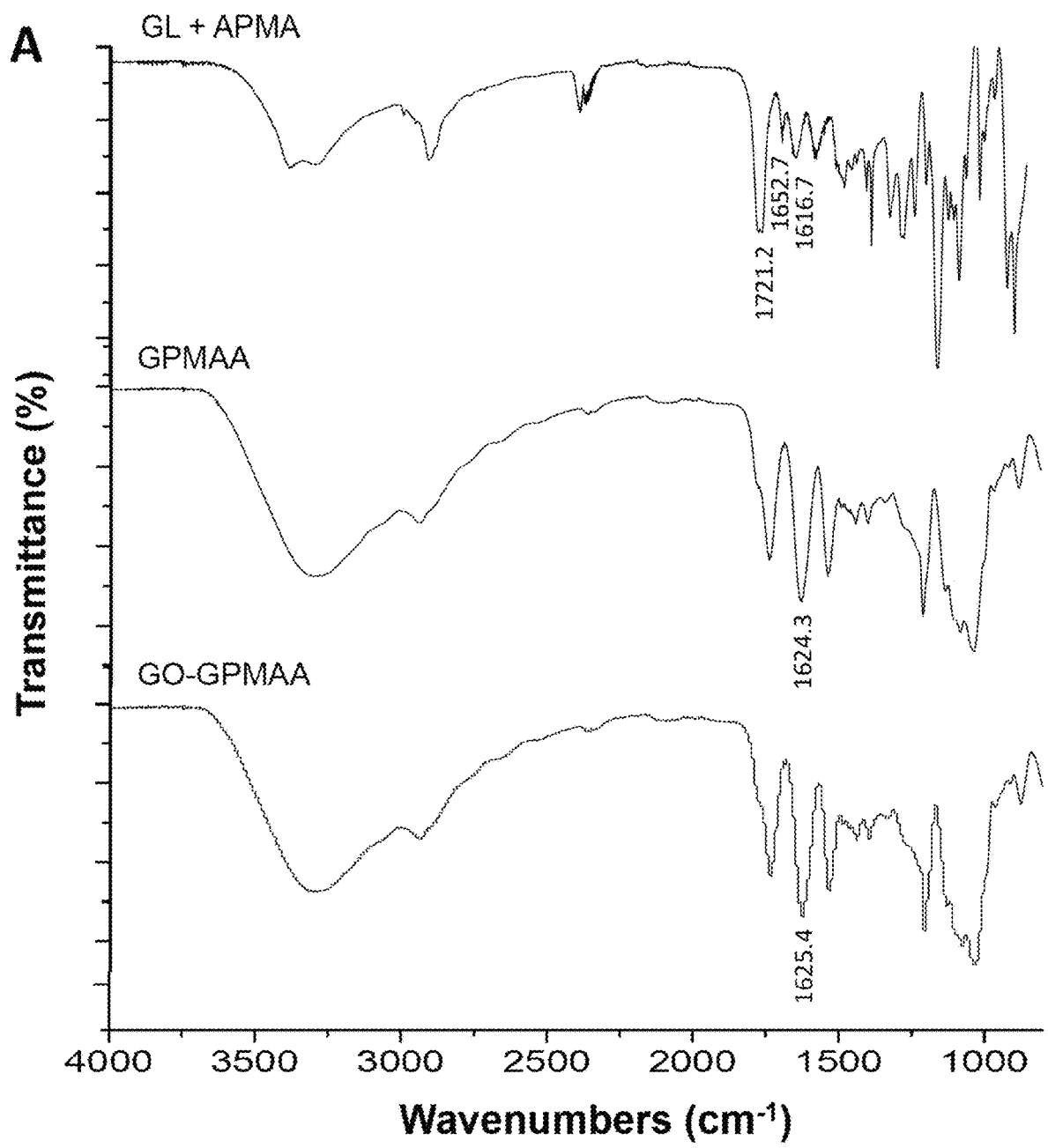
FIGS. 2A-2D depict in vitro a carbon fixing hydrogel formation from gluconolactone and 3-aminopropyl methacrylamide.
Figure 2B:
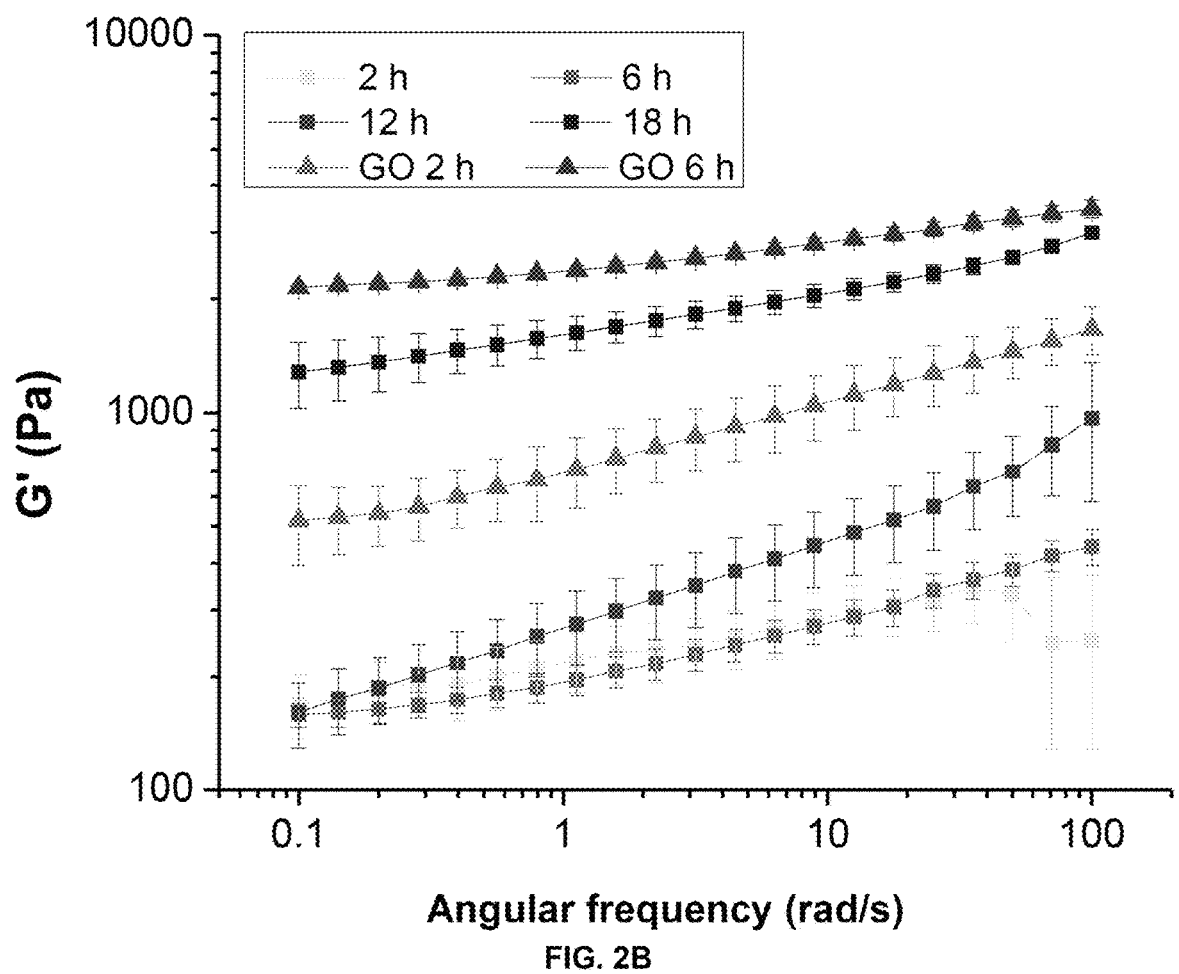
Figure 2C:
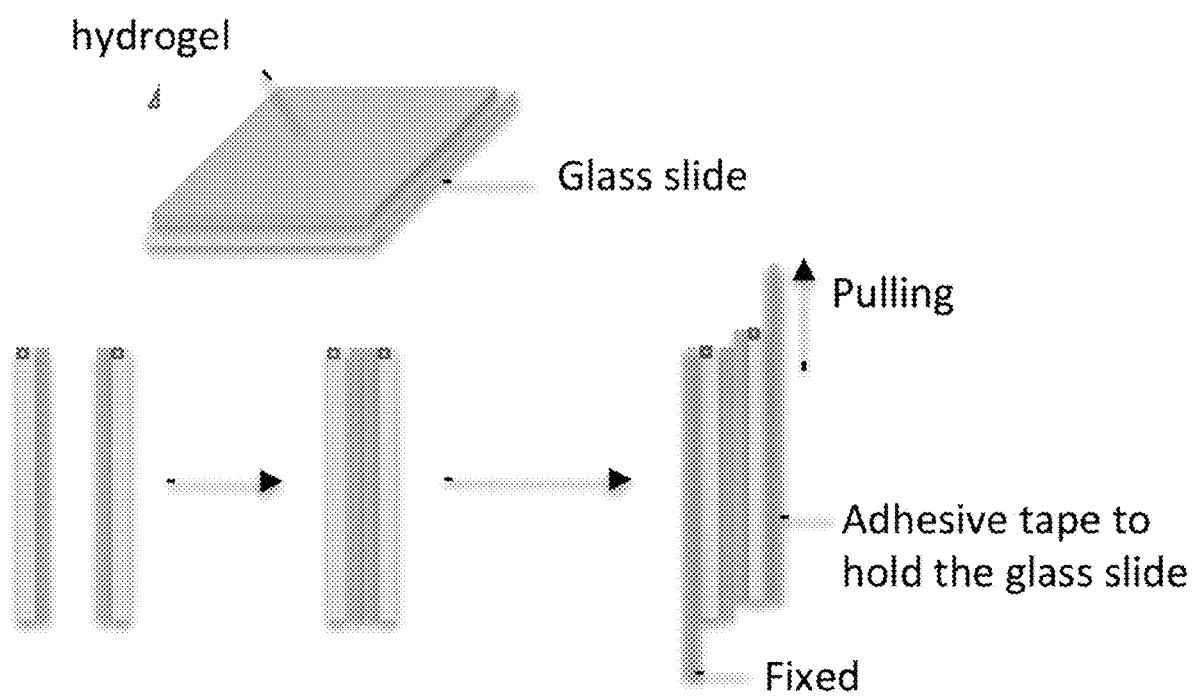
Figure 10A:
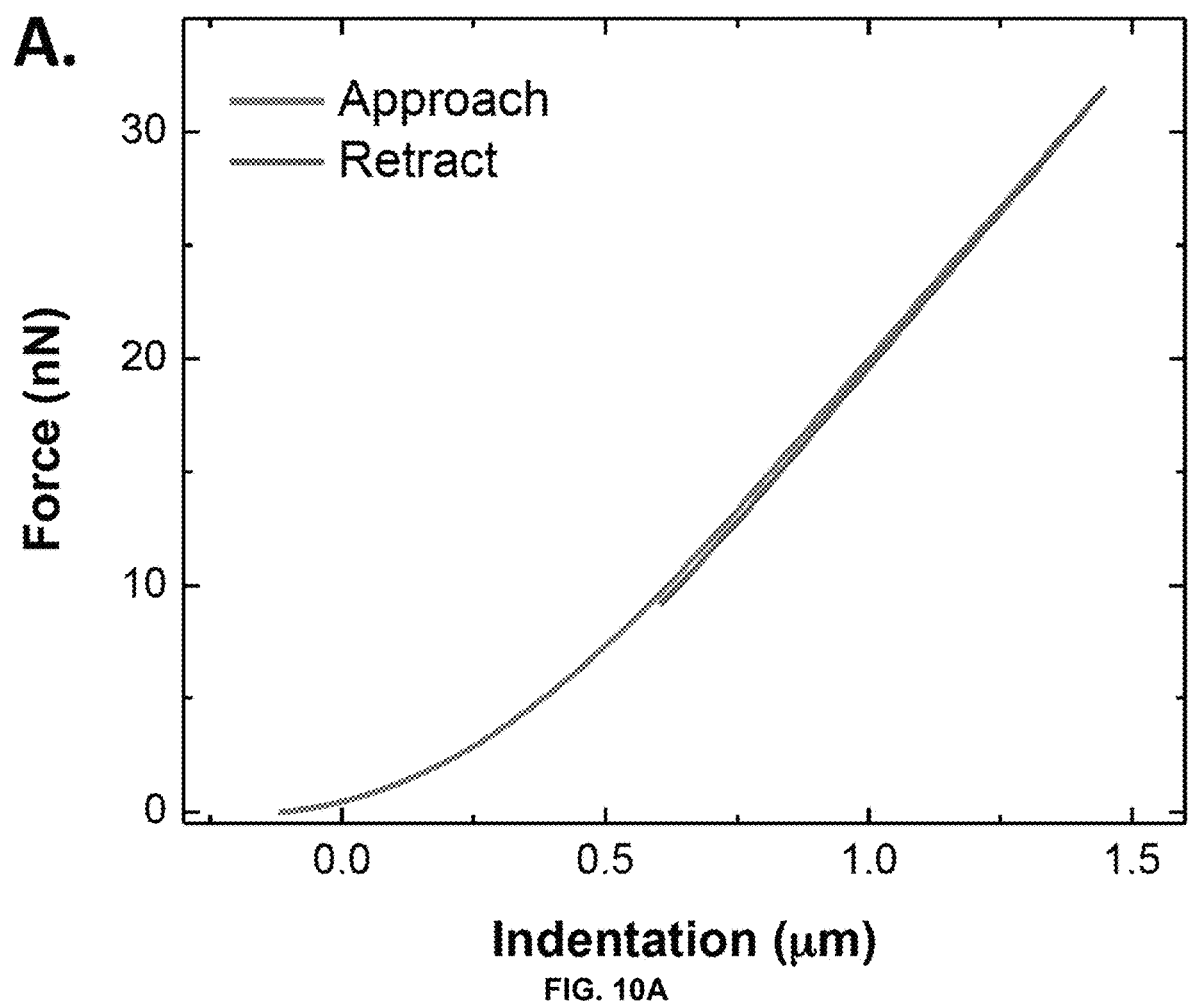
FIGS. 10A-10C depict indentation curves.
Figure 10B:
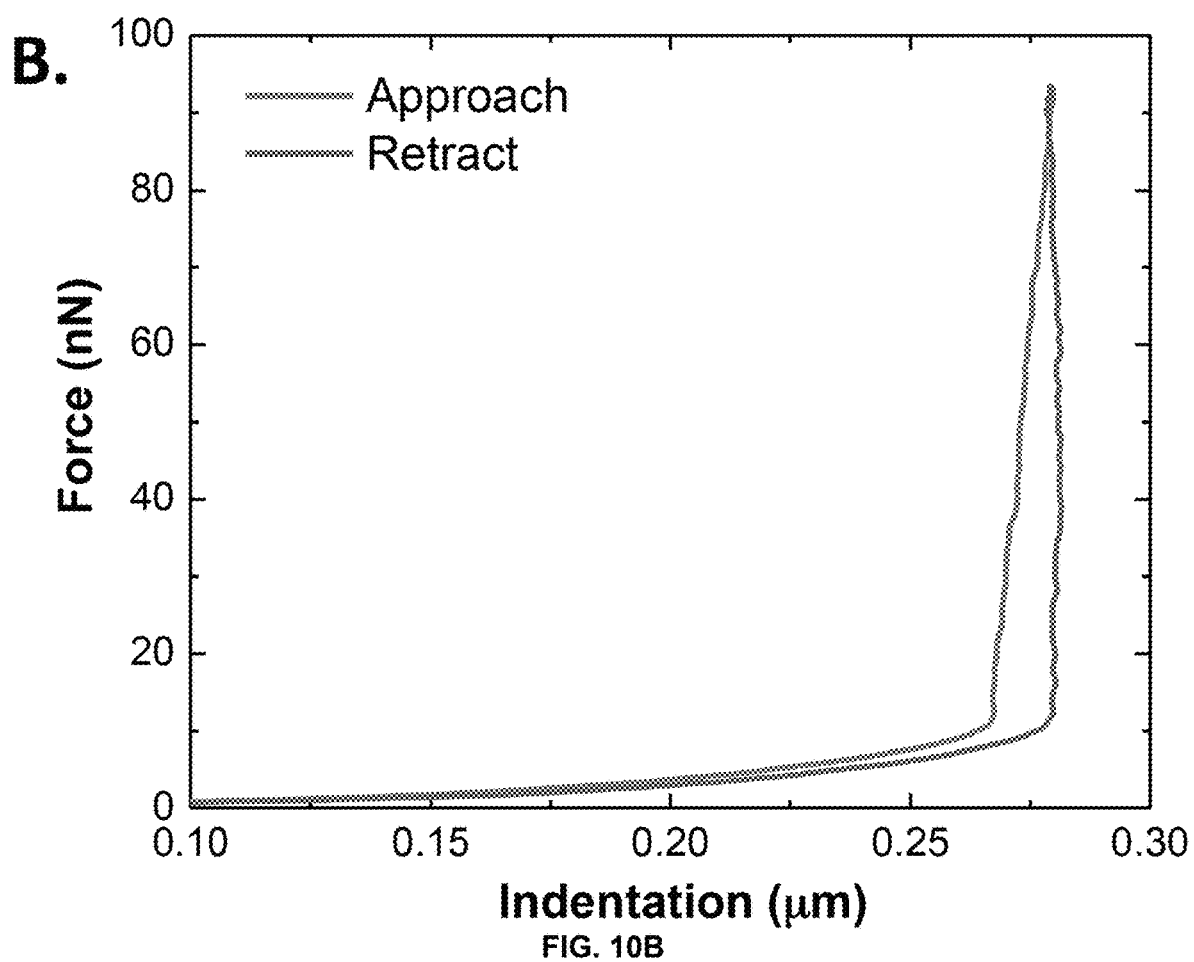
Figure 10C:
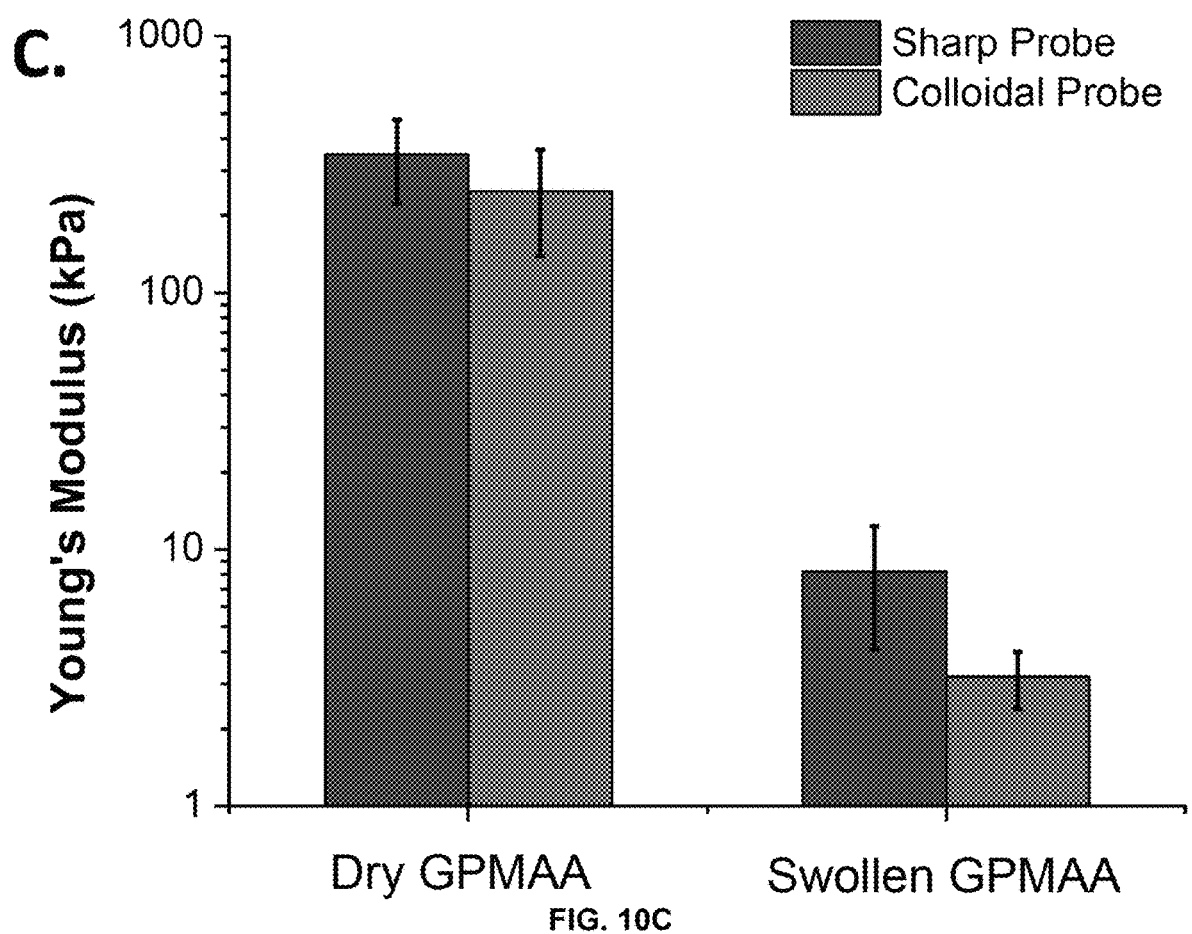

The three major saccharides exported from chloroplasts (extracted or in-vivo) are maltose, glucose and triose phosphate. Glucose as a reagent to focus on because it is easily converted into a reactive precursor, gluoconolactone (GL) were selected. One D-glucose molecule is oxidized to one D-gluocono-1,5-lactone molecule and one hydrogen peroxide ($H_2O_2$) molecule by glucose oxidase (GOx). These scheme has been used for glycopolymer synthesis previously. The product of the polymerization reaction of GL and aminopropyl methacrylamide (APMA) appears transparent and gel-like. The characteristic IR peaks, lactone C=O of GL appears at 1719.7 $cm^{-1}$ and acrylamide C=O of APMA appears at 1652.9 $cm^{-1}$ and 1616.7 $cm^{-1}$ in the mixture of GL and APMA at 0 h (FIGS. 2A, 6A-6F, and 7A-7B). The mixture of GL and APMA in pH 7.0 phosphate buffer is put under the ambient light for 5 h until hydrogel (denoted as GPMAA) forms, as indicated by the presence of a new broad peak at 1624.3 $cm^{-1}$ that corresponds to the formation of amide bond between GL and APMA as well as the polymerization of acrylamide (FIG. 2A). The rheological properties of the hydrogels show that the storage modulus G' at high angular frequency (100 rad $s^{-1}$) is 3 kPa and shear modulus measured at different reaction times implies that GPMAA synthesis in completed within 18 h (FIGS. 2B and 8). GPMAA shows a swelling property and exhibits a 115-fold increase hydrogel weight in 48 h due to water absorption. Using atomic force microscopy as an indenter, the Young's modulus of chloroplasts was estimated to be 26 ($\pm 5$) kPa, which is higher than that of the swollen GPMAA hydrogel (water 50 wt %) at 8.2 ($\pm 4.1$) kPa and lower than that of dry GPMAA at 348 ($\pm 125$) kPa (FIGS. 10A-10C). Thus, the chloroplasts can reinforce the GPMAA hydrogel in a liquid environment. In addition, graphene oxide at low weight fraction (0.01 wt %) can be used to immobilize glucose oxidase (GOx) on the surface of graphene oxide sheets, which also serve as mechanical inclusions for stiffening. Graphene oxide-containing hydrogel is formed within 6 h, which is 3 times faster than that of hydrogel formation without graphene oxide (FIG. 2C). After 6 h, the shear modulus of GPMAA hydrogel is 0.4 (+0.05) kPa while that of graphene oxide containing GPMAA hydrogel is 3.5

Figure 2D:
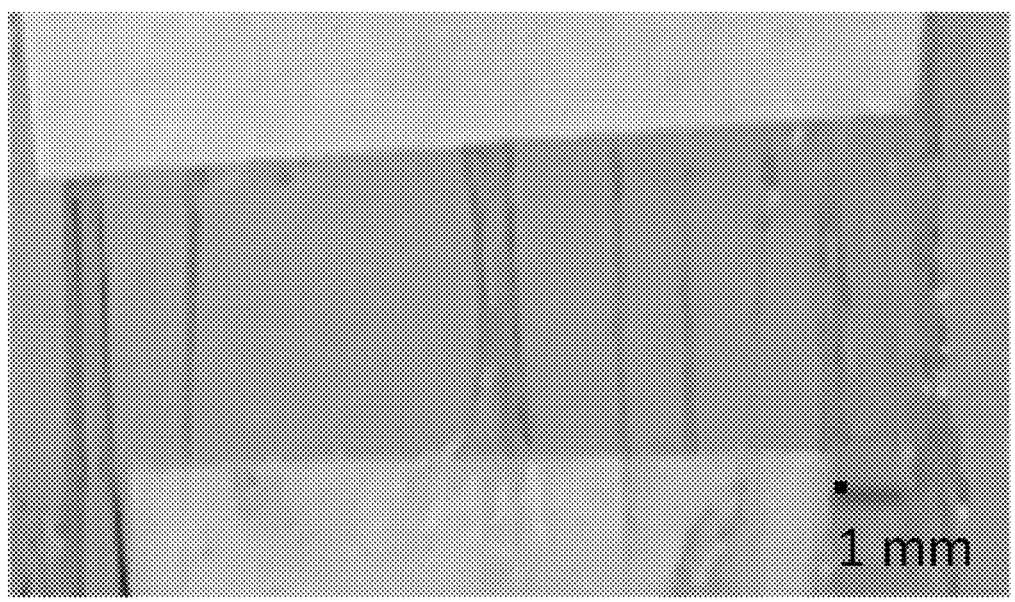
Figure 11A:
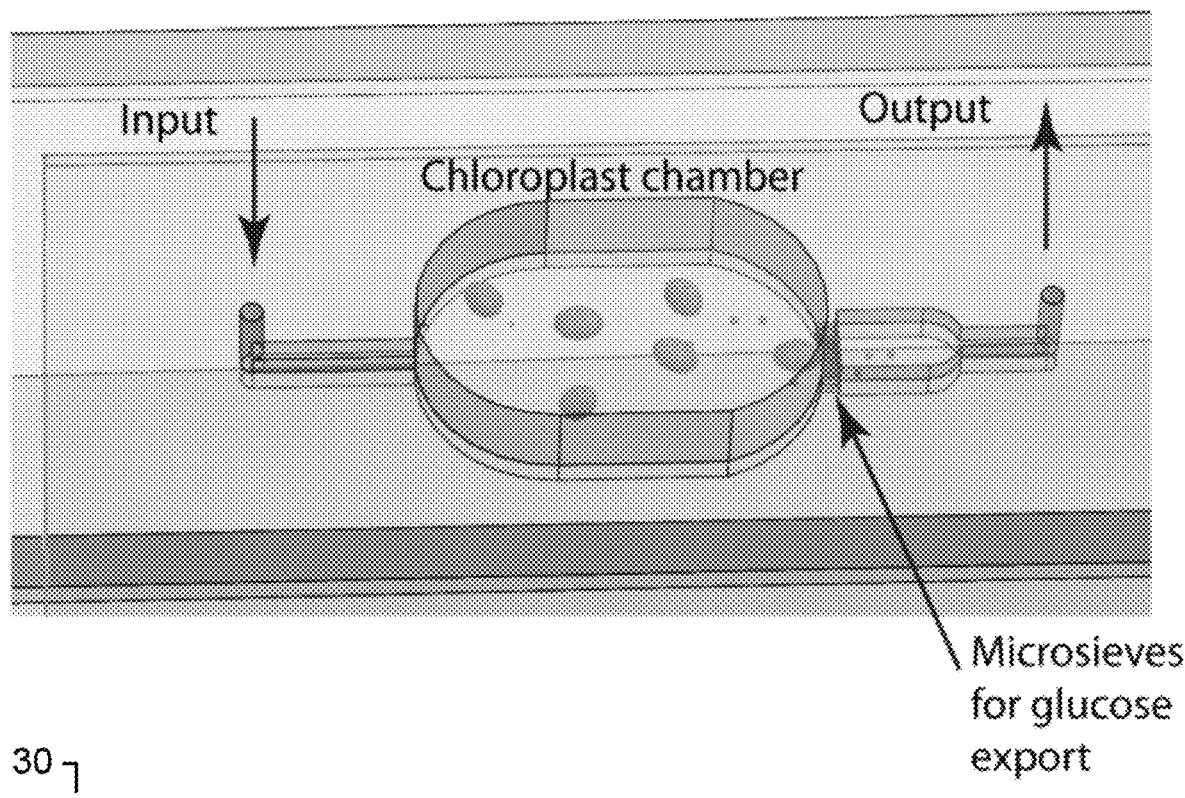
FIGS. 11A-11C depict measurement of glucose exported from isolated chloroplasts on the microfluidic chip.
Figure 11B:
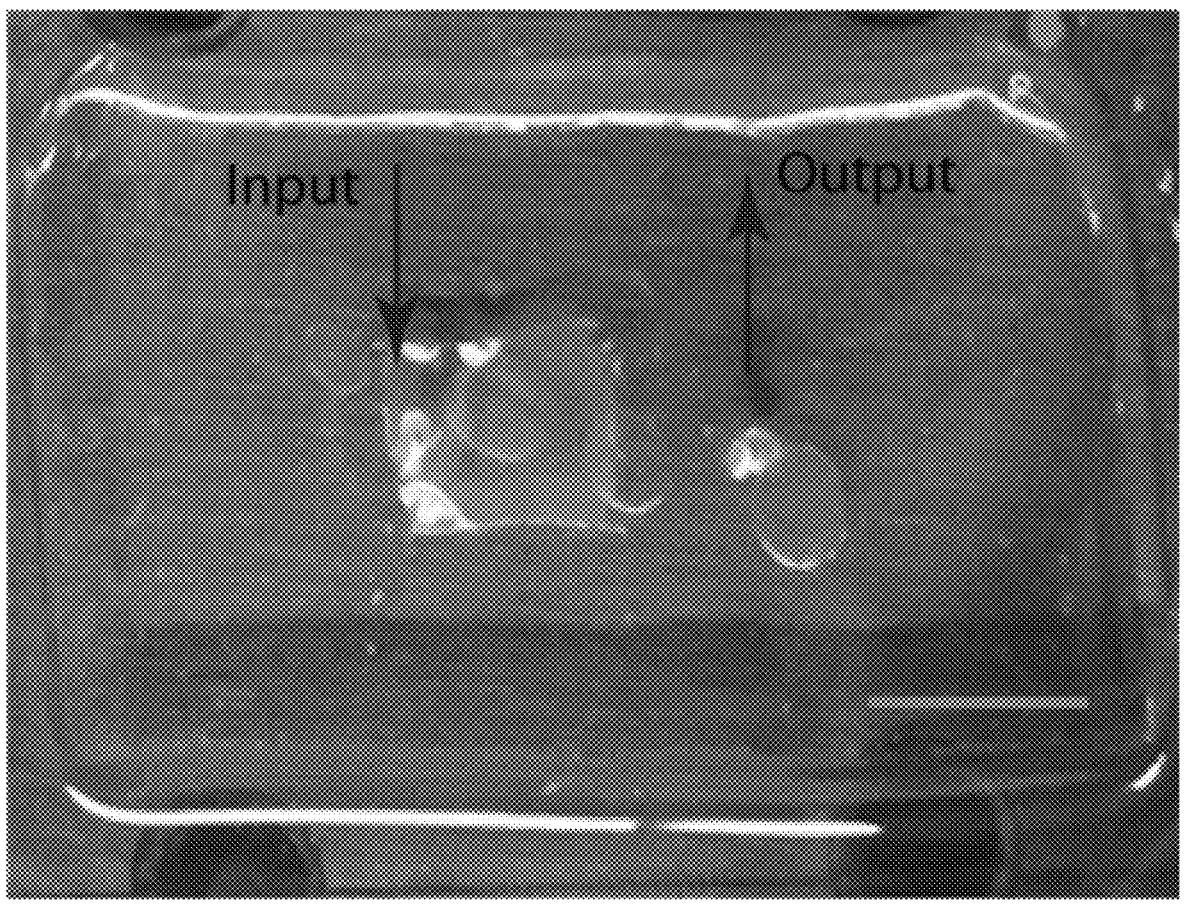
Figure 11C:
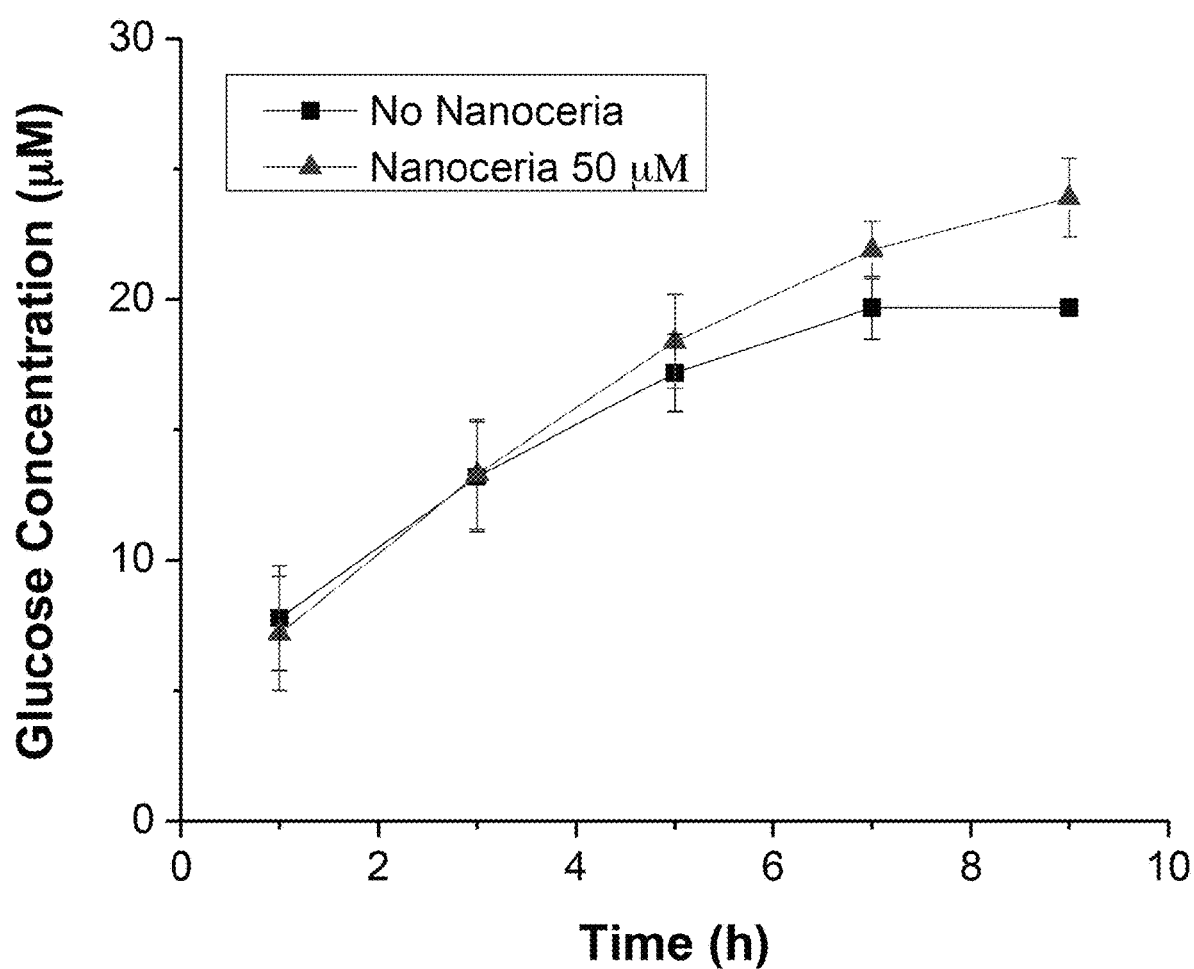
Figure 12:
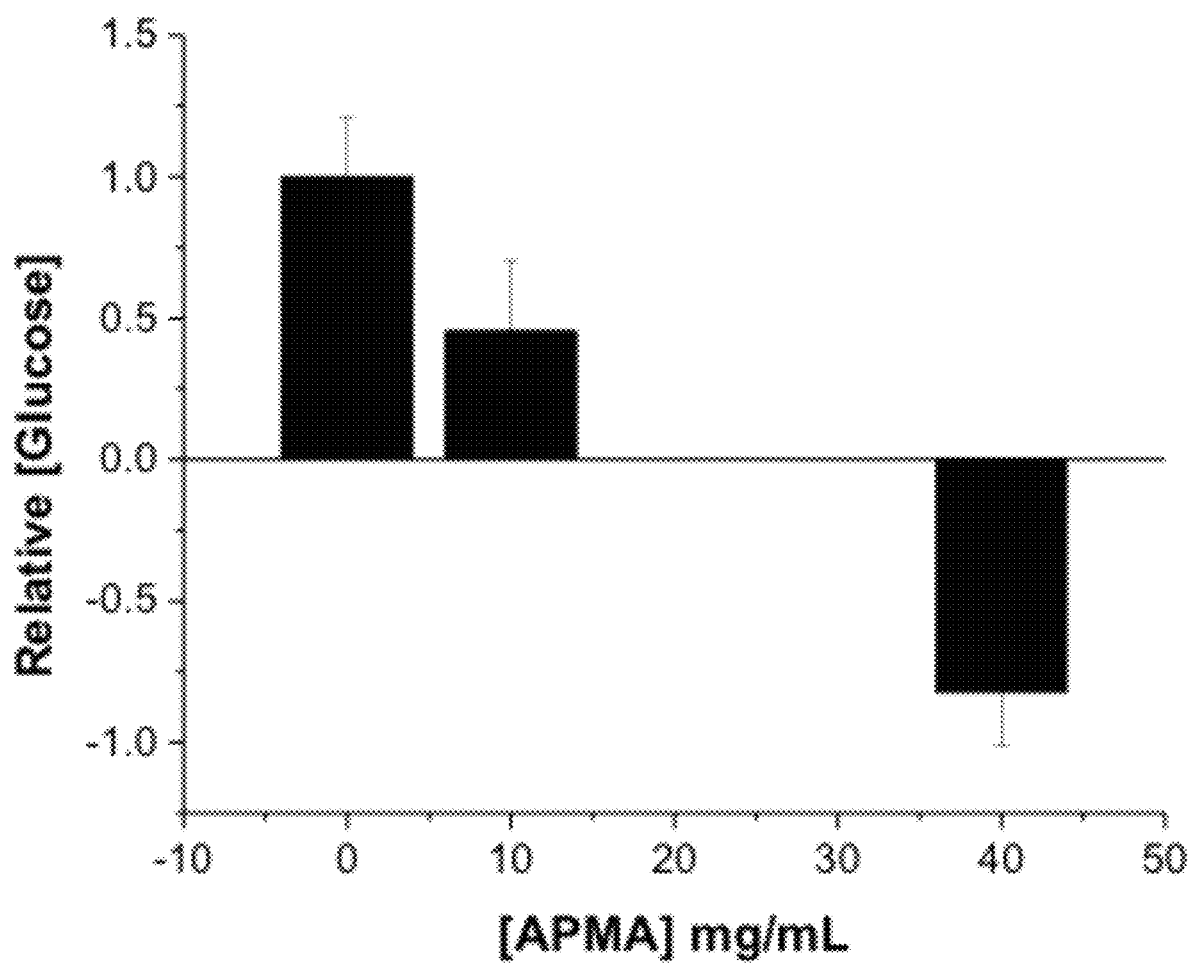
FIG. 12 depicts glucose export in presence of APMA. Relative glucose concentration in the chloroplasts medium containing 0% or 0.1% or 0.4% w/v APMA. The data are expressed as the average±SD (n=3).
Figure 13:
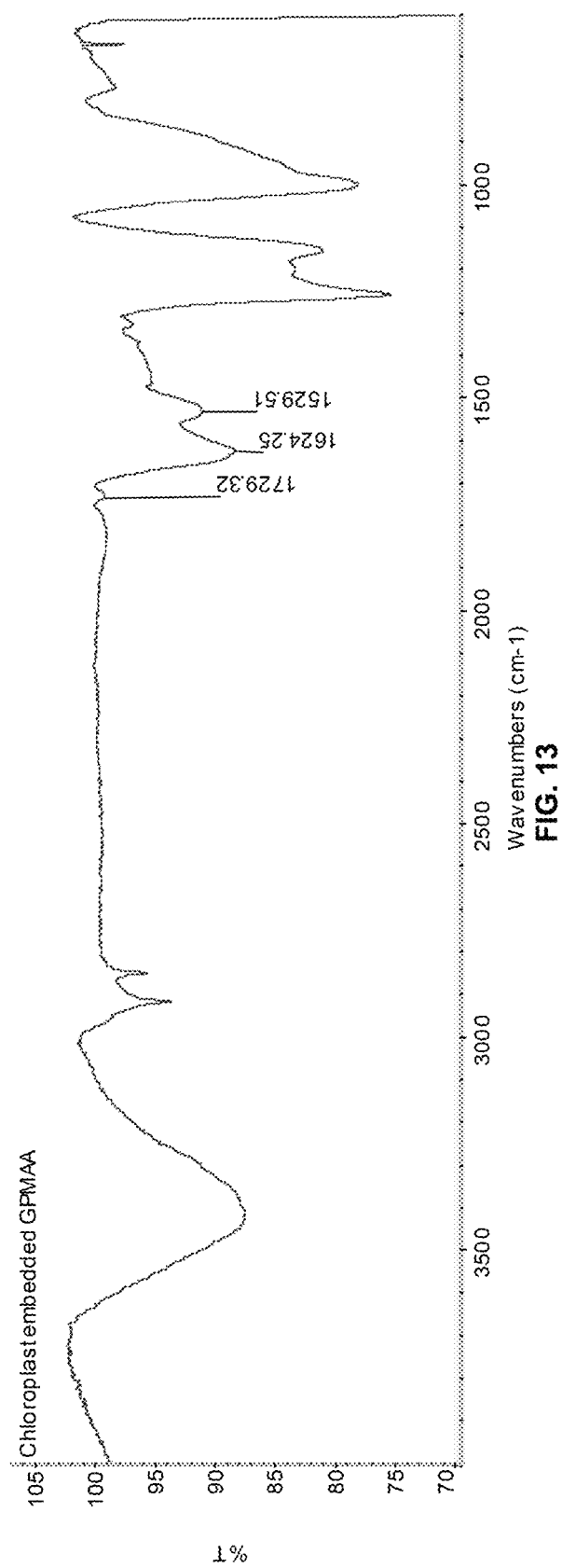
FIG. 13 depicts an FT-IR spectrum of chloroplast embedded GPMAA hydrogel. Isolated chloroplasts were kept under the ambient light overnight. The chloroplast medium contained GOx (20 U mL−1) and 0.1% APMA. IR peaks were confirmed by Fourier transform infrared spectroscopy (FT-IR) spectroscopy with an FTIR microscope.

(+0.19) kPa, which is approximately 9 times higher. The shear modulus of GPMAA hydrogel at 18 h (completely formed) is 3.0 (+0.087) kPa, which is still approximately 17% lower than that of graphene oxide containing GPMAA. A low fraction of graphene oxide was observed to stiffen hydrogel 3 times faster by accelerating crosslinking, enhancing the mechanical strength by 17% as the composite material is intertwined by hydrogen bonds between hydroxyl and epoxy groups of graphene oxide sheets and GPMAA chains (FIGS. 2B and 9A-9D). The hydrogel exhibits adhesive properties, which displays characteristic fibrillar structure and shear strength profile during the separation process (FIGS. 2C and 2D) and can hold the weight of 12 mL of water in a centrifugal tube (FIGS. 11A-11C).

Engineering of Extracted Spinach Chloroplasts

Since glucose export from the extracted chloroplasts is a potential rate-limiting step in material growth, this prompted an optimization study on glucose export. Chloroplasts, plant organelles contained within the cytoplasm of the plant cell, are the main sites of carbon fixation and photosynthesis in plants. They have been explored as candidates for solar energy generation and efficient carbon dioxide sequestration (100 µmol $CO_2$ $mg^{-1}$ Chl $h^{-1}$) due to their inherent ability to export stored chemical energy, abundance in nature, and scalable isolation from plant matter. However, they have not been used as components within materials. Exported sugars ultimately participate in the sucrose synthetic pathway through a series of enzymatic reactions in the cytoplasm of protoplasts. This pathway is absent in isolated chloroplast, potentially yielding accumulation of exported glucose and increased availability for material synthesis. Therefore, extracted chloroplasts can accumulate exported saccharides with the absence of the sucrose synthetic route.

Figure 3A:
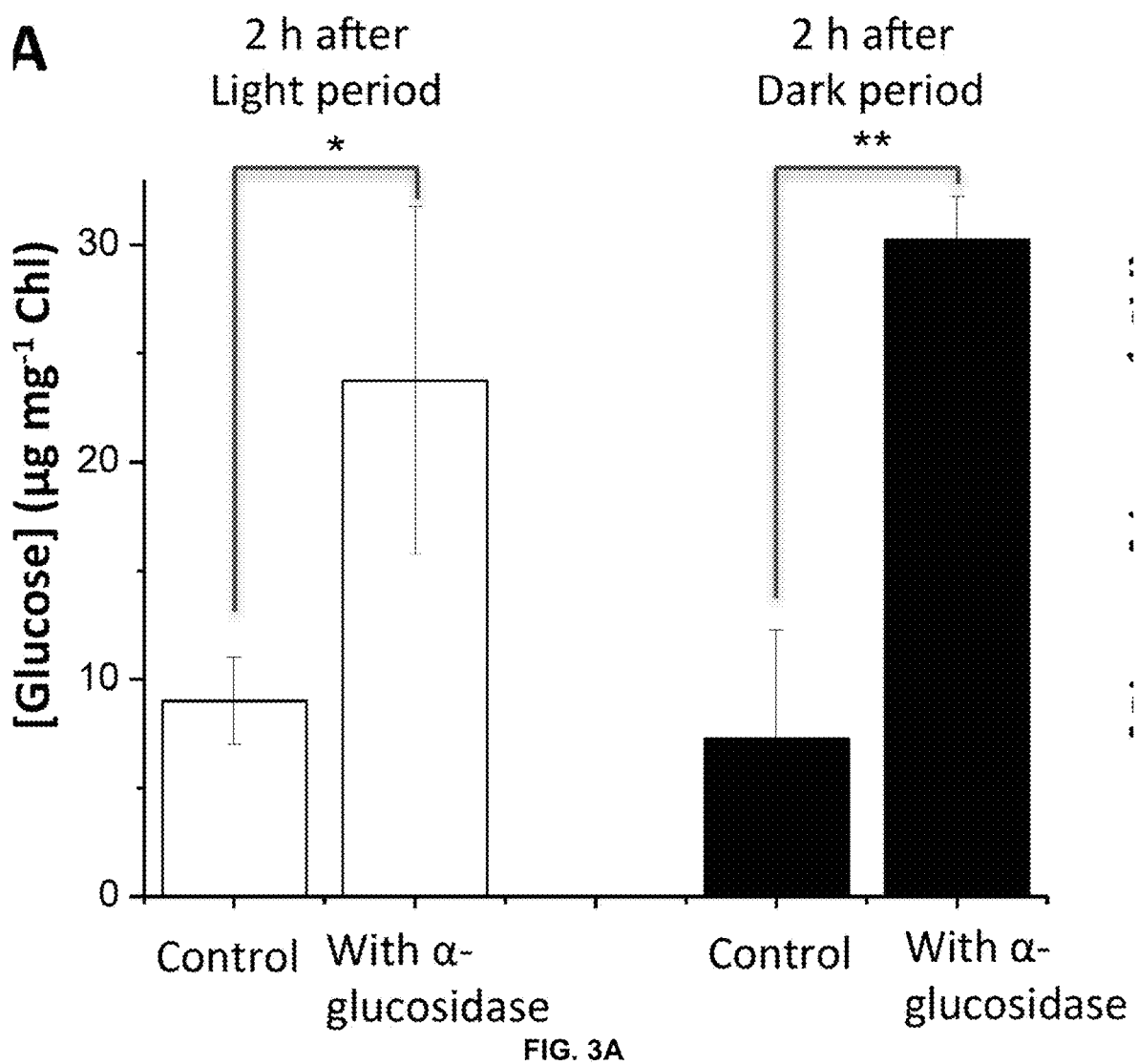
FIGS. 3A-3F depict a systematic investigation on boosting glucose synthesis and export from isolated chloroplast.

Several biochemical and nano-biotechnological approaches were explored to increase the export rate of glucose from isolated chloroplasts. Under dark conditions, maltose and glucose are the major sugars exported from chloroplasts. Maltose is a disaccharide consisting of two glucose molecules joined with a $\alpha(1\rightarrow4)$ glycosidic bond that α-glucosidase can hydrolyze. Therefore, α-glucosidase can be used in the chloroplast incubation medium as a means of converting the maltose to glucose and boosting the glucose yield. The glucose concentration outside of the extracted chloroplast after 2 h of light and 2 h of dark period with α-glucosidase is about 3 times higher than that of control without α-glucosidase (FIG. 3A). This proves that the maltose is exported from the chloroplast and subsequently broken down by enzymatic hydrolysis to produce additional glucose molecules for eventual polymerization.

Figure 3B:
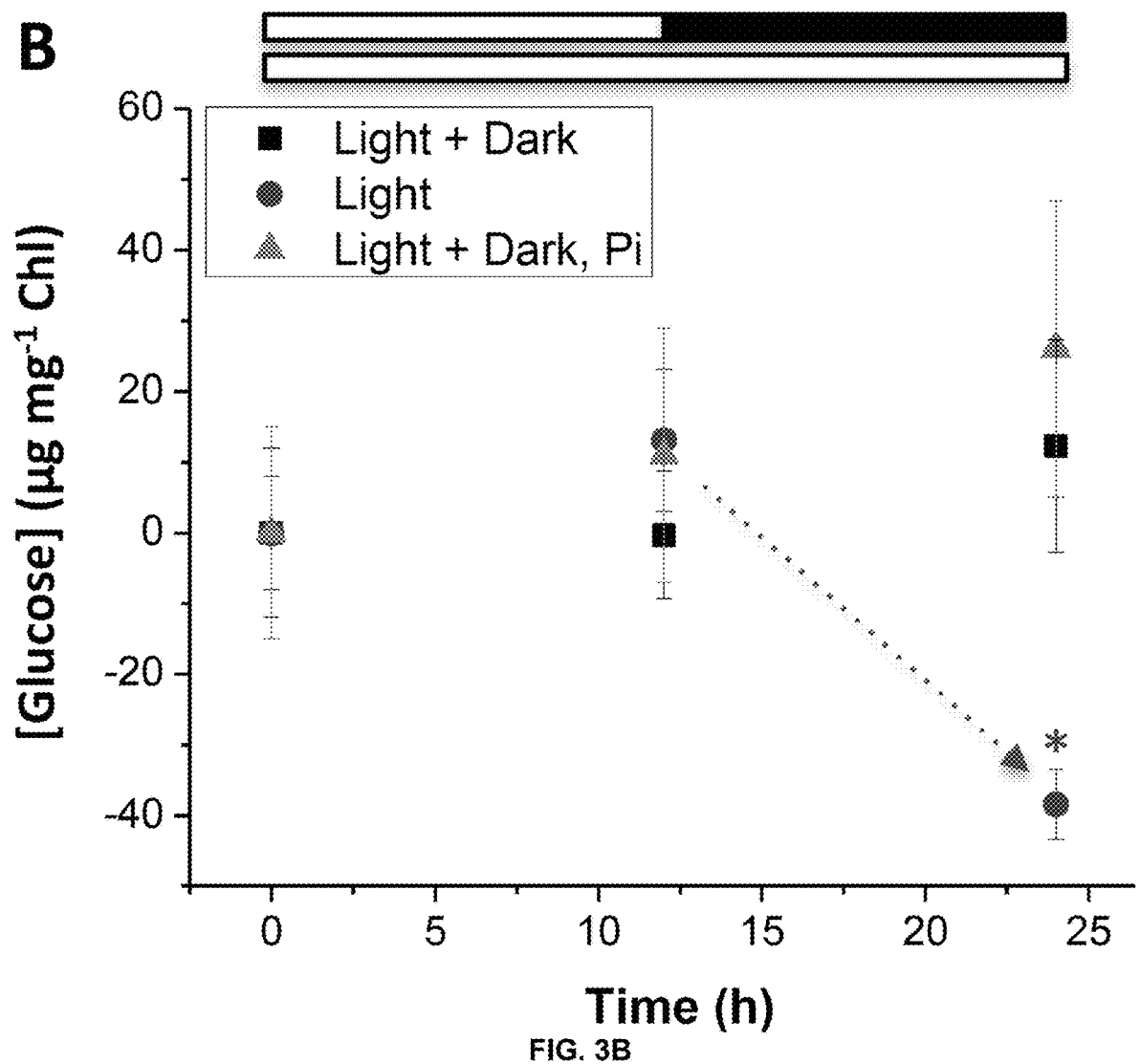

Starch formation and sucrose synthesis are often viewed as competitive processes since starch is formed in the chloroplasts by photosynthesis during the day and exported after being broken down to synthesize sucrose at night. Indeed, glucose concentration significantly declines under continuous illumination for 24 h without an intermittent dark period (FIG. 3B). This appears consistent with the starch degradation process becoming latent or a glucose influx competitively operating with glucose export. Alternatively, if stored in the dark for 24 h, chloroplasts equilibrate glucose to a constant concentration (FIG. 3B), which supports the conclusion that a prior period of illumination is necessary before a dark period for starch formation, breakdown and glucose export.

Another important variable is inorganic phosphate (Pi) concentration. It is known to play a key role in photosynthesis and carbon metabolism. The photosynthesis of isolated chloroplasts soon ceases in the absence of Pi but restarts with exogenous addition of Pi to the medium. Consequently, a Pi deficiency can limit carbon export from isolated chloroplasts. To investigate the importance of external Pi concentration on glucose export, isolated chloroplasts are incubated in buffer containing 5 mM Pi, with subsequent hourly additions of Pi to the incubation medium to maintain an external Pi concentration. However, an insignificant difference in external glucose concentration can be seen with this high Pi supply as shown in FIG. 3B. Supplying external Pi can be an ineffective strategy to increase the glucose export rate in extracted chloroplasts.

Figure 3C:
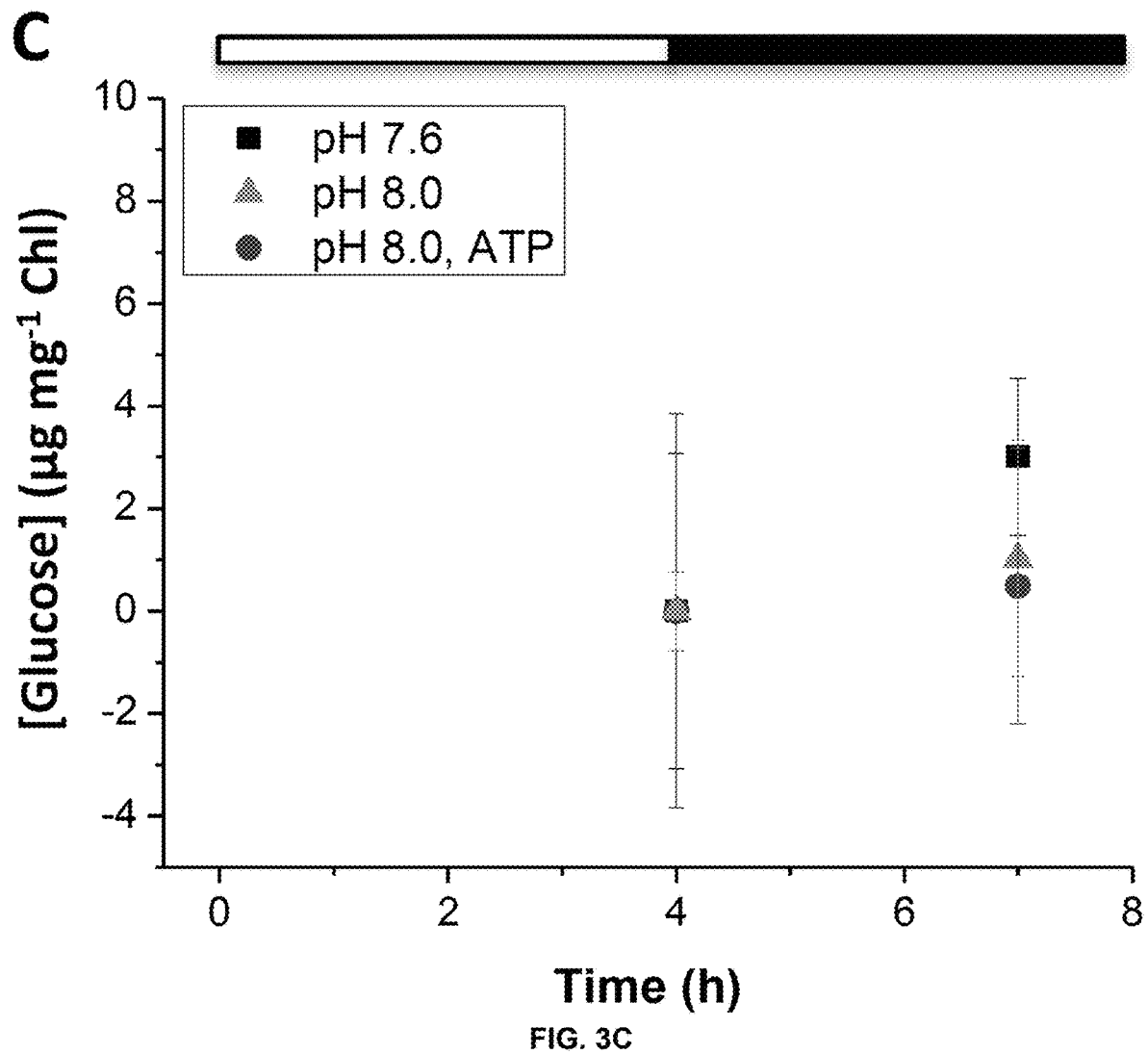
Figure 3D:
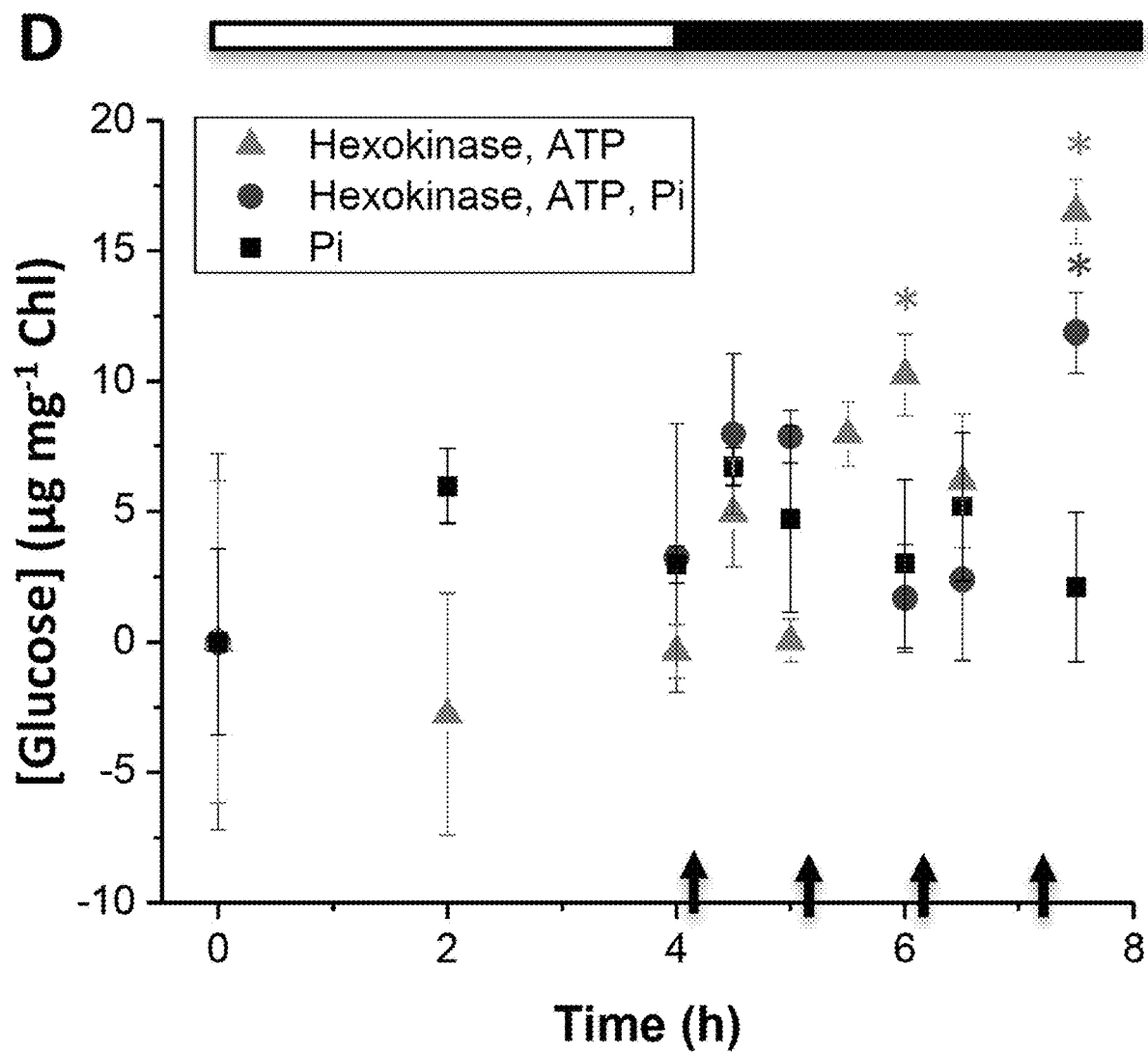

The membrane mechanisms for glucose export can also equilibrate with an influx rate, leading to limiting glucose concentrations outside the chloroplast. As another optimization variable, the pH of the chloroplast suspension was adjusted from pH 7.6 to pH 8.0 to mimic the proton gradient between the chloroplast stroma and the external environment in the dark. FIG. 3C shows that the change in glucose concentration is negligible and within the error range even with the introduction of external adenosine triphosphate (ATP) to induce the active transport of glucose in the presence of 5 mM Pi. To minimize glucose influx and increase glucose export, the external glucose concentration was continually lowered by converting glucose to glucose-6-phosphate by hexokinase. This results in an increase of glucose export at a rate of approximately 5 µg $mg^{-1}$ Chl $h^{-1}$ in the dark period (FIG. 3D). In a biological system, negative feedback is a well-known regulatory mechanism in which the formation of a product in turn reduces the driving force for its own production. However, this is the first demonstration of boosting the net glucose export from isolated chloroplasts by adjusting the glucose gradient across the chloroplast membrane. As expected, additional Pi results in insignificant enhancement of glucose export from isolated chloroplasts.

Stabilization Through Plant Nanobionics.

Figure 3E:
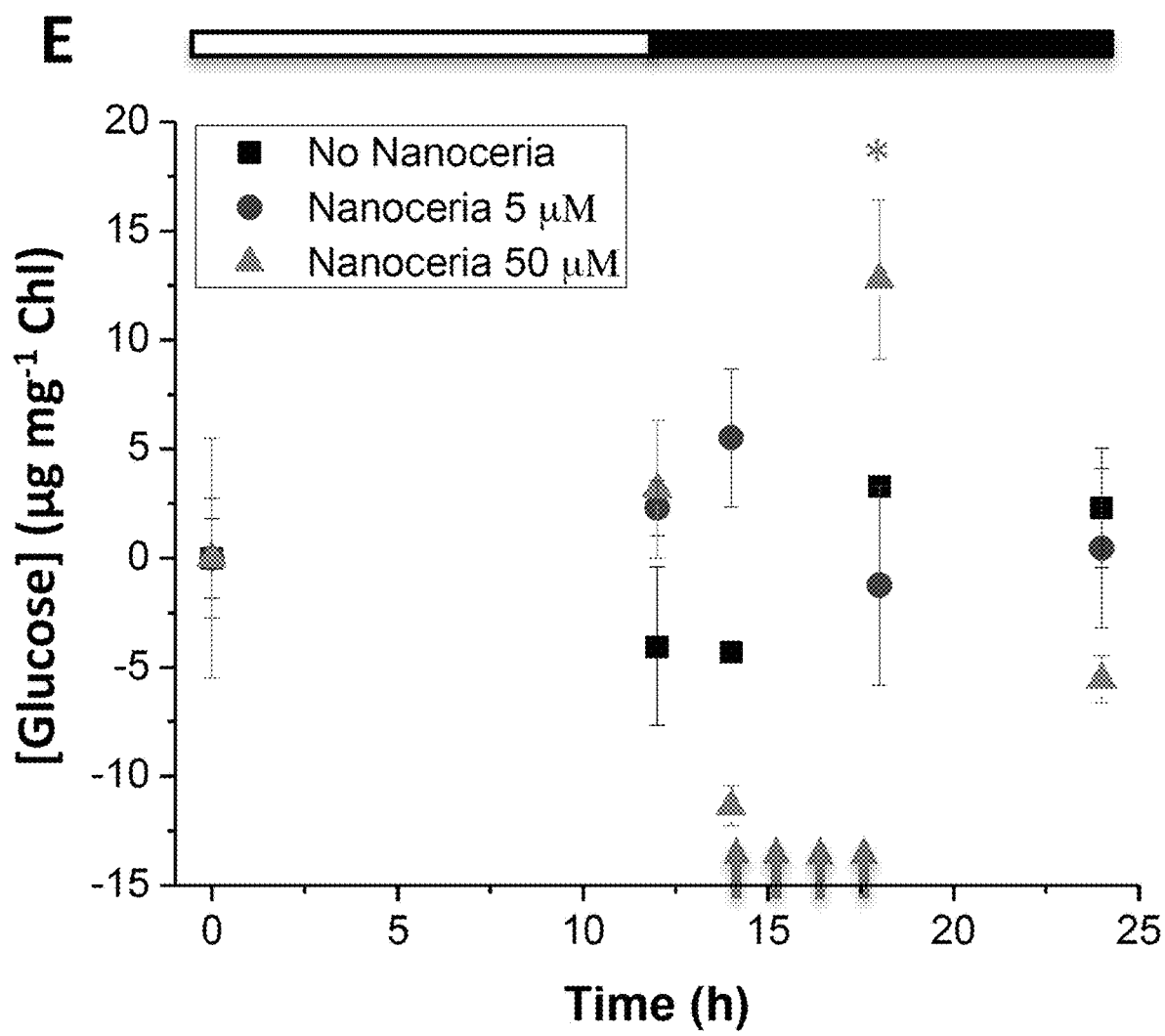

Chloroplasts outside of the plant cells have limited photoactive lifetimes of less than a day and only a few hours for saccharide export. Several strategies have been attempted to extend chloroplast photostability, for example by encapsulating chloroplast in biologically inert matrices and altering conditions such as illumination, temperature, and buffer composition. Previously, our group showed that potent antioxidant cerium oxide nanoparticles, nanoceria, could extend the photoactive lifetime of isolated chloroplasts by scavenging reactive oxygen species (ROS) produced as a by-product of photosynthesis. However, the effect of ROS scavenging on glucose export remained unknown. The protection of the carbon export system from ROS-related degradation or photodamage can help maintain high carbon export rates for a longer period of time. Isolated chloroplasts are first pre-incubated with nanoceria to allow the nanoparticles to enter the chloroplasts. After the incubation, the buffer was replaced with a fresh buffer without nanoceria and the chloroplast suspension is illuminated for 4 h and subsequently kept in the dark for 4 h. To boost glucose export, hexokinase was added every hour during the dark period. An insignificant effect on glucose export is observed at both low (5 µM, 0.56 mg $L^{-1}$) and high (50 µM, ~5.6 mg $L^{-1}$) concentration of nanoceria (FIG. 11C). When the light period was extended from 4 h to 12 h, 50 µM nanoceria gives a positive effect on glucose export after 6 h from the start of dark period, while a marginal improvement is observed at 5 µM (FIG. 3E). Removing photo-generated ROS inside chloroplasts can extend the lifetime of isolated chloroplasts, which ultimately translates into higher glucose accumulation in the medium. Glucose export increases only after the addition of hexokinase, which acts as a sink for this flux outside of the chloroplast.

Figure 3F:
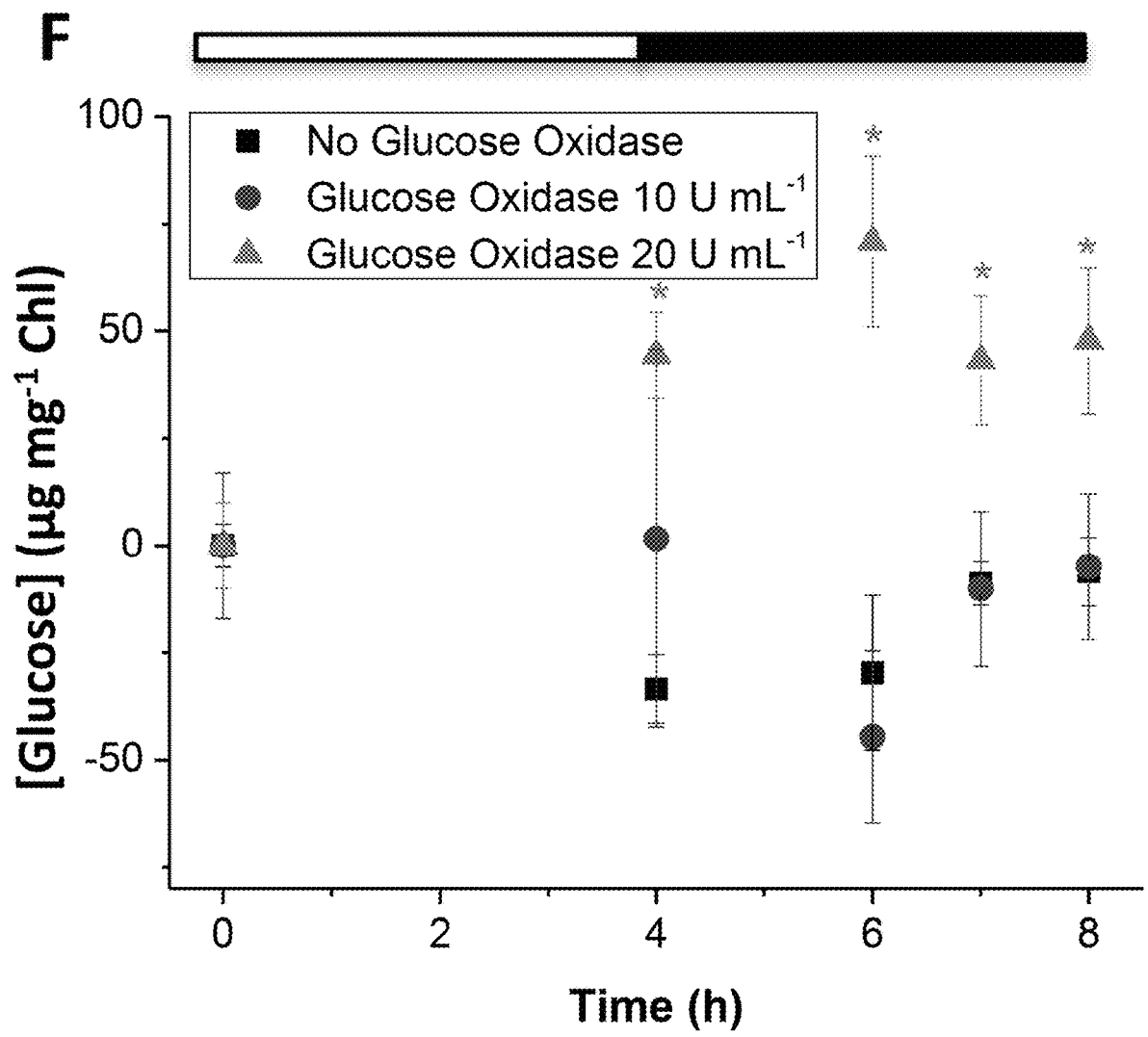

In all, the yield of glucose can be increased using enzymatic hydrolysis of maltose exported from isolated chloroplasts. A net increase in glucose export was observed by adjusting the glucose gradient across the chloroplast membrane, optimizing the illumination period and enhancing the photo-stability of chloroplasts. These findings can be applied to boost glucose export from isolated chloroplasts with the ultimate goal of conversion to the monomer, GL. Similar to the regulation of glucose equilibrium across the chloroplast membrane by hexokinase (FIG. 3D), the conversion reaction of external glucose to GL by GOx promotes glucose export by suppressing glucose accumulation in the medium (FIG. 3F). In the presence of 20 U mL-1 GOx, the GL concentration notably increases at a rate of 12 $\mu$mg$^{-1}$ Chl h$^{-1}$ whereas the lower (10 U mL$^{-1}$) concentration of GOx leads to negligible improvement in the glucose export rate (FIG. 3F). This increase reaches to a plateau within a few hours and the GL concentration barely increases in higher GOx (50-100 U mL$^{-1}$) (FIG. 11C). The fast accumulation of $H_2O_2$ from GOx enzymatic catalysis may contribute to this saturation. In the presence of high $H_2O_2$ concentration, $CO_2$ fixation ceases or its rate significantly diminishes since $H_2O_2$ and $CO_2$ both compete for photoreductants generated in the thylakoids of chloroplasts. From the continuous increase of GL during the illuminated period, the glucose gradient adjustment across the membrane can be the more critical variable that affects glucose export than manipulating the light/dark cycle (FIG. 11C). This brings huge benefits to the chloroplast-embedded hydrogel growth since photosynthesis, glucose export and conversion, and polymerization can occur all together under the illumination.

Carbon Fixation in the Hydrogel System

Figure 4A:
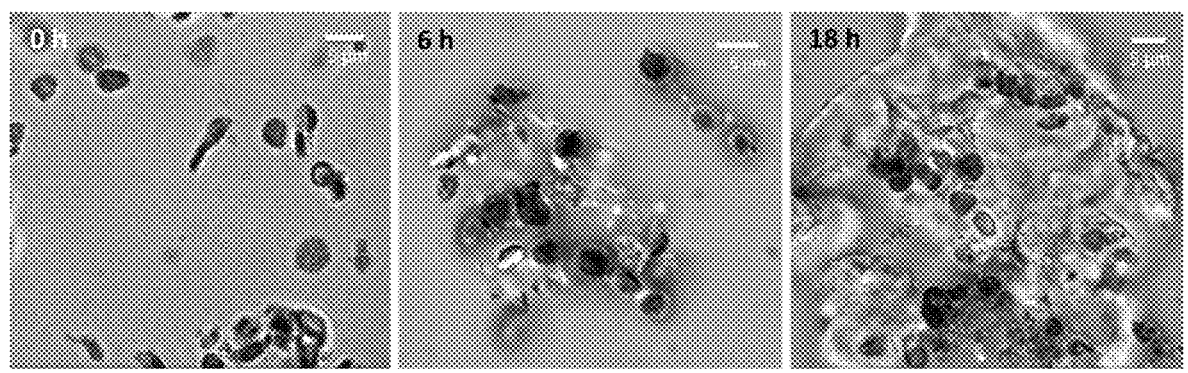
FIGS. 4A-4D depict hydrogel growth over time from ambient carbon dioxide and light around isolated chloroplasts.
Figure 4B:
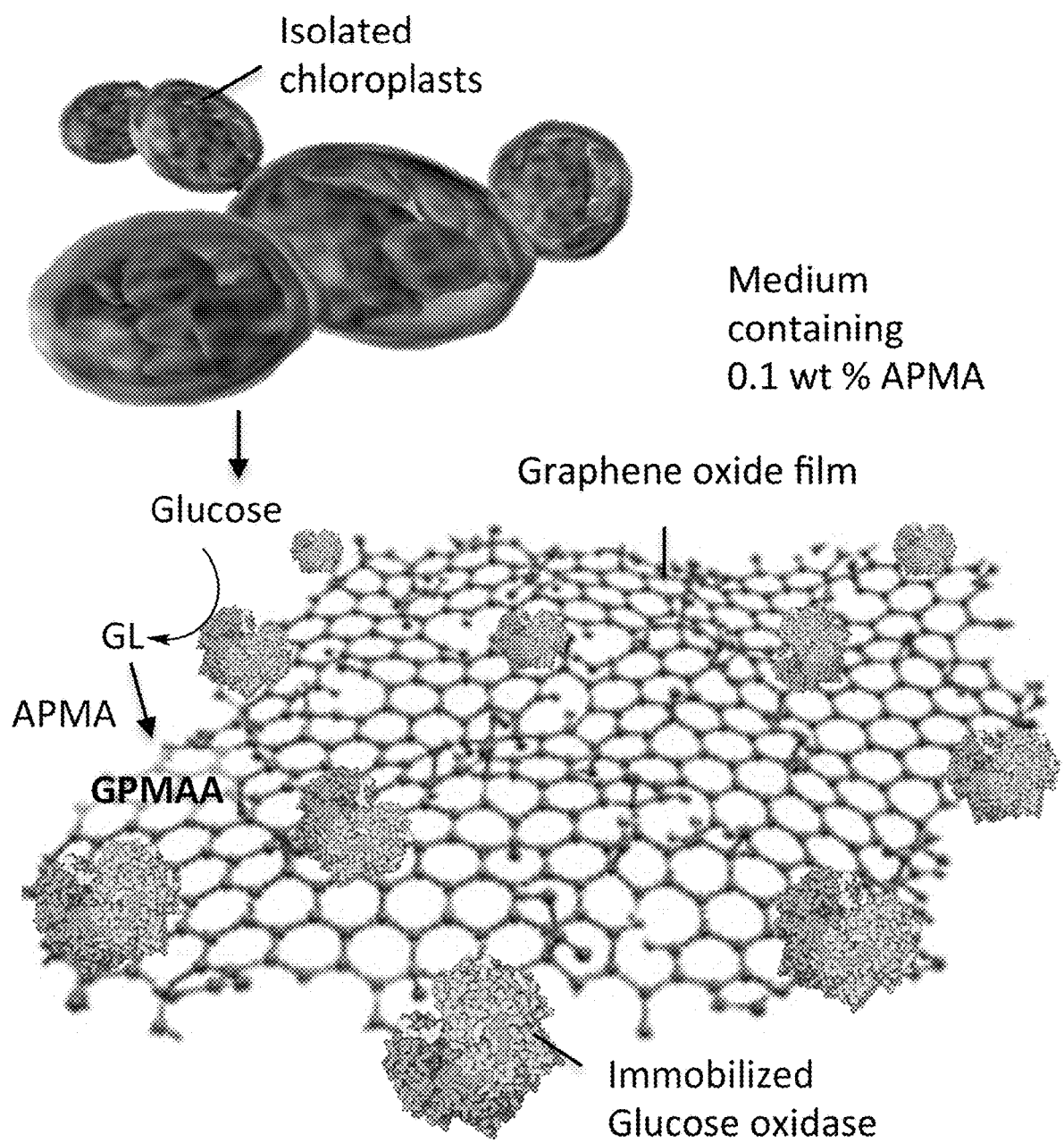
Figure 14:
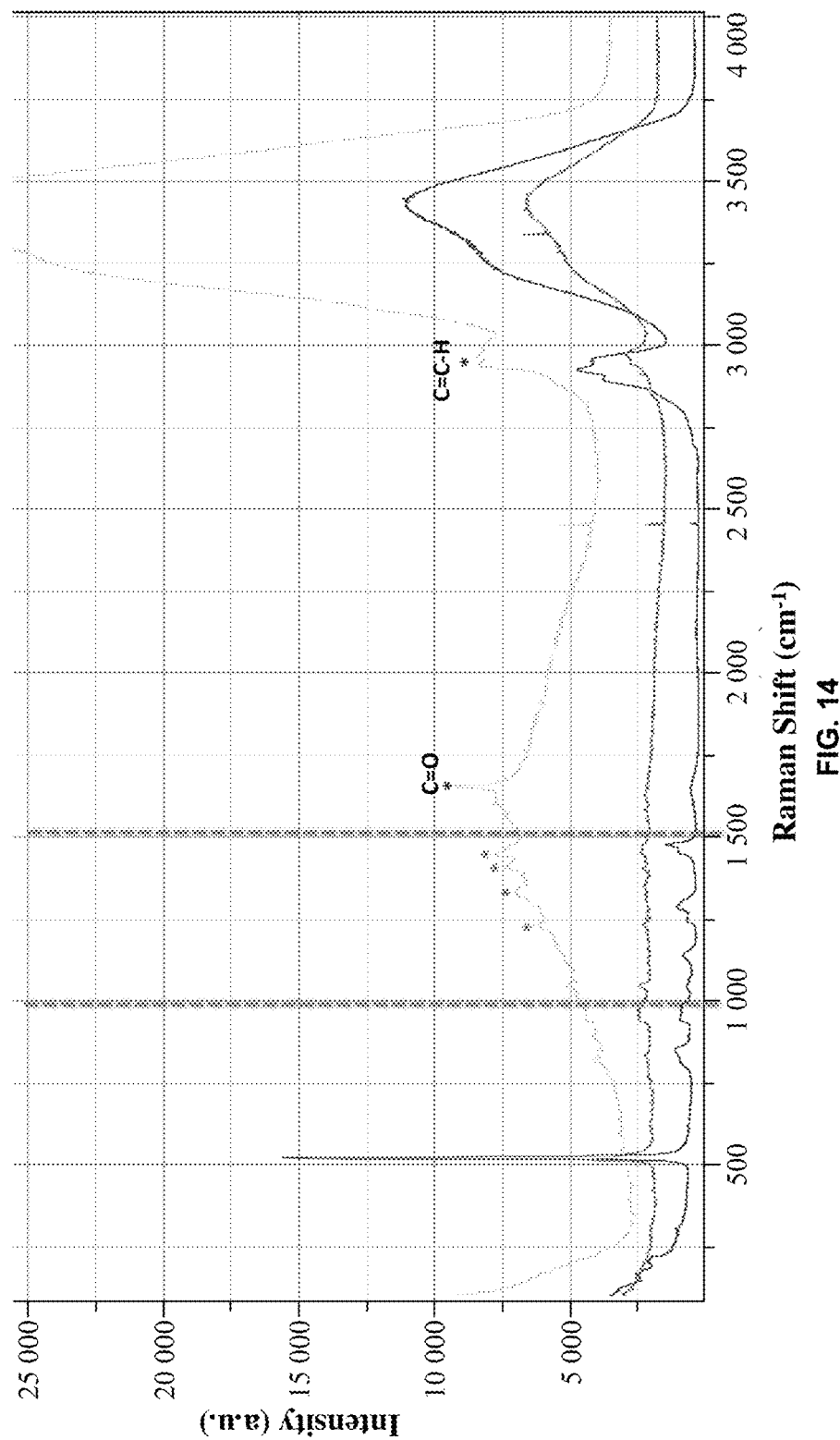
FIG. 14 depicts Raman spectra of chloroplast buffer alone (blue), the buffer containing 20 U/mL glucose oxidase (red) or 0.1% (w/v) APMA (green).
Figure 16A:
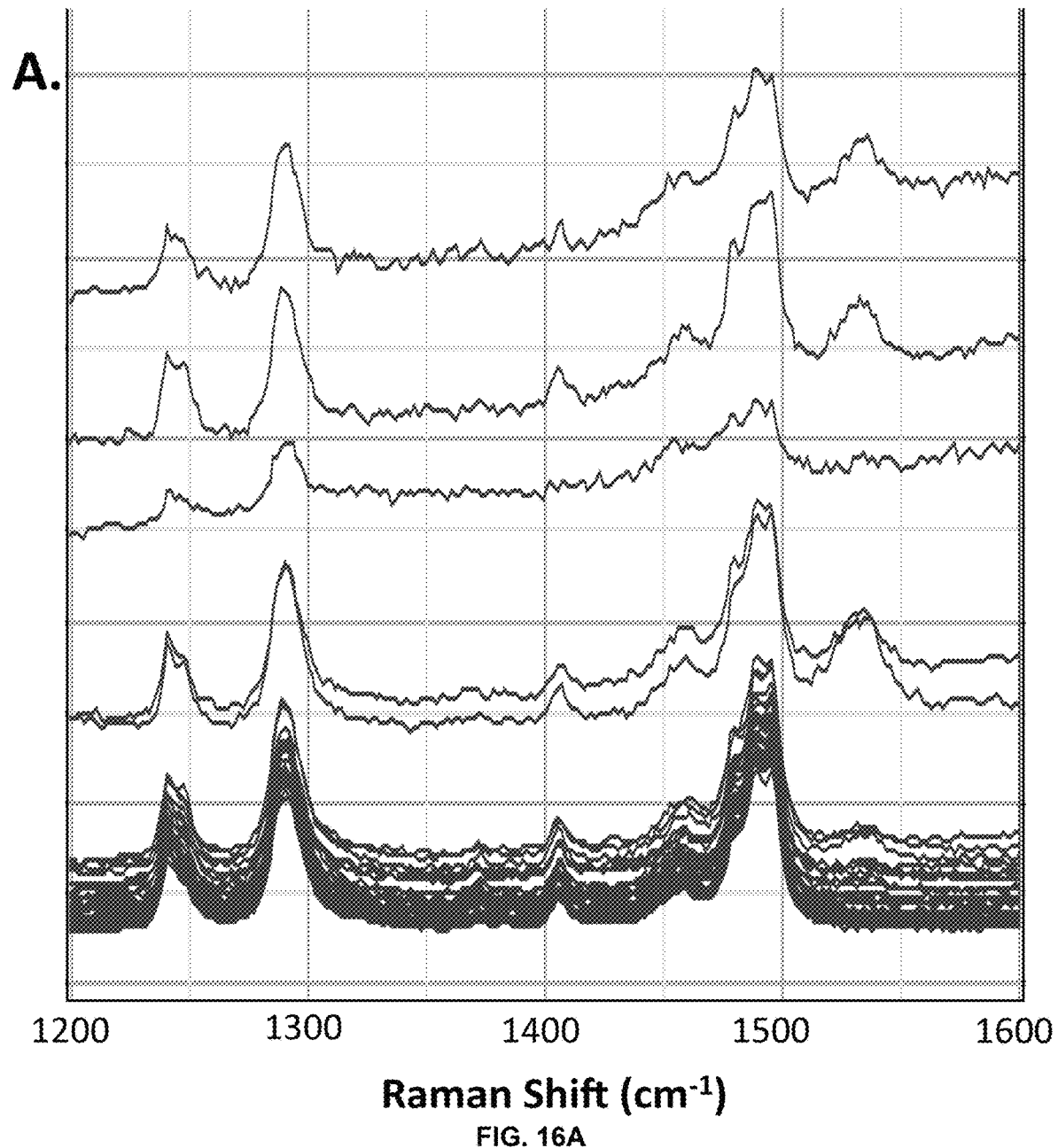
FIGS. 16A-16B depict Raman spectra of chloroplast suspension containing glucose oxidase and AMPA. Isolated chloroplasts are incubated in the presence of glucose oxidase (20 U/mL) and 0.1% (w/v) AMPA overnight in the dark (FIG. 16A) or under the light (FIG. 16B). The stacked Raman spectra are obtained from multiple spots near the chloroplasts.
Figure 16B:
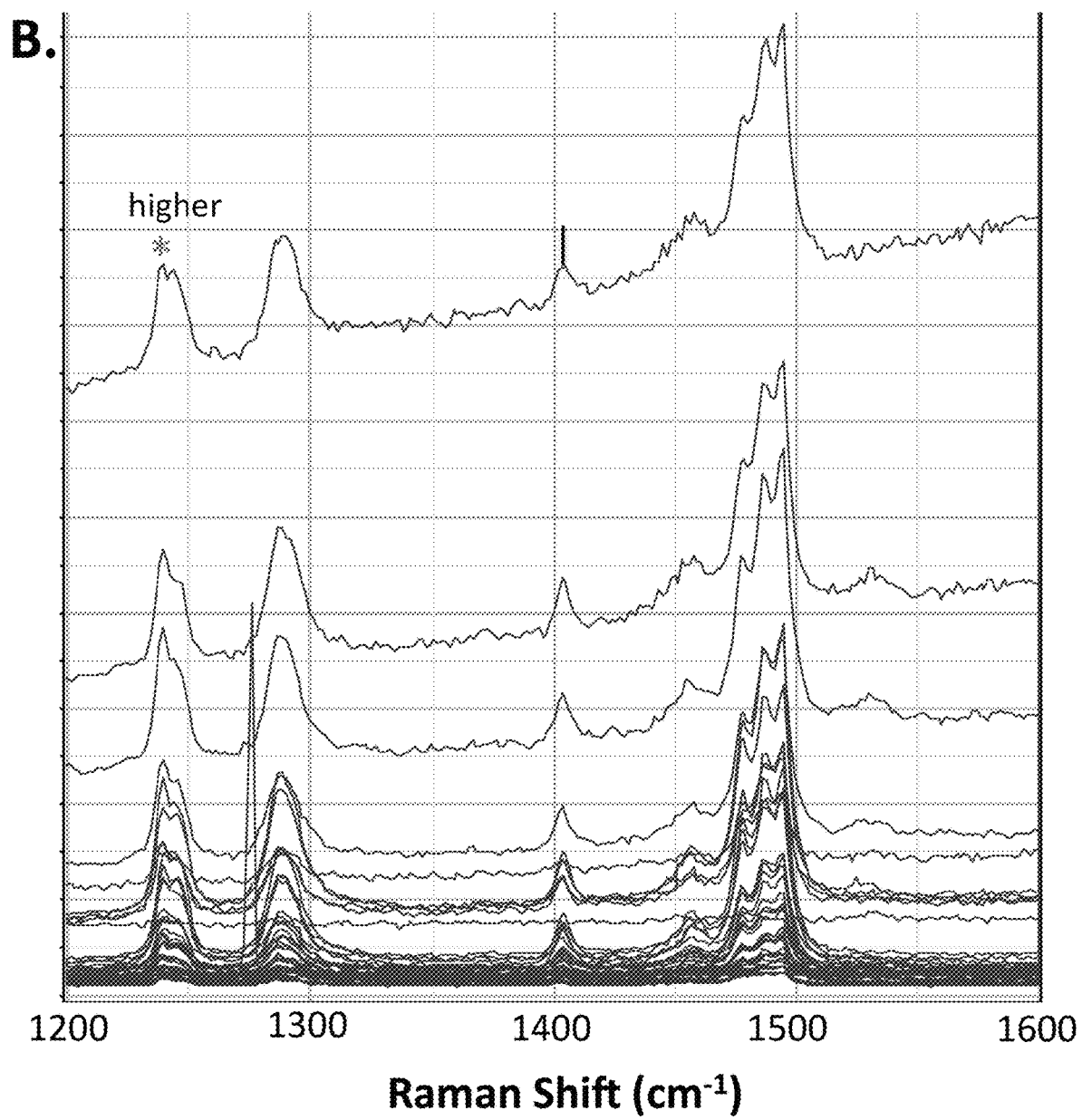

Putting these components together, a material that autonomously grows, strengthens and repairs itself in response to certain types of damage was constructed. Isolated chloroplasts were pre-incubate with 50 $\mu$M nanoceria for 3 h at 4° C. to prolong their lifetime, and then replace the nanoceria solution with buffer containing both APMA and GOx. It was critical to purge the remaining nanoceria from the medium because photogenerated free radicals are mechanistically essential to the polymerization and crosslinking process. Isolated chloroplasts function well in media containing up to 0.1% w/v APMA but show significantly lower glucose export rates at 0.4% w/v APMA (FIG. 14). GOx has been demonstrated to maintain its catalytic activity over that period. Within 6 h from the start of the illumination period, hydrogel-like material can be observed around the chloroplast membrane. After 18 h, the hydrogel has clearly extended to a thickness of more than 20 $\mu$m and the chloroplasts become gradually embedded in the hydrogel (FIGS. 4A and 15). When the mean concentration of glucose in the medium is 5 $\mu$M, the estimated glucose concentration near the chloroplast outer membrane is approximately 125 mM within a 100 nm distance. Therefore, the experimental results show that hydrogel forms mostly around the chloroplast membranes rather than in non-specific locations in the medium. When GOx was immobilized on the surface of graphene oxide film, glucose conversion occurs mostly on the sites where GOx is immobilized, and the resulting GL reacts with APMA subsequently to form GPMAA on the film (FIG. 4B). This is consistent with a shift in reaction kinetics from being glucose export-limited in the former case to GOx reaction-limited at the graphene oxide in the latter case. This is not a typical composite to have reinforcement effect; rather, designed for convenient characterization of the hydrogel distinguished from graphene oxide or GOx. The graphene oxide can accelerate hydrogel formation by mixing isolated chloroplasts with the GOx anchored graphene oxide suspension, as shown in FIG. 2B.

Figure 4C:
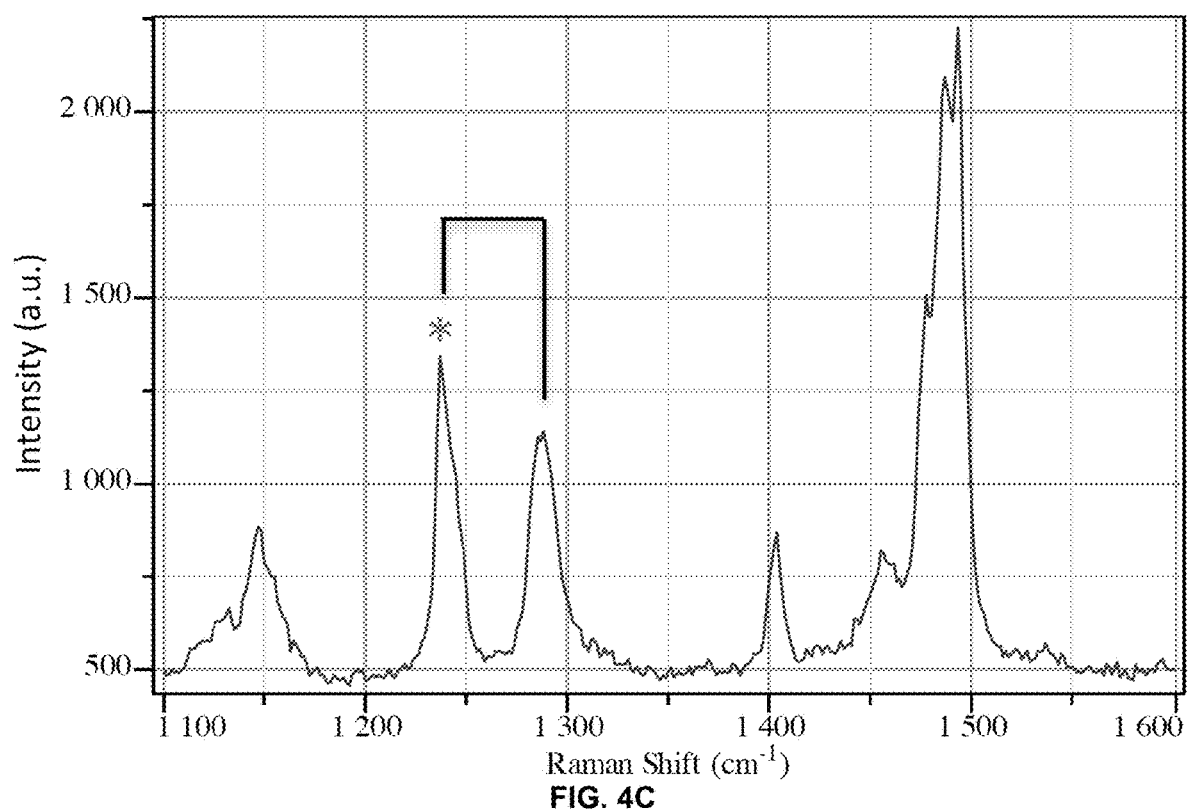
Figure 4D:
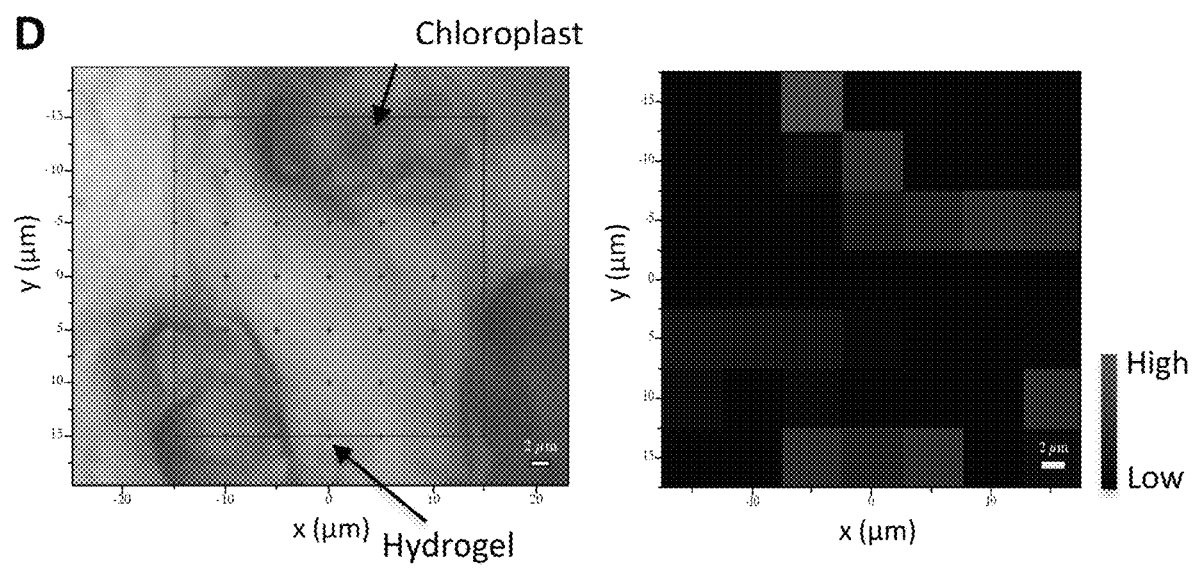

The characteristic IR peak from the newly formed amide bond in GPMAA hydrogel appears at 1625 cm$^{-1}$ on graphene oxide film (FIGS. 2A and 15). The increased Raman band at 1245 cm$^{-1}$ is tentatively assigned to v(C-N), $\delta$ (NH) in vibrational mode (amide III) (FIG. 4C). Mapping of the characteristic Raman bands of GPMAA based on the ratio between two bands at 1245 cm$^{-1}$ and at 1290 cm$^{-1}$ indicates that GPMAA hydrogel forms alongside chloroplast membranes. (FIGS. 4D, 16A-16B, and 17). The chloroplasts-embedded GPMAA hydrogel grows slowly, at a rate of 60 $\mu$m$^3$ per chloroplast in very mild conditions and can provide suitable media to maintain the viability of the isolated chloroplasts by entrapment. The growing hydrogel can protect chloroplast membrane as a physical support and scavenges $H_2O_2$ generated from glucose oxidation since $H_2O_2$ can aid polymerization and crosslinking. The stability of the embedded chloroplast activity can be a critical factor to maintain the growth rate of this material. In this study, the embedded spinach chloroplasts can be still active for more than 80 h based on our previous study. The inherent lifetime of isolated chloroplasts is species-dependent, ranging from hours to months. In addition, if $\alpha$-glucosidase and glucose dehydrogenase pyrrolo-quinoline quinone could be incorporated in the system to hydrolyze and oxidize maltose, the growing rate of the material would be enhanced due to higher monomer availability.

Characterization of Self-Healing Hydrogel Composite

Figure 5A:
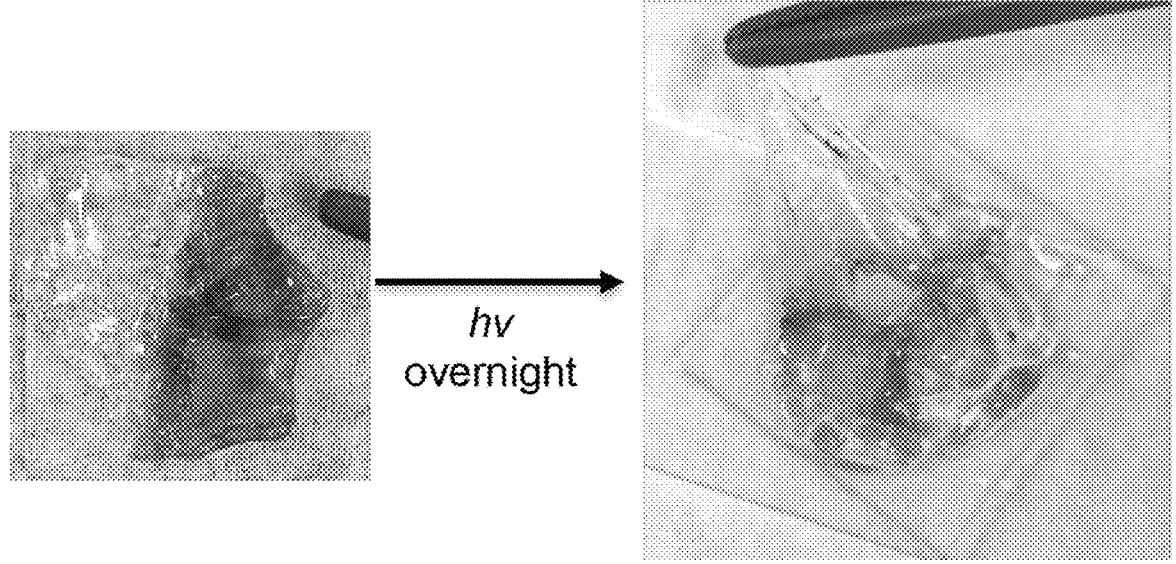
FIGS. 5A-5D depict self-repair property of GPMAA hydrogel.
Figure 5B:
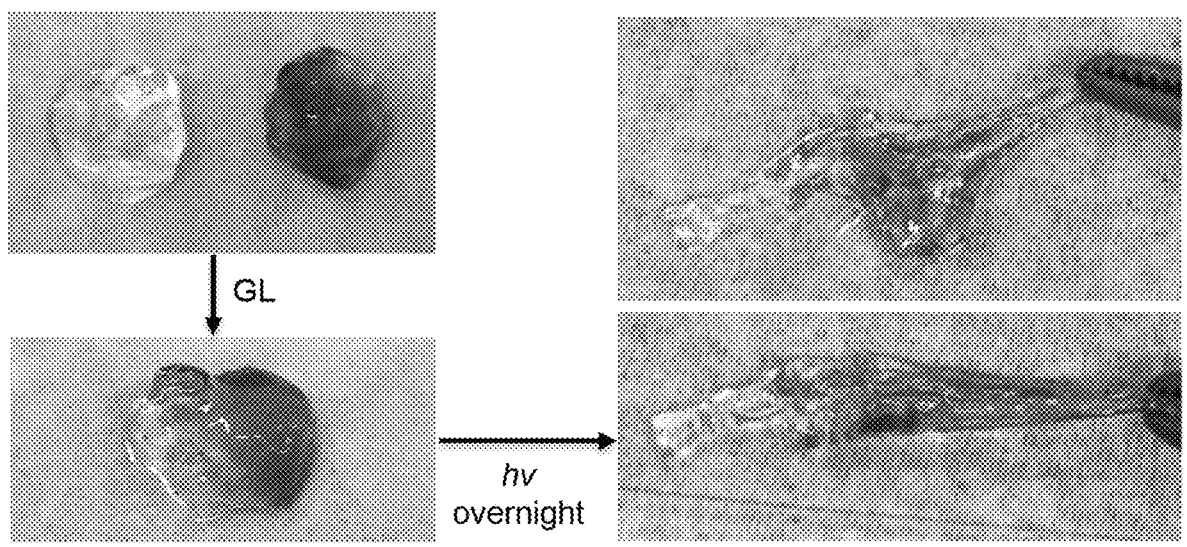
Figure 5C:
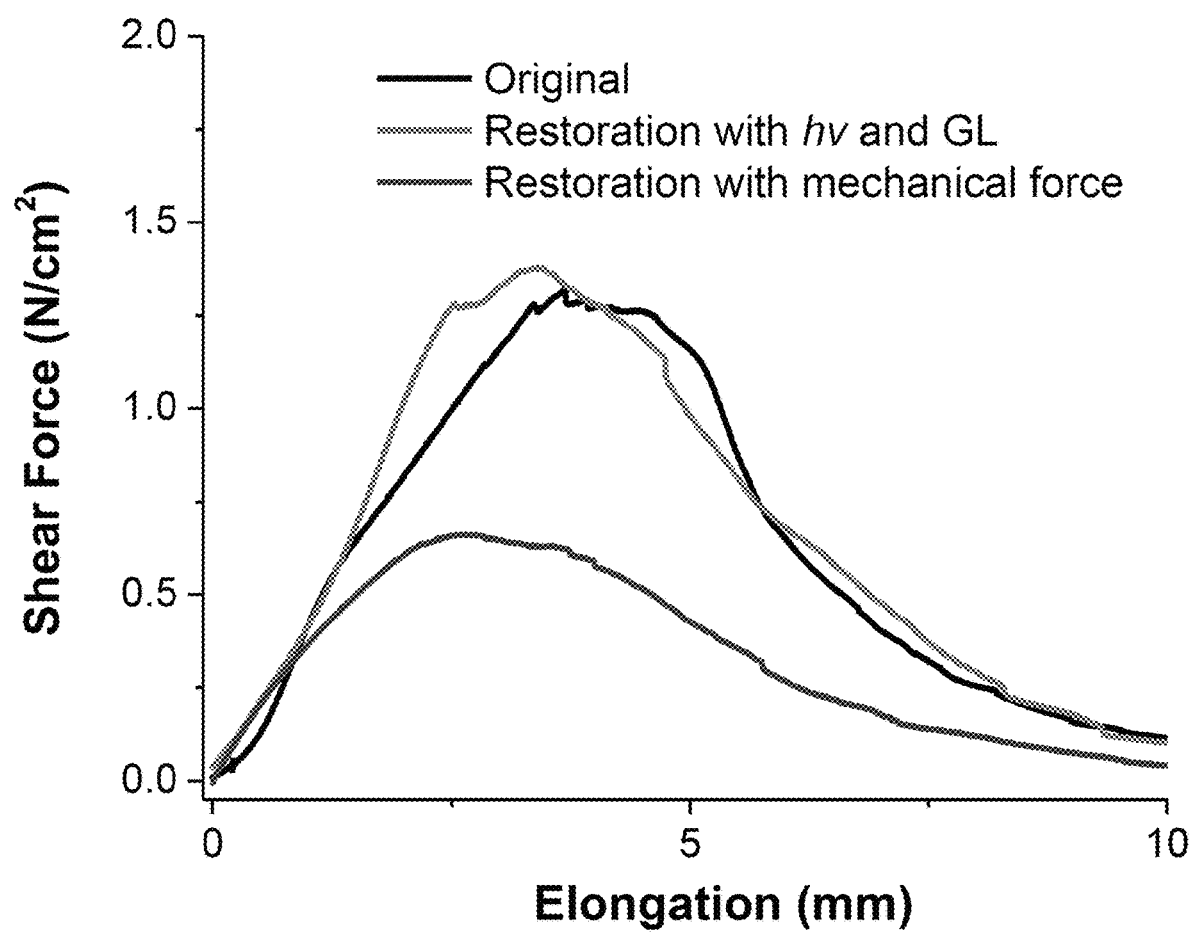
Figure 5D:
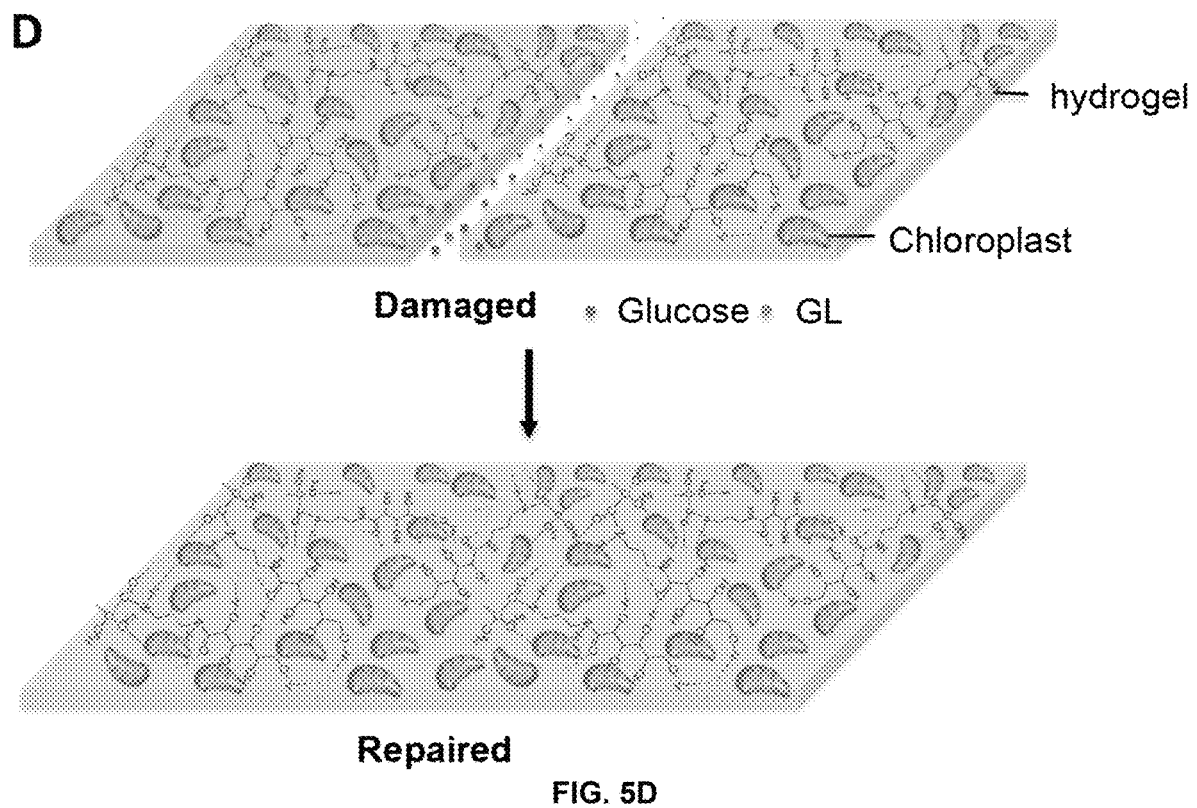
Figure 6A:
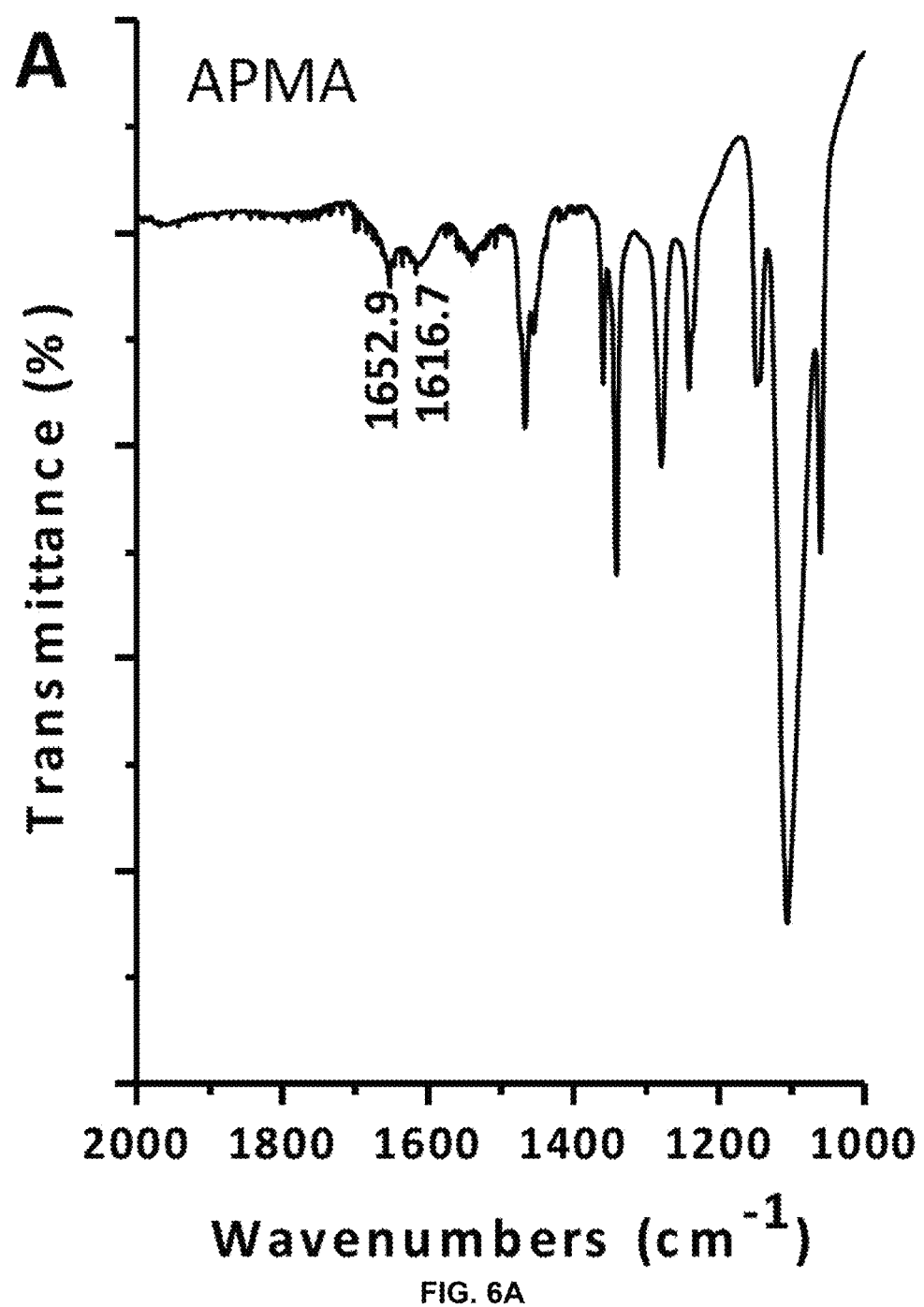
FIG. 6A-6E depict FT-IR spectra of buffer, AMPA, and GL. The characteristic peak of new amide bond between AMPA and GL is not observed.
Figure 6B:
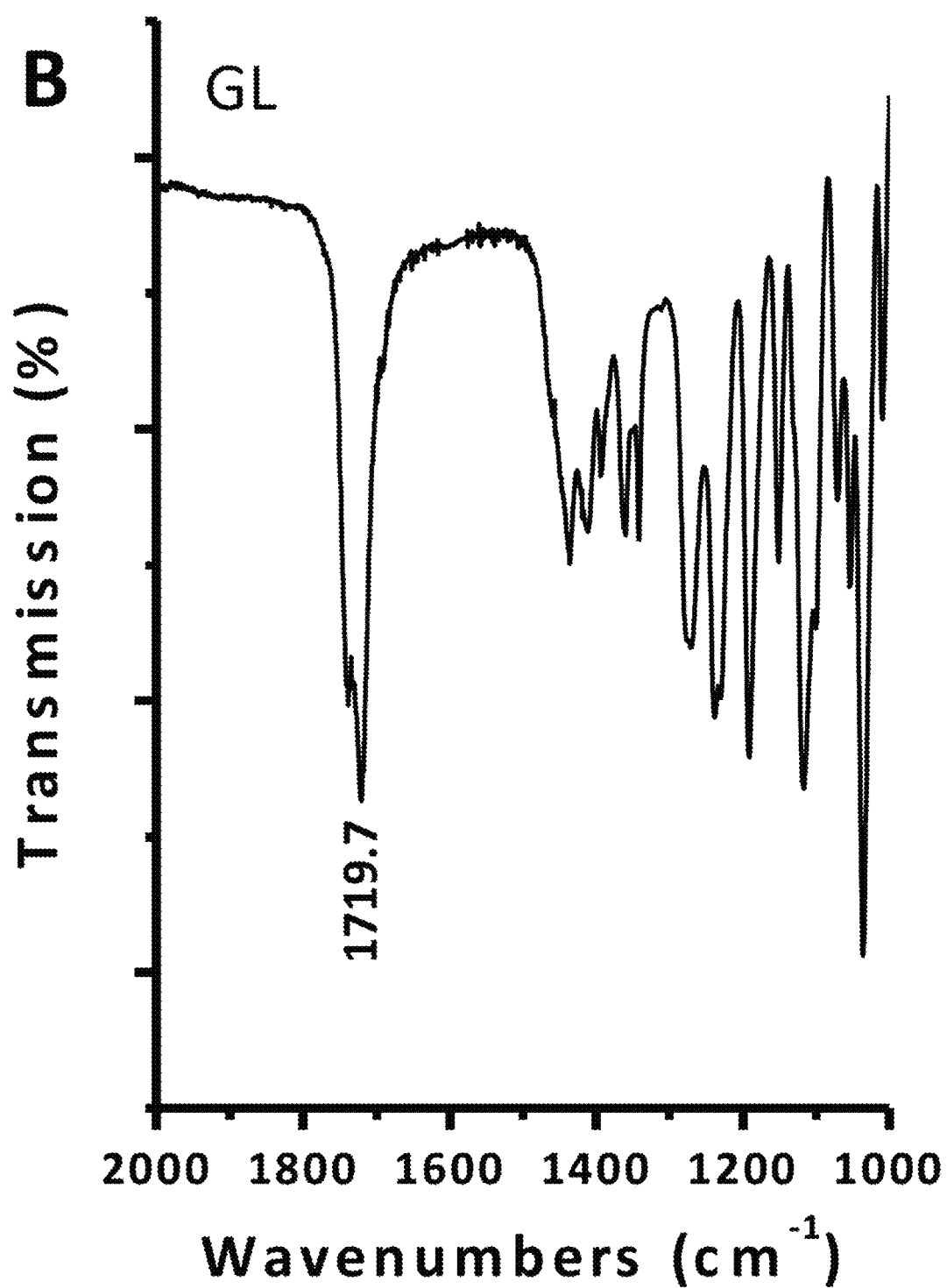
Figure 6C:
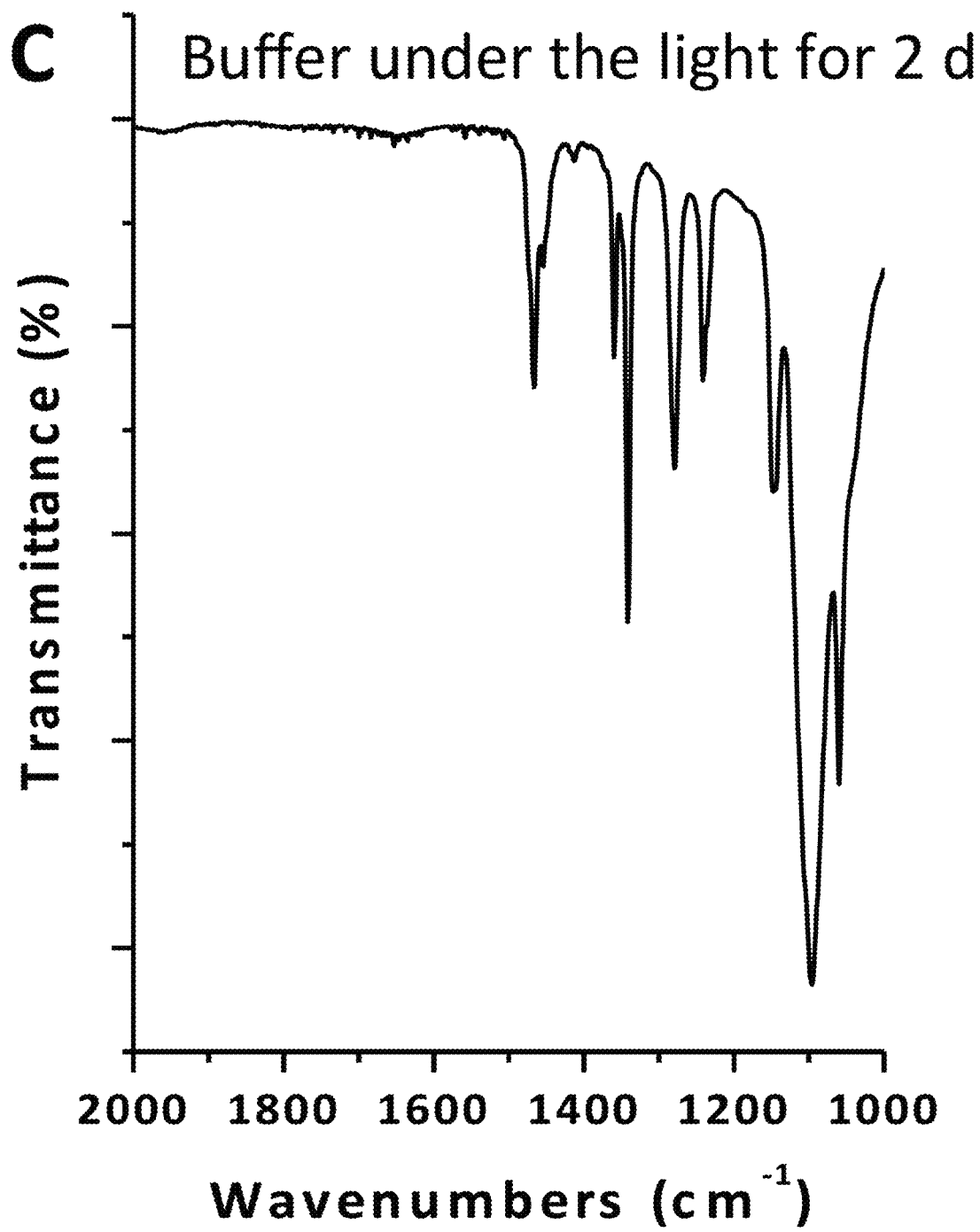
Figure 6D:
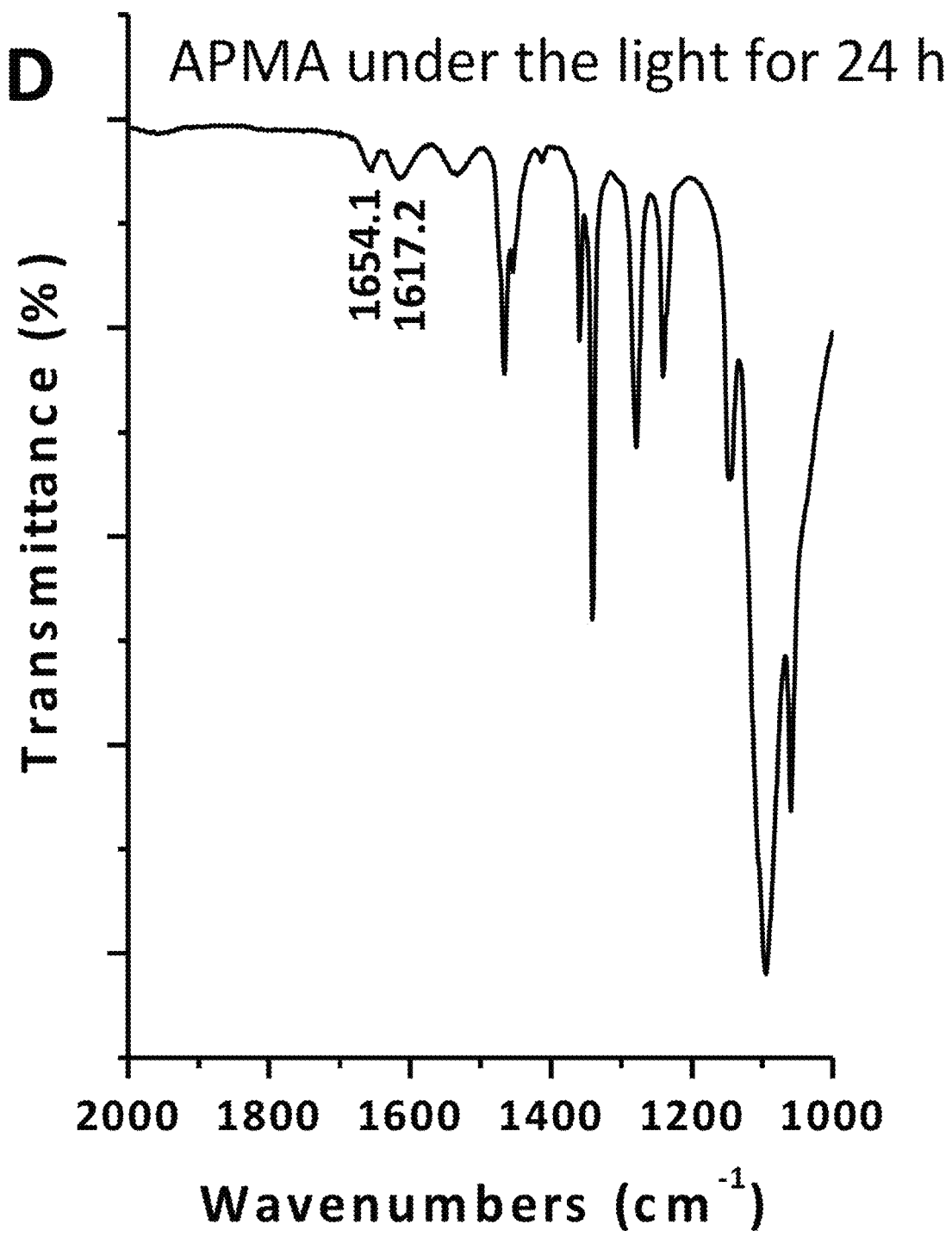
Figure 6E:
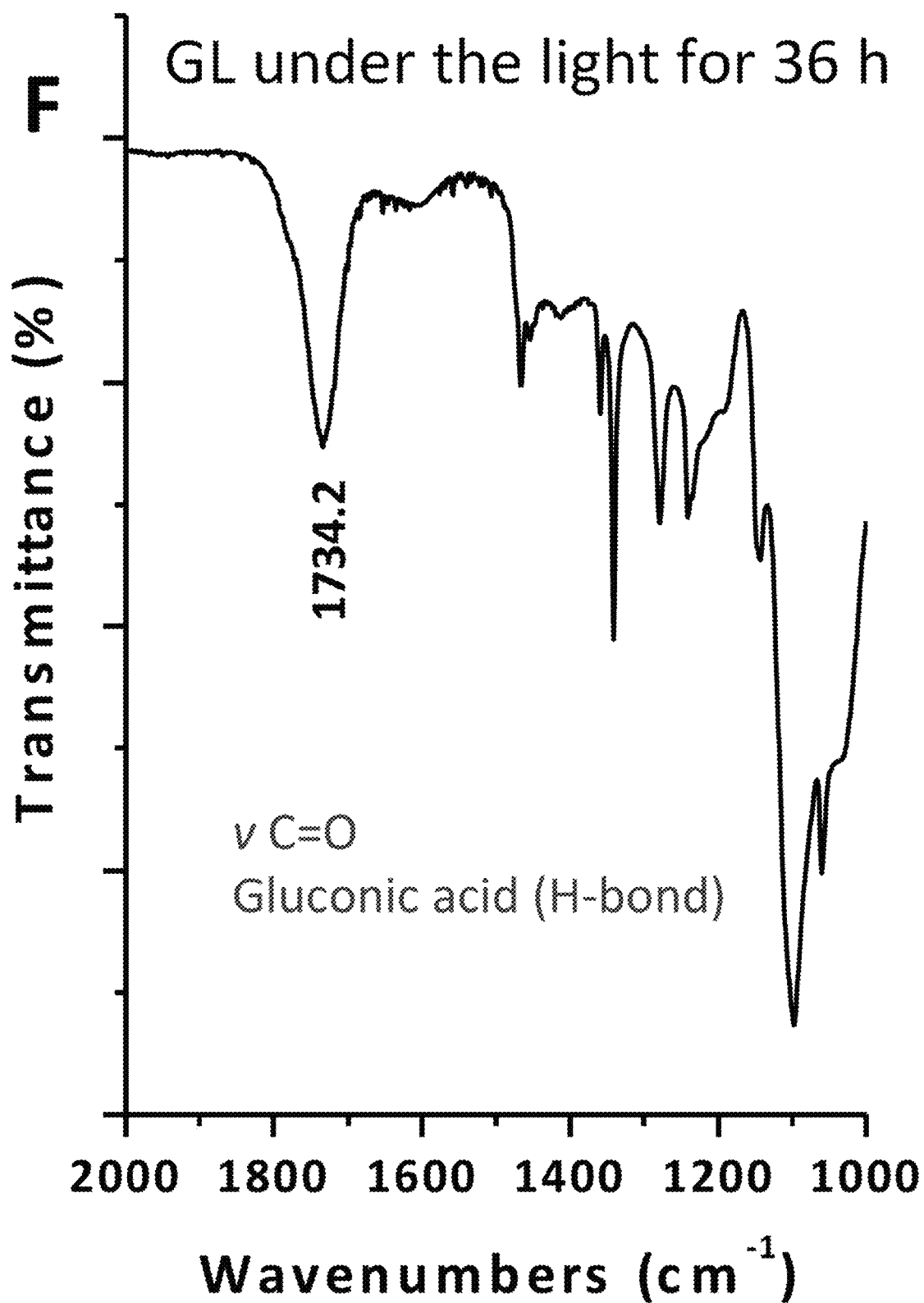
Figure 7:
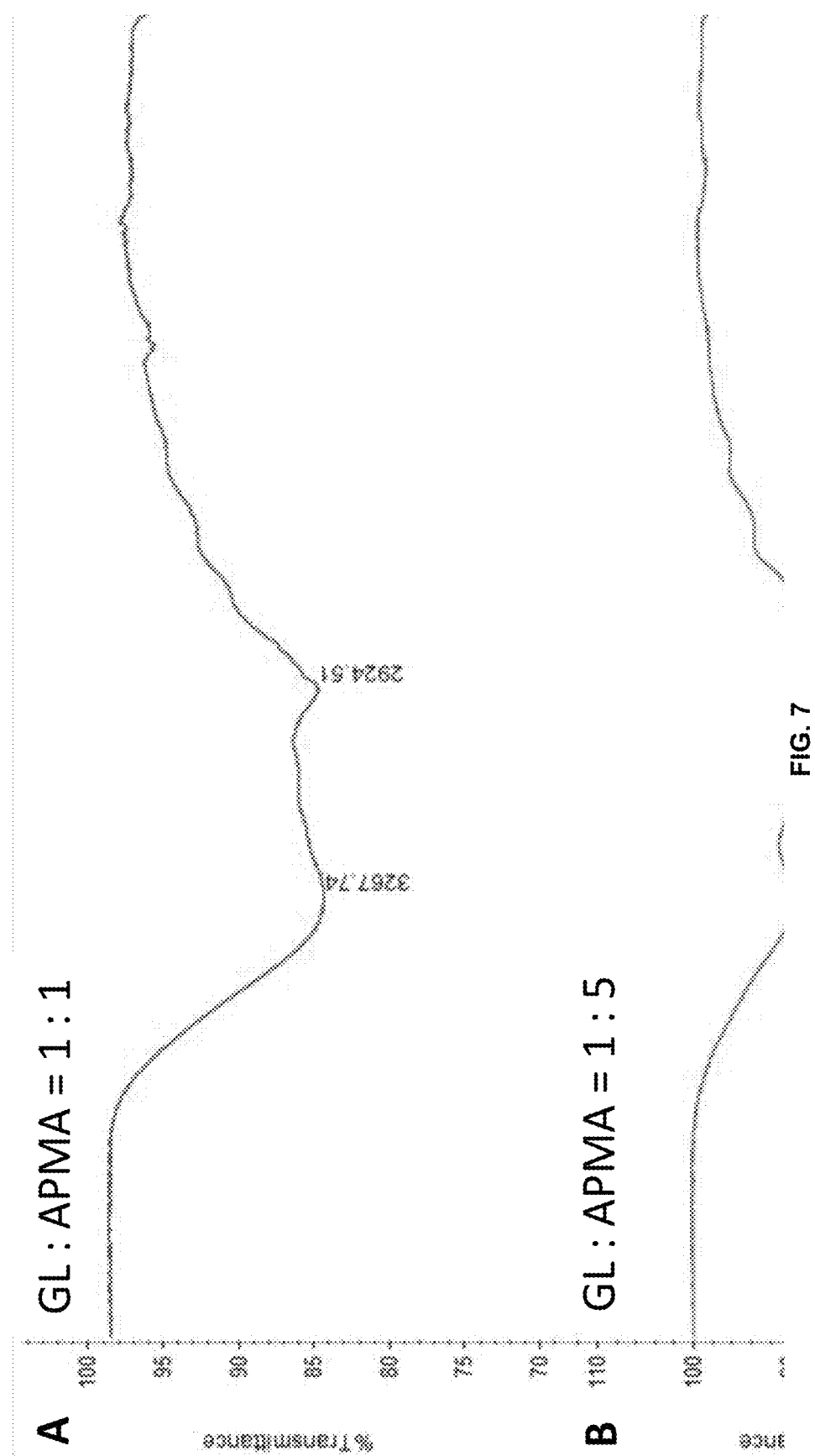
FIG. 7 depicts FT-IR spectra of GPMAA with different ratio of GL and APMA. Panel A shows 1 equiv. of APMA reacts to GL, and panel B shows 5 equiv. of APMA reacts to GL. GL is partially hydrolyzed to gluconic acid in water by equilibrium, which will instead form a charged complex with amine group of APMA. The rate of hydrolysis of GL is faster at basic pH and high temperature. Therefore, the reaction condition has to be carefully adjusted. When 1 equiv. of APMA reacts to GL, unreacted GL still remains in a form of gluconic acid, which indicates the excess APMA needs to increase yield of GPMAA. For example, the peak of gluconic acid C=O at 1734.5 $cm^{-1}$ disappears in the hydrogel by reacting it with excess APMA (5 equiv.).
Figure 8A:
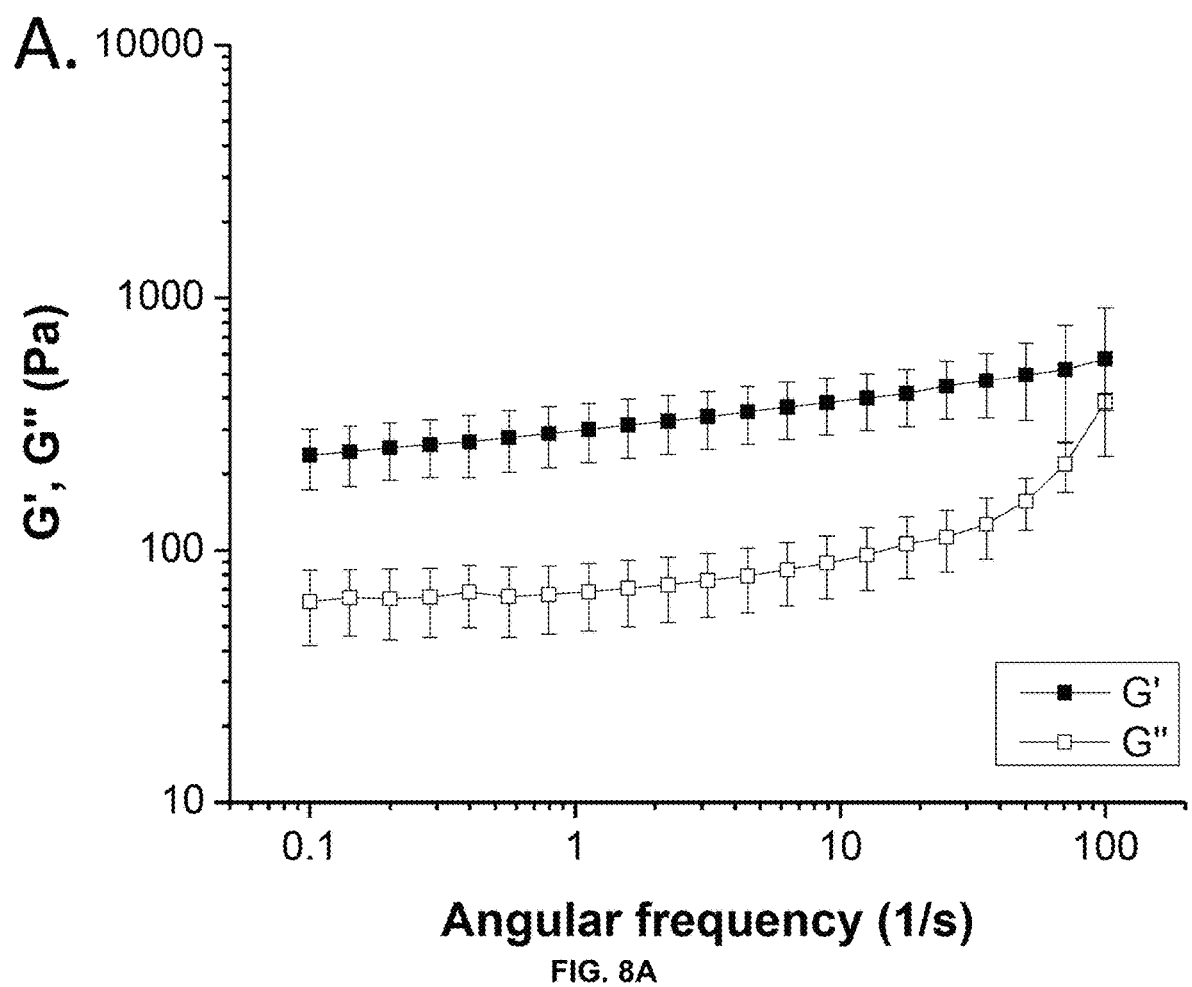
FIGS. 8A-8D depict rheology properties of GPMAA hydrogel.
Figure 8B:
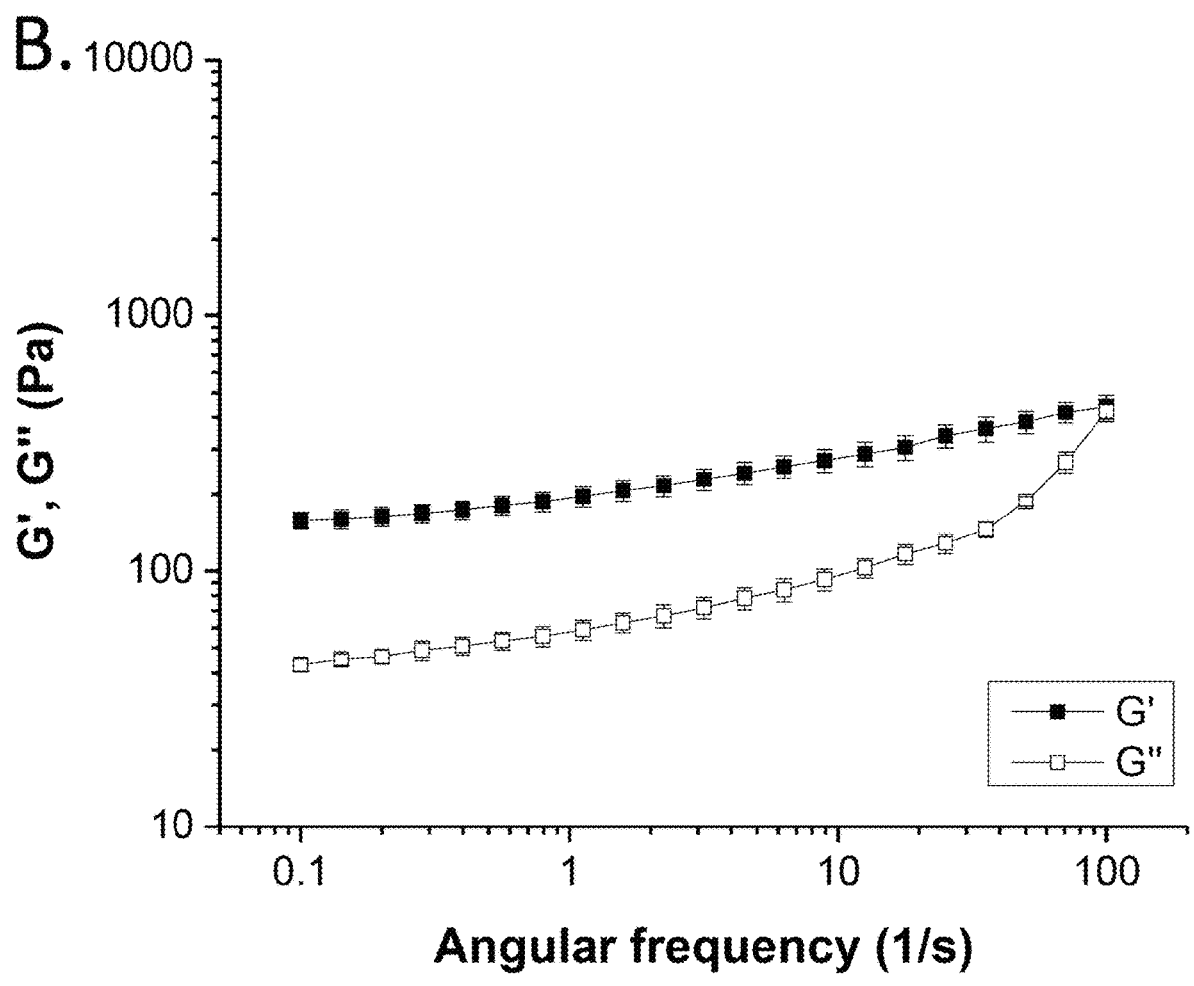
Figure 8C:
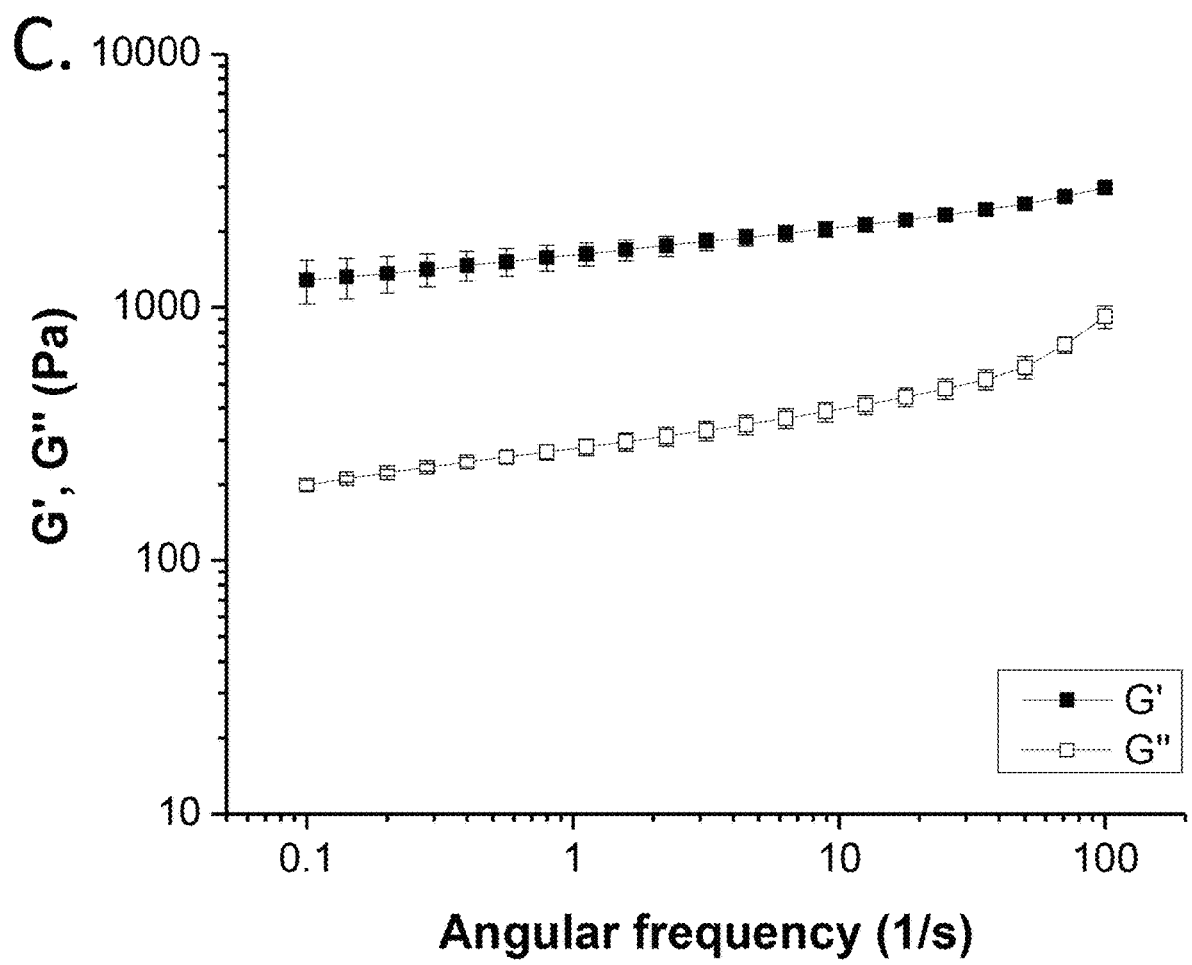
Figure 8D:
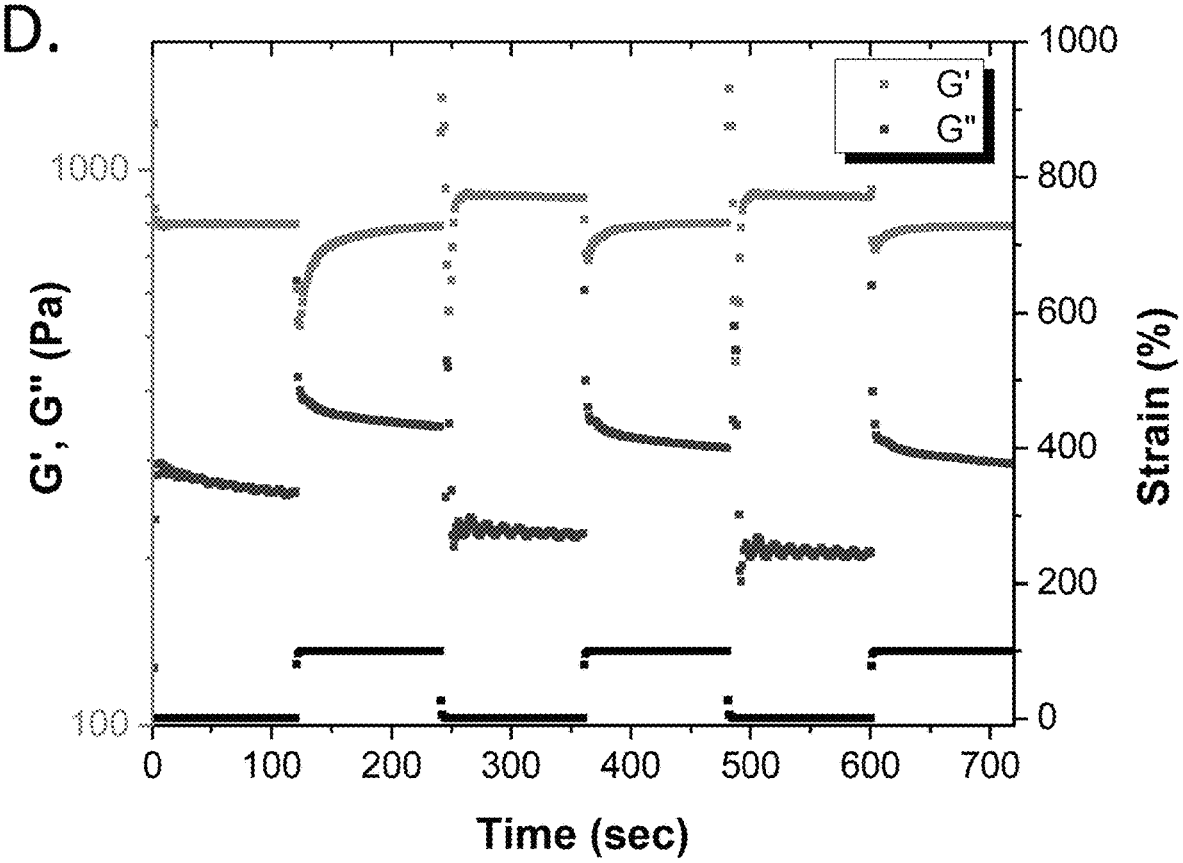
Figure 9A:
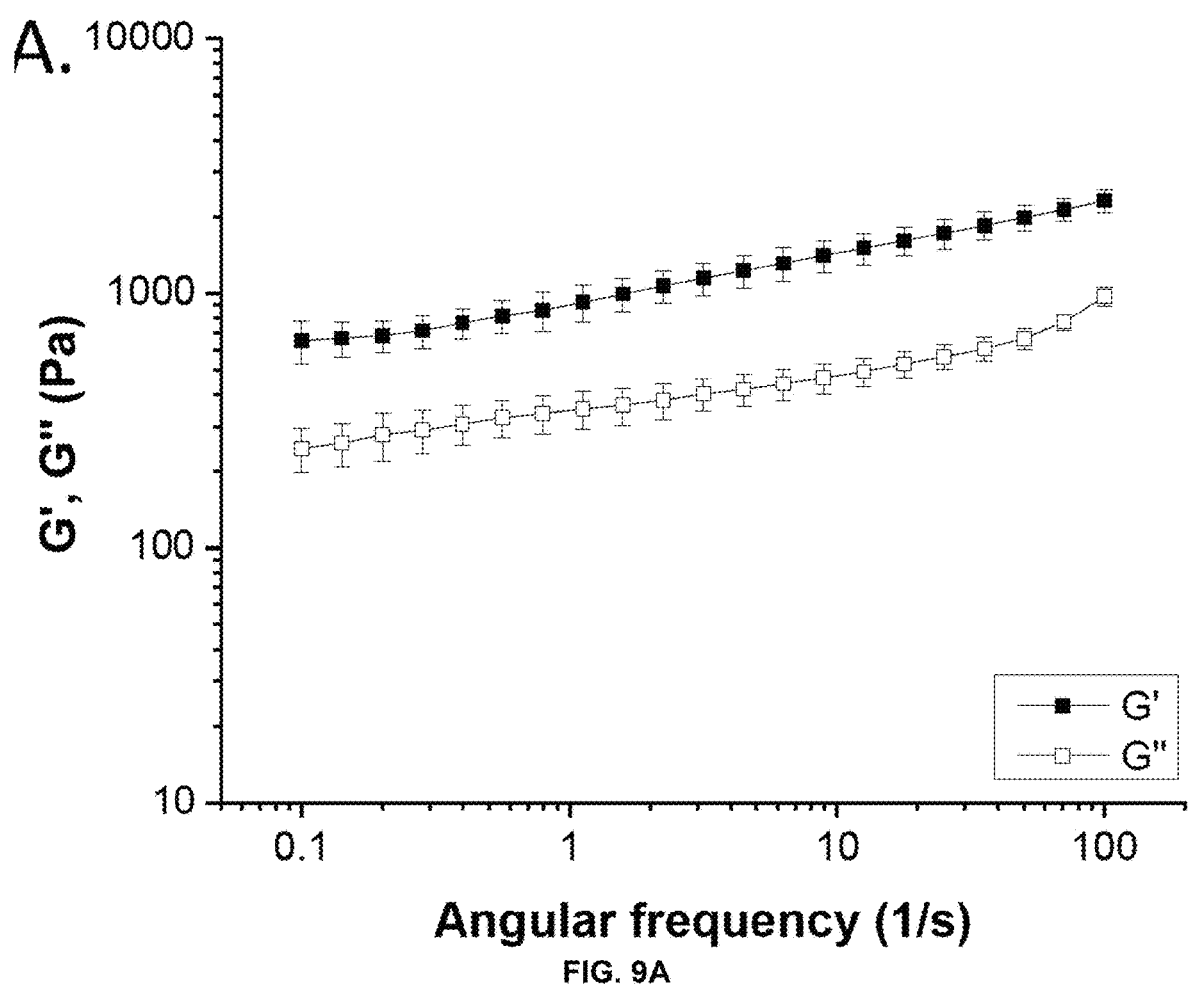
FIGS. 9A-9D show rheology property of graphene oxide-GPMAA hydrogel.
Figure 9B:
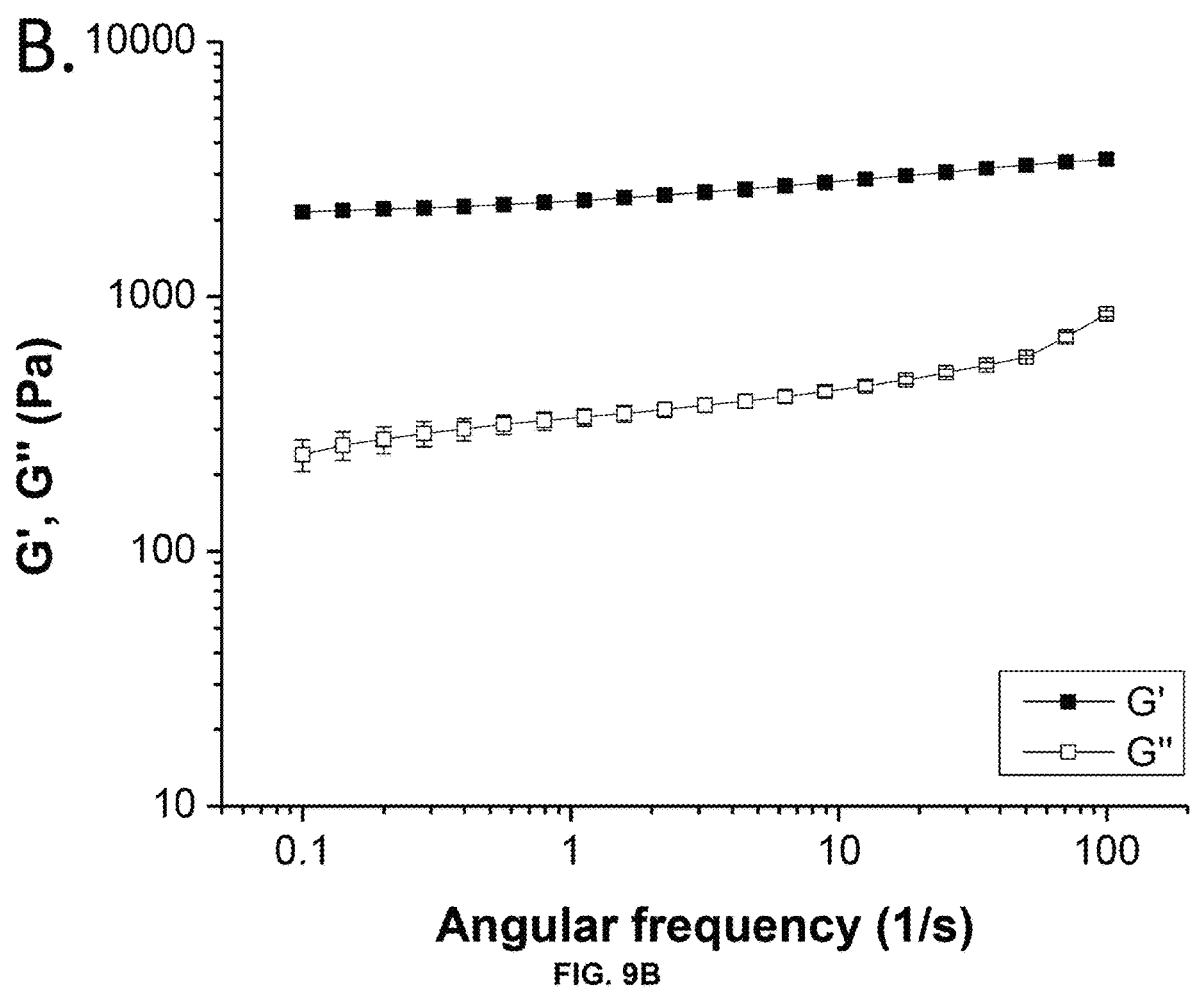
Figure 9C:
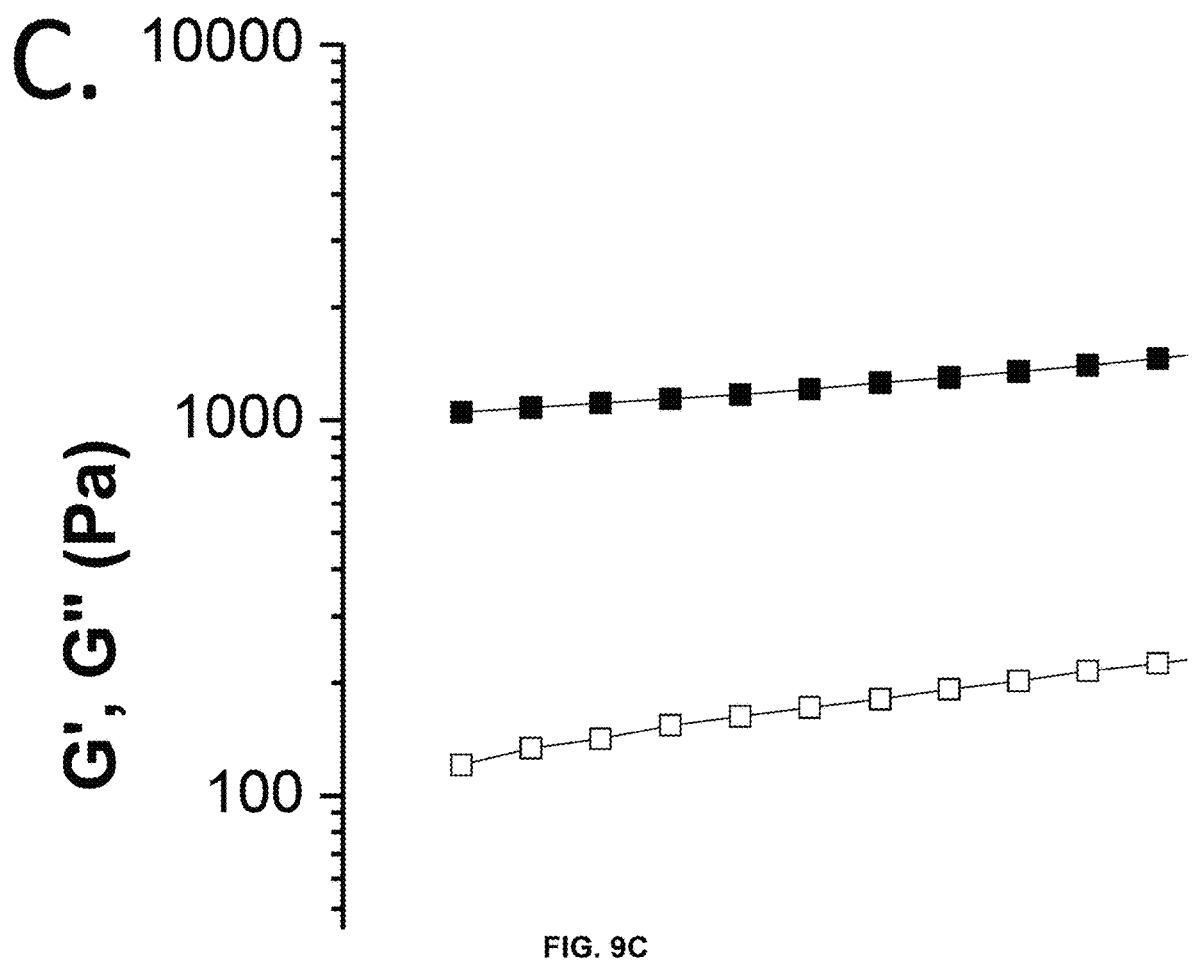
Figure 9D:
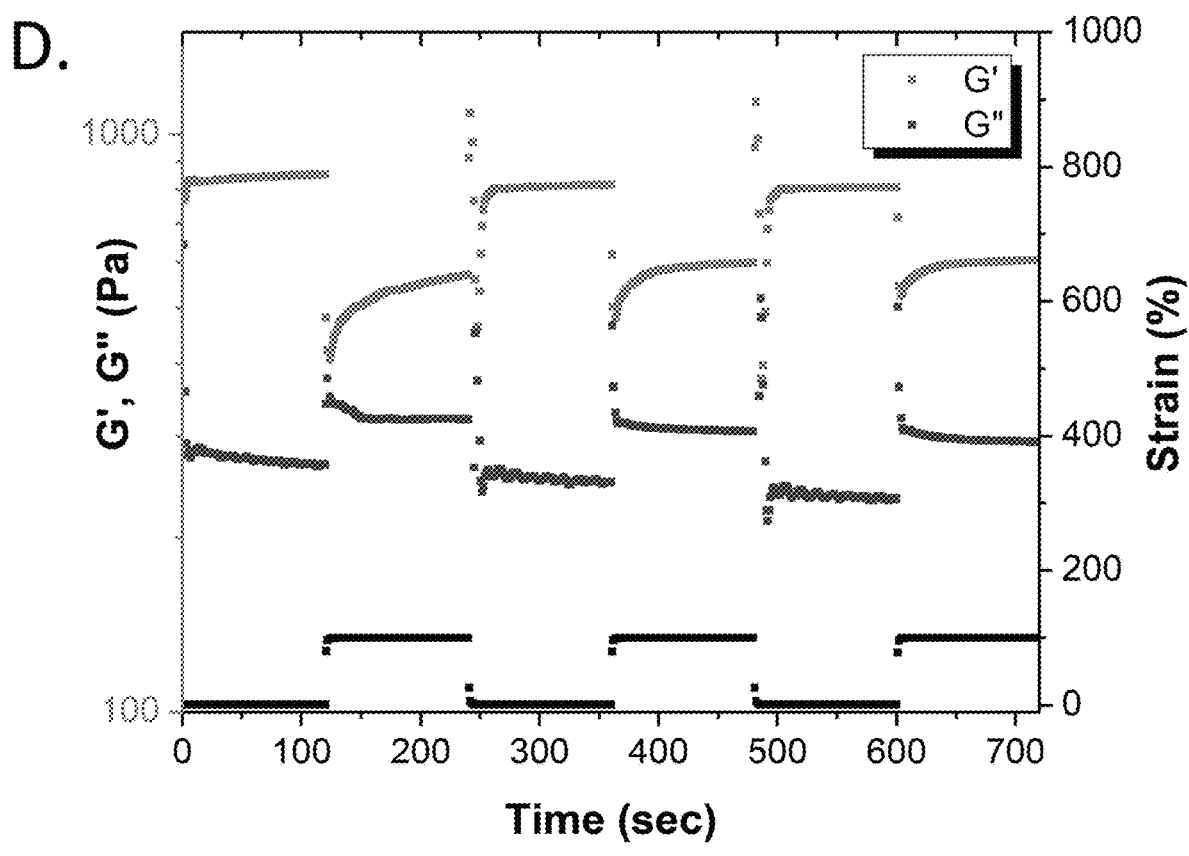
Figure 17:
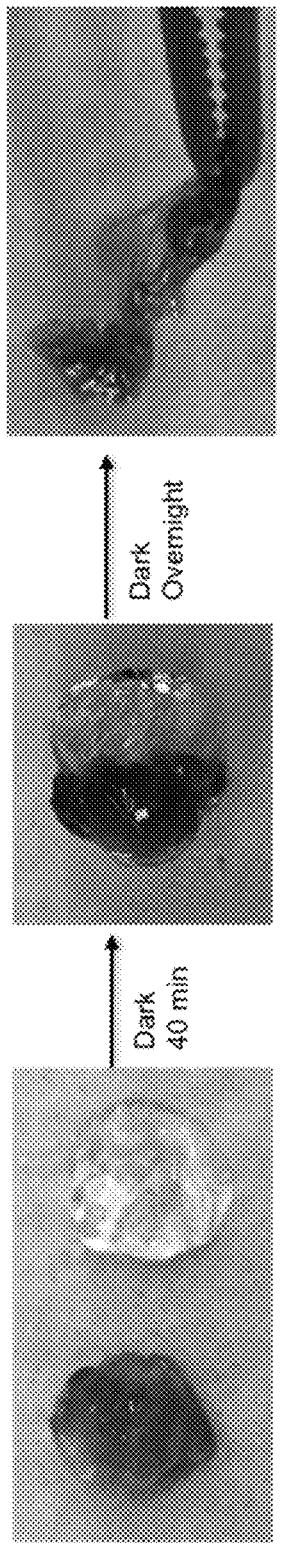
FIG. 17 depicts deformation of incomplete-self repaired hydrogel. GPMAA are dyed blue and yellow to allow for easily distinguished interface. The physically attached two hydrogels, which are kept under the dark overnight, are easily separated by deformation.

Physically separated hydrogels are able to seamlessly recombine upon light exposure (FIGS. 5A-5D). In the absence of additional GL, the hydrogel shows some repair of fissures but with some defects apparent upon mechanical deformation (FIG. 5A), suggesting that the material repair initiates from the external surface. When 5 $\mu$L of 1 M GL solution is added to the interface of two physically separated hydrogels, this results in the formation of more extensively repaired gels, which can then sustain more stringent deformation (FIG. 5B). As a negative control, the separated hydrogels placed together physically but kept in the dark overnight can be easily separated by deformation (FIG. 17). GPMAA hydrogel forms multiple hydrogen bonds with surrounding water molecules as well as inter-hydrogen bonds between the polymer chains. Hydrogen bonds are one of the common mechanisms used in self-repairing materials. Since UV-irradiation energy is directly absorbed by the glucose moiety, the formation of free radicals can be involved in acrylamide polymerization or hydrogen bonding with hydroxyl groups. Physically contacting two GPMAA hydrogels on the face restores the mechanical strength (shear stress) by nearly 50%, whereas the addition of GL and light exposure allow the restoration of the original mechanical strength (FIG. 5C). This demonstration is a mimic of chloroplast embedded-gel matrix that primarily polymerizes and crosslinks by light and continuously grows and self-repairs by the supply of glucose from the atmospheric $CO_2$ fixation (FIG. 5D). This self-healing mechanism is new and different to conventional self-healing relying on non-covalent interactions or specific chemical bonds that form or break reversibly. Glucose molecules supplied by chloroplasts repair the local damage by exceeding its own local material balance through the atmospheric $CO_2$ fixation.

In summary, a new class of carbon fixating materials grows, strengthens and self-repairs using ambient solar fluence and atmospheric carbon dioxide. This work highlights how the photosynthetic hydrogel composite systems can be optimized, including productivity and stability of extracted chloroplasts by controlling the illumination period, delivering antioxidant nanoceria inside of chloroplasts, and increasing chloroplast glucose export rate. Substantial improvement in the mechanical property can be needed for the practical use of this self-healing material. Further optimization of the carbon-fixating system and extending the lifetime of the embedded chloroplasts will invariably improve the growing rate and the repair efficiency of the material. This class of new materials will find broad utility in fields ranging from biomedicine, material construction, or defense related applications.

EXAMPLES

Isolation of Chloroplasts:

Chloroplasts isolation was performed as previously reported with a slight modification. Commercially available fresh baby spinach leaves (Spinacia oleraceae L.) were thoroughly washed with de-ionized water and the excess water was removed. After removing the middle veins, the leaves were chopped into small pieces (approximately 0.5 cm×0.5 cm) and homogenated by blending in HEPES buffer (30 mM, pH 7.6) containing polyethylene glycol (Mw. 8,000, 10% (w/v)), $K_3PO_4$ (0.5 mM), and $MgCl_2$ (2.5 mM) in an iced bath. The resulting homogenate was filtered through four layers of cheesecloth and the chloroplasts pellet was collected by centrifugation at 4,000 rpm for 15 min at 4° C. The chloroplasts were re-suspended in the aforementioned buffer and added on top of a 40% Percoll/buffer layer to separate the intact chloroplasts from the broken ones. The intact chloroplasts were sedimented as a pellet whereas the broken chloroplasts form a band in the Percoll layer by centrifugation at 1,700×g for 7 min at 4° C. The upper phases were carefully removed to collect the pellet with intact chloroplasts. This chloroplast pellet was washed with buffer to remove Percoll, and then re-suspended in buffer.

Estimation of Chlorophyll Concentration:

The yield of isolated chloroplasts is estimated by a unit chlorophyll basis (mg of chlorophyll). The chloroplast suspension is diluted by 100 times in 80% acetone and mixed well to dissolve the chloroplast membrane. This suspension is centrifuged for 2 minutes at 3,000×g and the supernatant is retained. The absorbance of the supernatant is determined at 652 nm using a Shimadzu UV-3101PC, and then multiplied by the dilution factor (100) followed by dividing by the extinction coefficient of 36 to get the mg of chlorophyll per mL of the chloroplast suspension.

$$\frac{\text{mg chlorophyll}}{\text{mL}} = \frac{A_{652}}{36} \times 100$$

Typical chlorophyll concentrations in this study were 0.90-1.14 mg $mL^{-1}$.

Isolated Chloroplasts Glucose Export:

Chloroplasts suspension (10 mL) was placed in a 6 cm-diameter glass petri dish closed with a loose glass lid to allow chloroplasts to capture light and atmospheric carbon dioxide. Chloroplasts were illuminated with a light intensity of approximately 200 µmol $m^{-2}$ $s^{-1}$ photosynthetic active radiation (40 W $m^{-2}$) using a light-emitting diode flood lamp FL-70W (LED wholesalers).

Glucose concentration is measured by hexokinase since glucose is phosphorylated by adenosine triphosphate (ATP) in the reaction catalyzed by hexokinase. Phosphorylated glucose, glucose-6-phosphate, is then oxidized to 6-phosphogluconate in the presence of oxidized nicotinamide adenine dinucleotide (NAD) in a reaction catalyzed by glucose-6-phosphate dehydrogenase. During the oxidation, an equimolar amount of NAD is reduced to NADH and consequently the absorbance at 340 nm increases, which is directly proportional to glucose concentration. Glucose (HK) assay reagent (Sigma) is prepared, which contains NAD (1.5 mM), ATP (1.0 mM), hexokinase (1.0 U $mL^{-1}$), and glucose-6-phosphate dehydrogenase (1.0 U $mL^{-1}$) with preservatives such as sodium benzoate and potassium sorbate. One U is defined as the amount that catalyzes the conversion of 1 micromole of substrate per minute under standard conditions. Glucose solutions in different concentrations are prepared to obtain a standard curve based on the absorbance at 340 nm. Reaction is carried out for 15 minutes at room temperature. The blank accounts for the contribution to the absorbance of the sample and the assay reagents.

$$\mu\text{g glucose mL}^{-1} = \frac{\Delta A \cdot TV \cdot Mw \cdot F}{\varepsilon \cdot d \cdot SV},$$

where $\Delta A$ is difference in absorbance between the sample and the blank, TV is total assay volume (mL), SV is sample volume (mL), Mw is a molecular weight of glucose 180.2 g $mol^{-1}$, F is dilution factor, $\varepsilon$ is extinction coefficient for NADH at 340 nm (mL $\mu M^{-1}$ $cm^{-1}$), and d is light path 1 (cm).

The initial glucose concentration from isolated chloroplasts within one hour is determined to be on average approximately 130 µg $mg^{-1}$. This value is attributed to previously stored starch inside the chloroplasts and is therefore subtracted to exclusively study glucose export from photosynthesis in isolated chloroplasts. Accordingly, concentration is shown in negative value when glucose influx is higher than glucose export. Although chlorophyll concentration of chloroplast suspension is maintained at approximately 0.1 mg $mL^{-1}$ throughout all experiments, control experiment were performed each time to account for batch-to-batch variability in functioning chloroplasts from each extraction round. The amount of sugar molecules exported from isolated chloroplast has been reported as an accumulated quantity within the first few hours from extraction. Glucose concentration measured for 8 h because physical damage in the chloroplast membrane starts being observed after 8 h of incubation at room temperature.

Measurement of Gluconolactone:

Gluconolactone centration measurement was performed by assay kit (Megazyme Inc., Ireland) and followed the procedure. Gluconolacone (GL) is hydrolyzed in sodium hydroxide solution (2 M, pH 11) at room temperature for 10 min. The resulting gluconic acid is phosphorylated to gluconate-6-phosphate by gluconate kinase and ATP. Gluconate-6-phosphate is converted to ribulose-5-phosphate by 6-phosphogluconate dehydrogenase (6-PDGH) in the presence of nicotinamide-adenine dinucleotide phosphate ($NADP^+$). The absorbance at 340 nm was measured, which is increased by the amount of reduced nicotinamide-adenine dinucleotide phosphate (NADPH) formed in this reaction that is stoichiometric with the amount of gluconic acid. Reaction is carried out for 6 minutes at room temperature.

The blank takes into account the contribution to the absorbance of the sample and the assay reagents.

$$\mu g\ GL\ mL^{-1} = \frac{\Delta A \cdot TV \cdot Mw \cdot F}{\varepsilon \cdot d \cdot SV},$$

where $\Delta A$ is difference in absorbance between the sample and the blank, TV is total assay volume (mL), SV is sample volume (mL), Mw is a molecular weight of gluconolacone 178.1 g/moL, F is dilution factor, $\varepsilon$ is extinction coefficient 6300 for NADPH at 340 nm (L mol$^{-1}$ cm$^{-1}$), and d is light path 1 (cm).

Nanoceria Synthesis:

Poly (acrylic acid)-coated nanoceria was synthesized by Asati et al. with some modifications. Cerium (III) nitrate (1 M, 2.5 mL, Sigma Aldrich) and an aqueous solution of poly(acrylic acid) (Mw 1,800, 0.5 M, 2.5 mL, Sigma Aldrich) were added dropwise to HEPBS buffer (0.4 M, 12.5 mL, Sigma Aldrich). The resulting mixture was adjusted to pH 8.5 with NaOH (8 M) and the reaction was continued for 1 day at room temperature under magnetic stirring. The supernatant was collected, concentrated and purified by centrifugation at 4,000 RCF for 10 min using a 10K Amicon centrifugal filter (Millipore Inc.).

Hydrogel Synthesis:

Gluconolactone (GL) solution was mixed with 3-aminopropyl methacrylamide (APMA) solution in phosphate buffer (pH 7.0) or chloroplast buffer (pH 7.6), and the mixture was placed under the ambient light for overnight at room temperature. GL (1 M) and APMA (1 M) solution were used for in vitro synthesis for characterization. This mixture (70 μL) of GL and APMA was placed on the glass slide and kept under the light in the air after 40 min UV-irradiation at 365 nm (4 W (J s$^{-1}$), 5.5 cm distance). (UVGL-15, Ultra-Violet Products Let. CA, USA)

Measurement of Hydrogel Swelling Property:

Dry hydrogel (80-120 mg) was immersed in 50 mL of deionized water for 48 h at room temperature. After swelling, the hydrogel was sediment to separate the insoluble part. The selling was calculated as follows $$Swelling = \frac{W_s - W_d}{W_d}$$

where, $W_s$ is the weight of hydrogel in swollen state and $W_d$ is the weight of hydrogel in dry state.

Evaluation of Rheological Properties:

Rheological properties of the hydrogels were characterized using Anton Paar MCR-301 rheometer (Anton Paar, Ashlanad, Va., USA) operating under disposable parallel plate geometry (10 nm diameter) at room temperature. Dynamic strain sweep (0.1-100% strain at constant 10 rad s$^{-1}$) was conducted to verify the linear viscoelastic regime, and then carry out frequency sweeps between 0.1 and 100 rad s$^{-1}$ at constant 1% strain. Hydrogels are swollen in 100 wt % DI water for 30 min, then loaded onto a sand paper (Grit:P80, Norton Abrasives, Worcester, Mass., USA) to avoid slipping. All measurements were run in triplicate and the results are expressed as the average with standard errors.

Evaluation of Mechanical Property:

The mechanical property of the hydrogel was evaluated using 8848 MicroTester (Instron Corp. Mass., USA), where two hydrogels physically contacted to each other was pulled apart by shear stress at the rate of 0.04 mm s$^{-1}$. Two hydrogels were separately formed on each glass slide (15×15×0.5 mm). As partially formed hydrogels were physically contacted on the face, the hydrogel continued to polymerize and crosslink, resulting in one merged hydrogel between glass slides. The hydrogel was clamped via sticky tape that tightly glued to the glass slide. The repairing test was carried out in a similar way. Two complete hydrogels were physically contacted on the face, and then mechanical force was applied or they were kept under the illumination after adding GL to the hydrogel interface.

Estimation of Glucose Concentration Near Chloroplast Membrane.

Approximately one chloroplast per 100 μm$^3$ ($V_1$) is observed in the microscope images with 0.1 mg Chl mL$^{-1}$ chloroplast suspension. When the mean concentration of glucose measured in the medium is 5 μM h$^{-1}$, assuming a chloroplasts as a spherical organelle, the concentration of the exported glucose molecules within a 100 nm distance (x) in a 0.01 ms (t) period (t≈x$^2$/2D), where glucose diffusion coefficient (D) is 5×10$^{-6}$ cm$^2$ s$^{-1}$ in water at 25° C.; $V_2$=4/3π(0.1)$^3$=4×10$^{-3}$ m$^3$) is 2.5×10$^4$ times as concentrated as the mean glucose concentration in the medium, and is therefore estimated to be 125 mM h$^{-1}$.

Preparation of Hydrogel Using Chloroplasts on the Graphene Oxide Film:

GOx (20 U mL$^{-1}$) was mixed with graphene oxide solution (0.1 mg mL$^{-1}$, Graphene Supermarket, NY) for 1 h at room temperature. This mixture is deposited on the amine-functionalized glass slides for 2 h at room temperature, followed by gentle washing with PBS (×3. Freshly isolated chloroplasts are pre-incubated with nanoceria for 3 h at 4° C., and the remained nanoceria was removed by centrifugation at 4000 rpm for 5 min. The resulting chloroplasts were re-suspended (0.1 mg mL$^{-1}$) in 0.1% APMA containing buffer, and then added on GOx immobilized graphene oxide film, and incubated under the ambient light for 18 h.

Characterization of Hydrogel (FT-IR Spectroscopy):

Characteristic peaks of functional groups were confirmed by Fourier transform infrared (FT-IR) spectroscopy (Thermo Electron Co. WI, USA).

Characterization of Hydrogel within Chloroplasts Suspension (FT-IR Spectroscopy):

Characteristic peaks of functional groups were confirmed by FT-IR spectroscopy (FTIR6700 Thermo Fisher Continuum FT-IR microscope). FT-IR spectra were collected from spot size 100×100 μm.

Characterization of Hydrogel within Chloroplasts Suspension (Raman Spectroscopy mapping):

Raman spectroscopy maps were collected in a confocal Raman spectrometer HR-800 (Horiba BY) using a 632 nm laser source with a 100× objective.

A Hertzian model can describe the measured force curve:

$$F = \left(\frac{3}{4}E_{eff}\sqrt{R}\right)h^{3/2},$$

where F is the applied force, $E_{eff}$ is the effective Young's modulus that can be obtained with the following relation:

$$\frac{1}{E_{eff}} = \frac{1-\vartheta^2}{E} + \frac{1-\vartheta_i^2}{E_i},$$

where $\vartheta$ is the Poisson ratio (assumed to be 0.5 for the gel). Subindex i corresponds to the mechanical properties of the AFM probe ($SiO_2$ E!=76 GPa, $\vartheta_i$=0.17). R corresponds to the tip radius: the sharp probes were modelled as cones with 7 nm base radius with 7° half-angle (Olympus, AC240TS), and the colloidal probes as 10 m spheres (Novascan Technologies, Inc., PT.PS.SN. 10). The analysis was performed in Asylum Research software with prior inverse optical lever sensitivity and tip's spring constant calibrations.

Glucose concentration exported from extracted spinach chloroplasts was measured using the microfluidic chip to verify (crosscheck) the system. Isolated chloroplasts (130 μg/ml) were placed in a microfluidic chamber with a microsieve and left in the dark. Every hour chloroplasts were washed with equal amounts of fresh buffer, while the produced glucose was carefully collected at the outlet. Extracted glucose was measured using a pre-calibrated cytochrome c (cyt c)/GOx spots. Experiments were performed in triplicates. Chlorophyll content was found to be 5 μg/ml in extracted solution, proving successful chloroplast retention inside the microfluidic chip.

Microfluidic Fabrication:

The 2-layered microfluidic chip was fabricated in PDMS.[69] Briefly, the bottom layer (100 m thickness) was formed by spin-coating PDMS at 500 rpm for 40 s. This layer contained microfluidic channels, a 5×10 mm² chamber for chloroplasts, and 5 μm microsieves to prevent chloroplasts from moving out during washing. The top layer (5 mm thickness) had similar structure except microsieves.

Glucose Sensor Fabrication:

Cyt c/GOx sensing spots were fabricated according to the previously developed procedure. Briefly, aqueous cyt c (4 mM) and GOx (500 U/ml) droplets were printed with a microarray printer using a 5 nL delivery-volume onto porous membranes (GSWP 220 nm, Millipore). The printed spots were cross-linked in vaporous glutaraldehyde for 1 h under 100% relative humidity and subsequently stored in water at 4° C. Glucose detection method relies on absorption changes in cyt c spectrum. To this end, absorption spectra were recorded in transmission mode under white-light illumination using 20× objective and a grating spectrometer (DU401A-BR-DD, Andor).

Figure 18:
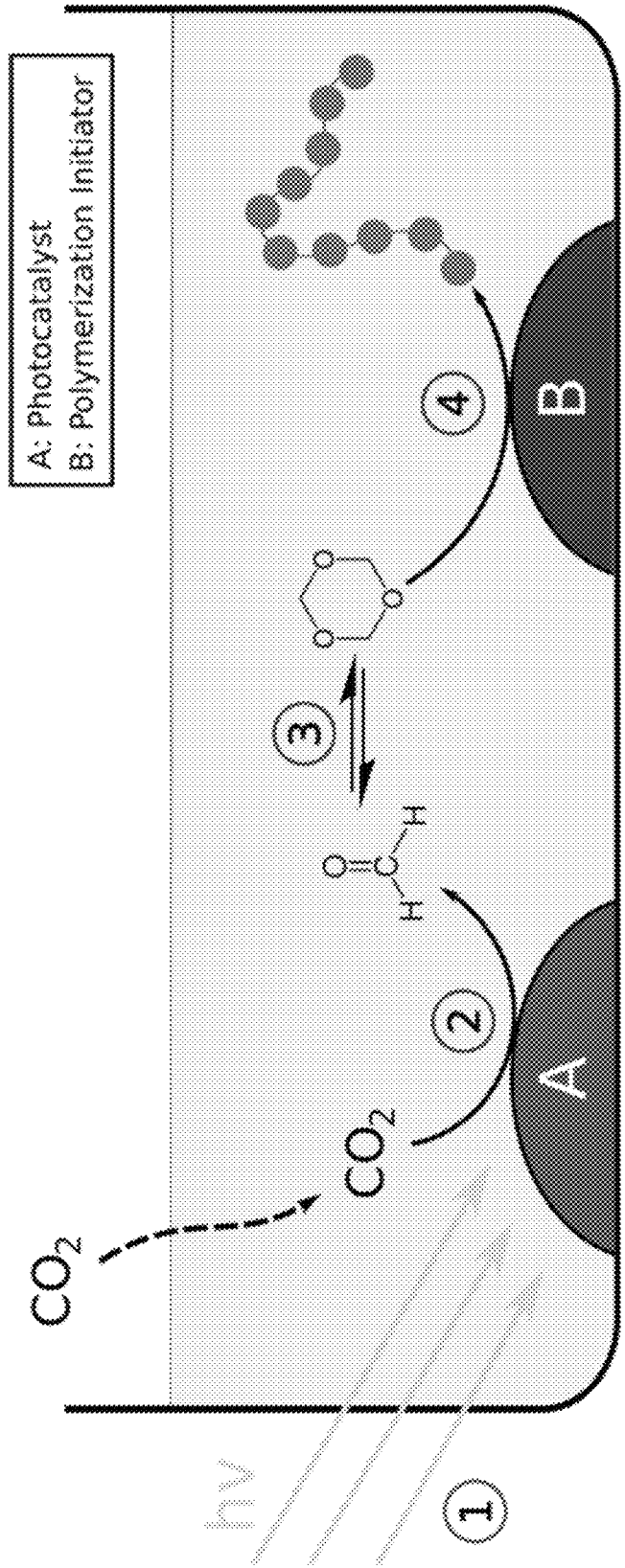
FIG. 18 depicts a schematic Illustration of System II: (1) $CO_2$ photocatalytic reduction to formaldehyde, (2) Formaldehyde trimerization to trioxane, and (3) Trioxane polymerization to polyoxymethylene (POM).

System II: Self Assembled Semiconducting Photocatalysts (Replacing the Chloroplasts) for the Direct $CO_2$ Reduction to Formaldehyde and then to Stable Polyoxymethylene The chemical mechanism of System II is demonstrated in FIG. 18. The first step involves the photoreduction of $CO_2$ to formaldehyde, which is a heterogeneous process that takes place in the solid-liquid or solid-gas interface. The atmospheric $CO_2$ (gas phase or dissolved in a solution) is converted to various products in presence of a photocatalyst (solid phase). The photocatalyst provides catalytic active sites for the reactants, absorbs light and generates electron-hole pairs, transport the charges to the surface, and finally transfers the electrons to the $CO_2$ for reduction reactions. Reduction of $CO_2$ to various products requires multiple electron transfers (listed below) to produce a wide range of products. The first electron transfer reaction to $CO_2$ presents the highest barrier to the process. The adsorption of $CO_2$ on the photocatalyst surface reduces this energy barrier and activates $CO_2$ for reduction by disrupting its linear symmetry in the adsorbed state. Simultaneously, adsorption of an electron-donor (usually water) on the photocatalyst surface consumes the holes and prevents the recombination of electron-hole; thus, providing a constant supply of electrons for the reduction reactions. The number of transferred electrons and the reaction pathways determine the $CO_2$ reduction products. The reduction mechanism is rather complicated and not fully understood to this date. Experimental data suggest that at least two branching pathways exist: (1) the formaldehyde pathway that produces formic acid, formaldehyde, methanol and methane, and (2) the carbene pathway that produces carbon monoxide, methanol, methane, and possibly ethane. In order to produce POM from $CO_2$, the formaldehyde production was maximized through the formaldehyde pathway. Minimization of the thermodynamic and kinetic barriers of the intermediate reactions and directing the reduction pathway toward production of more formaldehyde will increase both efficiency and selectivity of formaldehyde compared to other products. In the second process, formaldehyde reacts in an acidic medium to form trioxane. This process is affected by the acidity of the reaction media and the temperature. In the third process, trioxane polymerization occurs in presence of an acidic initiator. After specific amount of time, the polymer chains propagate and their concentration increases over time, yielding an increasing mass of solid product.

Figure 19:
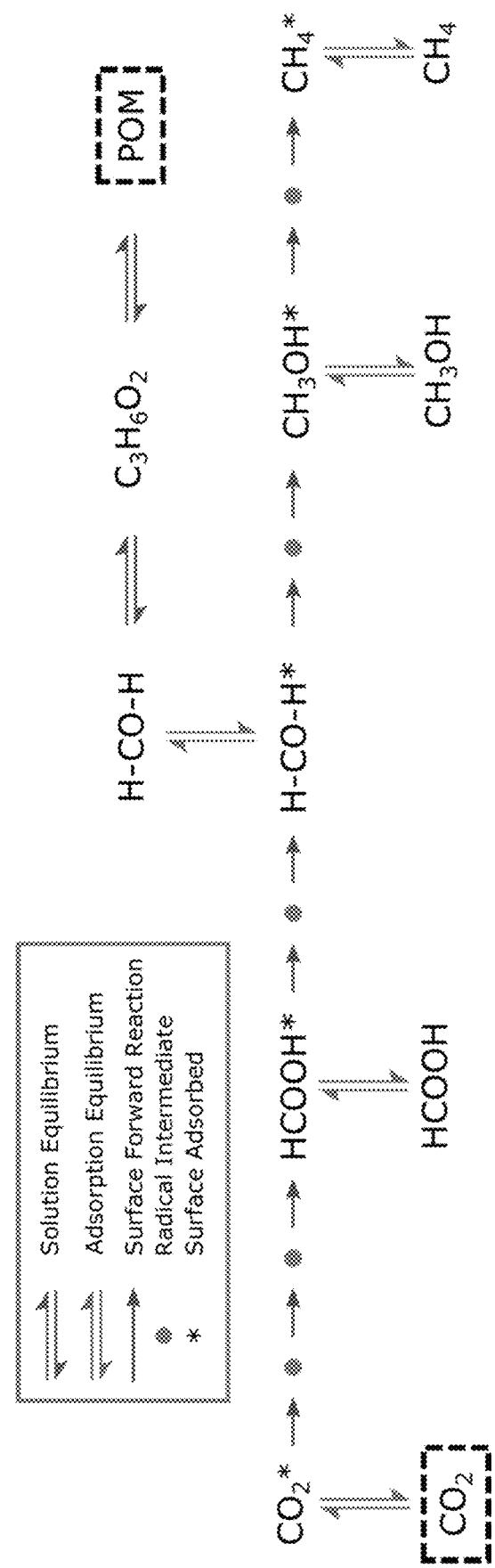
FIG. 19 depicts a proposed kinetic model for $CO_2$ System II catalytic photoreduction to HCOH and then to polyoxymethylene (POM).

In this alternative approach, three chemical processes are combined to convert $CO_2$ to polymeric product (i.e, POM): (i) $CO_2$ photoreduction to formaldehyde, (ii) Formaldehyde trimerization to form 1,3,5 Trioxane, and (iii) Trioxane polymerization to polyoxymethylene (POM). To increase the efficiency of POM production, an in-depth understanding of the chemical mechanism leading to formation of this polymer is required. A kinetic model that counts for all the reactions and phenomena leading to formation of POM shed light on the kinetic barriers of POM production from $CO_2$. FIG. 19 represents the kinetic model for $CO_2$ catalytic photoreduction.

Compartment 1: $CO_2$ Photocatalytic Reduction to Formaldehyde

Figure 20:
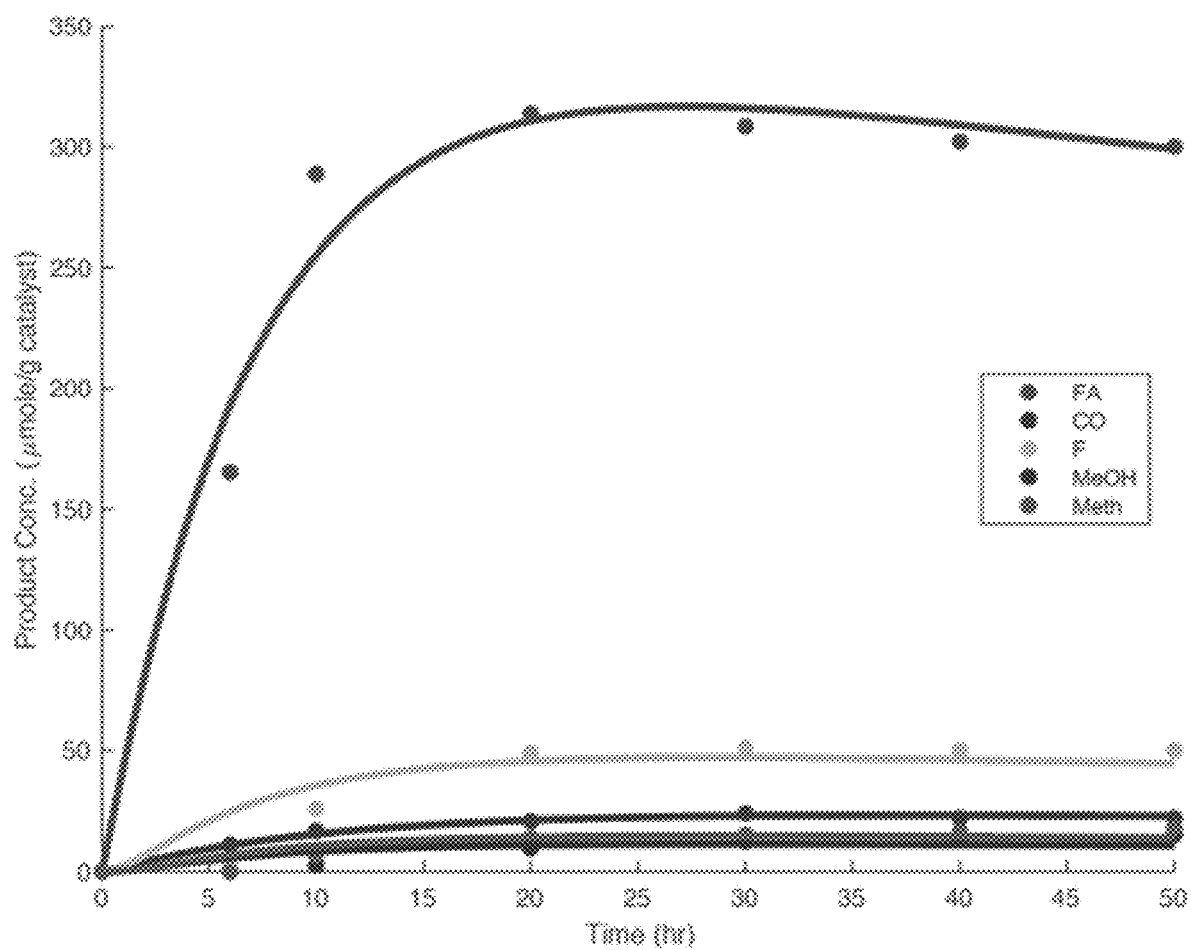
FIG. 20 depicts a time profile of the products in the catalytic photoreduction of $CO_2$: the kinetic model fitted versus experimental data of catalytic pathway products.

To achieve this overall model, a kinetic model for process (i) was developed. The $CO_2$ catalytic photoreduction is a complicated process that involves many steps including the adsorption/desorption of $CO_2$ onto the photocatalyst, electron transfer from photocatalyst to $CO_2$, a series of surface reductive reactions yielding formaldehyde as one of the products, and desorption/adsorption of the products. In the existing literature of artificial photosynthesis, usually one of these steps is considered to be the rate-limiting step and the kinetic models are developed based on only one of these phenomena. The kinetic model takes all these phenomena into account (FIG. 20).

$CO_2$ is a stable and chemically inert molecule. Reduction of $CO_2$ has a high-energy barrier and can only be performed in presence of a catalyst. Particularly, semiconductor photocatalysts can provide the energy required for the reduction of $CO_2$ by absorption of light and transferring the energy to the $CO_2$ molecules adsorbed on their surface. Formic acid, formaldehyde, methanol, methane, ethane are some of the products of the carbon dioxide photocatalytic reduction. The exact mechanism of $CO_2$ reduction on a photocatalyst surface is still unknown. The reaction pathways, the product selectivity, and yield of each reaction depends on many factors, including the choice of photocatalyst and its bandgap, reaction setup, temperature, pH, etc. So far, the studies of the reaction mechanism have suggested that the reduction of $CO_2$ occurs through a series of single-electron transfer reactions to the $CO_2$. Each of these reactions involves reduction of $CO_2$ by transferring one electron from the surface of catalysts and H+ from the surrounding media to yield radical intermediates or the main products.

The production of formaldehyde has been mainly reported in presence of $TiO_2$ as the photocatalysts. Moreover, it has been shown that the reduction of $CO_2$ in aqueous dispersions of $TiO_2$ lowers the energy barrier of the first electron-transfer reaction step and $CO_2$ activation and thus, increases the product yield. In most of the reaction set ups a batch reactor with a light source and gas inlet and outlet that was used to perform the reaction. $CO_2$ is purged into the reactor until the solution is saturated with the reactant. The solubility of $CO_2$ in the liquid phase depend on the $CO_2$ partial pressure according to the Henry's law; in most studies atmospheric pressure of $CO_2$ is used to evaluate the reduction reactions. Constant stirring of the sample facilitates the adsorption of $CO_2$ on the catalyst particles and prevent the mass transport limitation in this heterogeneous catalytic system. In such a system, water is the main source of the H+. Water splitting reaction occurs simultaneously in presence of the photocatalysts and yields H+. The pH of the system plays an important role in determining the reaction pathways, the $CO_2$ can be present in various carbonate forms in the solution depending on the pH and thus, the adsorption and activation energies required to reduce these forms of dissolved $CO_2$ are different from each other.

Formic acid, formaldehyde, methanol, and methane are the main products of $CO_2$ reduction in a reaction setup described above. Exact reaction mechanism is still a matter of controversy in the current literature and minimal kinetic data reporting the production of all these products are available. Various complicated reaction networks have been suggested, some of them justifying the presence of trace amount of products in the reactor. Recent DFT studied assist with narrowing down the reaction network and investigating the most possible pathway with lowest energy barriers. The following reaction network may be best descriptive of the thermodynamically plausible pathway and is consistent with the product measurements:

$CO_2 + 2H^+ + 2e \rightarrow 4HCOOH$ $CO_2 + 2H^+ + 2e \rightarrow CO + H_2O$ $HCOOH + 2H^+ + 2e \rightarrow HCOH + H_2O$ $CO + 2H^+ + 2e \rightarrow HCOH$ $HCOH + 2H^+ + 2e \rightarrow CH_3OH$ $CH_3OH + 2H^+ + 2e \rightarrow CH_4 + H_2O$ According to this reaction network, aqueous $CO_2$ reaction with hydrogen radicals to produce formic acid, carbon monoxide, formaldehyde, methanol, and methane. Radical intermediates that are generated in single-electron transfer steps are steady-state species that are not stable and thus, cannot be measured with precision in the solution. For a comprehensive kinetic modeling of the above reaction network in a heterogeneous catalytic system, the adsorption of the reactant on the catalysts surface and desorption of products from the catalyst surface must also be taken into consideration and the surface reactions must be modeled using the surface concentration of species according to the LHHW kinetic modeling approach. However, due to the lack of kinetic data in the current literature and in attempt to avoid over-parameterizing the model, the power-law modeling approach is used to explain the reaction network using a series of individual first-order reaction:

$$\frac{d[CO_2]}{dt} = -k1[CO_2] - k[CO_2]$$

-continued $$\frac{d[HCOOH]}{dt} = k1[CO_2] - k3[HCOOH]$$

$$\frac{d[CO]}{dt} = k2[CO_2] - k4[CO]$$

$$\frac{d[HCOH]}{dt} = k3[HCOOH] + k4[CO] - k5[HCOH]$$

$$\frac{d[CH_3OH]}{dt} = k5[HCOH] - k6[CH_3OH]$$

$$\frac{d[CH_4]}{dt} = k6[CH_3OH] - k7[CH_4]$$

where t is the reaction time and k1 to k6 are the reaction rate constants for the above-mentioned reactions. The reaction rates can be found by fitting the model to the experimental kinetic data from Peng et. al. that reported the product yield for formic acid, formaldehyde, methanol and methane over time. As shown in FIG. 20, the model is highly consistent with the experimental data with minimal error. To assure the precision of the model, the confidence intervals of the fitted rate constants were calculated by perturbing the experimental data input by 5% (Table 1). The calculated rate constants are shown in the below table. The first reaction of $CO_2$ reduction to carbon monoxide and formic acid have considerably smaller rate constants due to the higher activation energy of the $CO_2$ compared to other product in the reaction chain.

Compartment 2: Formaldehyde Conversion to 1,3,5-trioxane

Production of trioxane from formaldehyde has been studied in the literature to some extent. The reaction can proceed in concentrated aqueous solution of formaldehyde and in presence of a Lewis acid as the catalyst. The reaction is known to be slow at room temperature and involves many unstable intermediates. Thus, in industrial plants the reaction is usually carried at temperatures above 100° C. The kinetic data available in the literature are usually collected at such high temperatures and thus, the rate constants for the reaction at the room temperature is unknown. Although the reaction involves many intermediates, the overall conversion of formaldehyde to trioxane can be described by the below reaction:

$$3 \text{ HCOH} \rightleftharpoons C_3H_6O_3$$

Figure 21:
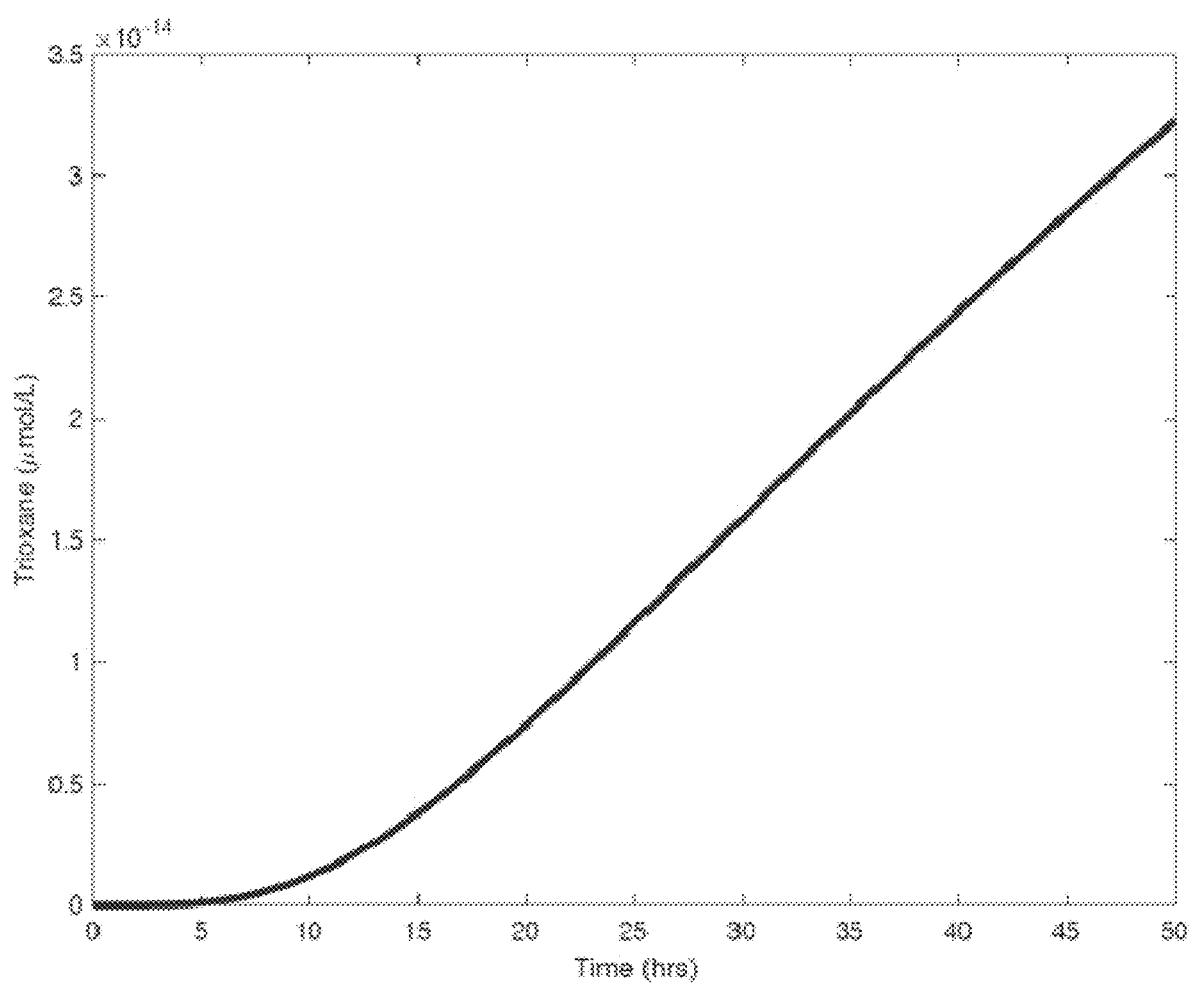
FIG. 21 depicts a time profile of the production of 1,3,5-trioxane in Compartment 2 of the proposed system from formaldehyde produced in compartment 1 by photocatalytic reduction of $CO_2$.

To estimate the rate constant of this reaction at room temperature a power-law model can be used to describe the rate of the overall reaction:

$$[\ ]\frac{d[C_3H_6O_3]}{dt} = k1[HCOH]^3 - k2[C_3H_6O_3]$$

where t is time and k1 and k2 are the reaction rate constants for the forward and the reversible reaction, respectively. The kinetic data from literature at different temperatures (360, 373, 380 K) were used to estimate the activation energy of this reaction according to the Arrhenius law and then calculate the reaction rate constant at room temperature, k1=2.31×10⁻¹² and k2=1.64×10⁻¹⁰. Using these rate constants and assuming that all the formaldehyde produced in Compartment 1 is extracted, concentrated, and transferred to Compartment 2 upon production, trioxane can be produced with minimal yield as depicted in FIG. 21. Obviously, the formaldehyde conversion to trioxane is very slow at room temperature. In order to produce considerable amount of trioxane from photocatalytically produced formaldehyde, strategies to accelerate the reaction using more efficient catalysts or temperature rise suing the light source with minimal energy input must be further investigated.

Compartment 3: Trioxane Polymerization

Moreover, a kinetic model was developed for process (iii) that explain the formation of POM from trioxane. This reaction has been studied to some extent in the literature; it is known that two phases exist for this polymerization reaction: (1) an induction period in which the trioxane reacts to produce tetraoxane and minimal polymerization occurs, and (2) the secondary phase in which the POM propagates and its production rate increases over time upon constant supply of the trioxane. While various kinetic models have been proposed for the induction period, there has not been a kinetic model reported for the secondary phase. The model takes into account the concentration of initiator and the trioxane concentration in production rate of the polymer in the secondary phase. A model was developed for process (ii) based on the experimental data for this reaction, and use these three kinetic models to develop an overall model for POM production from atmospheric $CO_2$.

Modeling of Compartmental Reactions in Systems I and II for Optimization of the Systems The overarching goal of this study is to exploit ambient solar energy harvesting and carbon dioxide reduction to create a new class of regenerative, densifying materials—a class that literally grow in $CO_2$ and sunlight. This class of materials point to several fundamental questions relating to carbon fixation and its incorporation into functional materials. By performing these reactions within material compartments, it is possible to create coatings and supports that continuously grow and self-repair using carbon dioxide as a carbon source. Such materials would significantly benefit transportation and construct costs, and exhibit self-healing and densification over time. Significant progress has been made to date on two systems.

Mathematical Modeling of Spatial and Temporal Densification Matrix in System I

Mathematical modeling of metabolism is a powerful tool for gaining sufficient understanding of complex reaction and metabolic pathways for the optimization of biologically-based system design. In the case of system I, a metabolic model of $C_3$ leaf carbon metabolism is used for the production of carbohydrates, which then be used as source terms for a spatiotemporal transport model of polymer production within the proposed chloroplast-entrapped hydrogel matrix. This type of modeling is fundamentally necessary, as the continual densification of the matrix poses growing diffusion barriers, resulting in a tapering of overall fixation rates.

Figure 22:
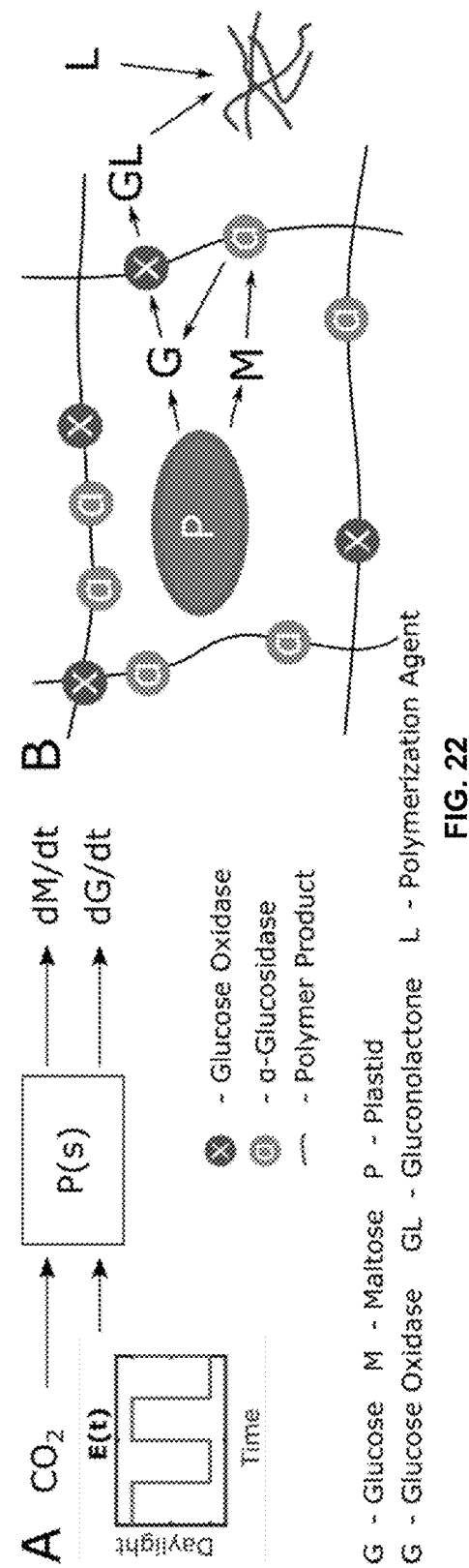
FIG. 22 depicts a schematic of the proposed transport and polymerization of glucose. Panel A shows transfer function model of sugar export of the Chloroplast. Panel B shows Intra-matrix transport and polymerization schematic

The modeling consists of two stages: (1) chloroplast carbohydrate production and export, (2) conversion and polymerization within the engineered hydrogel matrix. Pertaining to the former stage, while extensive and detailed mathematical models of $C_3$ leaf carbon metabolism exist, an experimentally based transfer function approach was taken. In the case of the plasmid chlorophyll, a transfer function with the inputs being $CO_2$ concentration and light exposure was constructed, and the outputs being the flux of maltose and glucose as a function of time (FIG. 22). As inputs and outputs can both be measured, a direct analytical solution or a neural-network based approach is employed. This function system was improved by scanning the input space experimentally by varying light exposure and $CO_2$ concentrations.

As using living systems in $CO_2$ fixation is complex, especially the plasmid based diurnal conversion and transport, successful completion of this model present a significant advance in the ability to predict and study the dynamics of utilizing chlorophylls in the manufacturing setting. This work is in optimizing the conditions of biomass densification, and potentially motivates significant improvements in scaffold design.

TABLE 1

The reaction rate constants for $CO_2$ photocatalytic reduction in presence of $TiO_2$ estimated from fitting the power-law kinetic model to experimental data and the associated errors.

| | Rate Constants (1/s) | Error within 95% confidence interval of the experimental data |
| --- | --- | --- |
| k1 | 3.31 × 10−6 | 1.60 × 10−16 |
| k2 | 1.55 × 10−7 | 3.97 × 10−14 |
| k3 | 2.46 × 10−5 | 2.18 × 10−12 |
| k4 | 1.42 × 10−5 | 2.54 × 10−12 |
| k5 | 1.67 × 10−4 | 1.25 × 10−10 |
| k6 | 6.93 × 10−4 | 2.47 × 10−9 |

More generally, production of high-energy materials from $CO_2$ with negative carbon footprint using renewable energy sources can be vital for a sustainable future.

A polymeric material that can (i) grow, (ii) densify, and (iii) self-heal over time upon exposure to sunlight and atmospheric $CO_2$ is a novel class of biomimetic materials with unique production process characteristics: minimal energy cost and negative $CO_2$ footprint. Here, a $CO_2$ fixing pathway through atmospheric $CO_2$ conversion to polyoxymethylene (POM). POM is an engineering plastic mainly used in the automotive and electronics industry for its unique chemical stability and mechanical properties was investigated. A self-healing and densifying POM composite generated from atmospheric $CO_2$ will bring new opportunities for the production of protective coatings and structural composites. This novel class of POM composites may be realized by an overall pathway featuring a compartmental catalytic system consisted of: (a) photocatalyst; (b) monomer formation catalyst; and (c) polymerization initiator exposed to atmospheric $CO_2$ and sunlight. Here, each reaction unit to identify the rate-limiting steps was kinetically modeled using available data in the literature. the key catalytic and photocatalytic key reactions necessary for maximizing the POM growth rate can be identified. Further, the maximization of POM growth rate though reaction engineering strategies and enhancing the carbon adsorption capacity was investigated. Finally, the regimes of reaction kinetics and $CO_2$ adsorption capacity which deliver the desired and maximized POM growth rate can be determined.

The chloroplast in plants uses the solar energy to fix atmospheric $CO_2$ into glucose (and other form of sugars). Further polymerization of glucose yields biomass in form of cellulose, starch, etc. Artificial photosynthesis, is focused on mimicking the first half of plants function by reducing $CO_2$ to hydrocarbons and fuels, utilizing solar energy with the aid of photocatalysts. Like in plants, the $CO_2$ reduction reaction is accompanied by water splitting reactions on the photocatalyst surface to provide the electrons required for the $CO_2$ reduction reactions. However, the low $CO_2$ conversion rates and poor yield and selectivity of products necessitates the experiments to be carried under higher $CO_2$ pressures (usually 1 atm of pure $CO_2$), even for the most successful artificial systems. The conversion of actual atmospheric $CO_2$ with a partial pressure of 400 ppm is one element of artificial photosynthesis missing in current research efforts. Another missing element in artificial photosynthesis is mimicking the second half of the plants function in polymerizing the elementary $CO_2$ reduction products to higher-energy, more complex structures that can grow and densify over time.

A polymeric macromolecule that can (i) grow, (ii) densify, and (iii) self-heal over time upon exposure to sunlight and atmospheric $CO_2$ is a novel class of materials that may be recognized by its main production process characteristics: minimal energy cost and negative $CO_2$ emission fingerprint. Using renewable energy source, abundant reactants, earth-abundant photocatalysts (such as graphitic carbon nitride) make this product more economic and simultaneously eco-friendly. Thus, this production strategy brings new opportunities in chemical production industry, structural composites, and protective coatings. Moreover, the minimum energy and transportation cost of this process make it economically more competent among the state of the art thermo- and electro-chemical reduction processes for $CO_2$.

Devising a reaction pathway consisting of two catalytic compartments for (i) photocatalytic conversion of atmospheric $CO_2$ to elementary products and (ii) polymerization of $CO_2$ reduction products is the first step toward realizing this novel class of materials. Extracted chloroplast can be coupled with a secondary polymerization chemistry to produce self-healing polymeric materials only using atmospheric $CO_2$ and light as energy source. However, the $CO_2$ reduction to glucose is restricting (the mechanism of $CO_2$ reduction by chloroplast always yields glucose as the starting point for the final product).

Replacement of chloroplast with photocatalyst expands the number of feasible pathways toward novel polymeric product because it yields multiple $CO_2$ reduction elementary products such as formic acid, formaldehyde, carbon monoxide, methanol, and methane. Additionally, coupling the photocatalytic compartment with the secondary polymerization compartment can extend the life time of the catalytic system, avoiding concerns such as chloroplast short life span or damage upon exposure to harsh atmosphere. However, the low conversion rate of $CO_2$ in photocatalytic systems (~few micromole/hr of products) is a challenge that will affect the yield and growth rate of final polymeric product. Hence, any proposed pathway from atmospheric $CO_2$ to a polymeric product must be evaluated for their thermodynamic feasibility and kinetics of reaction.

Figure 23:
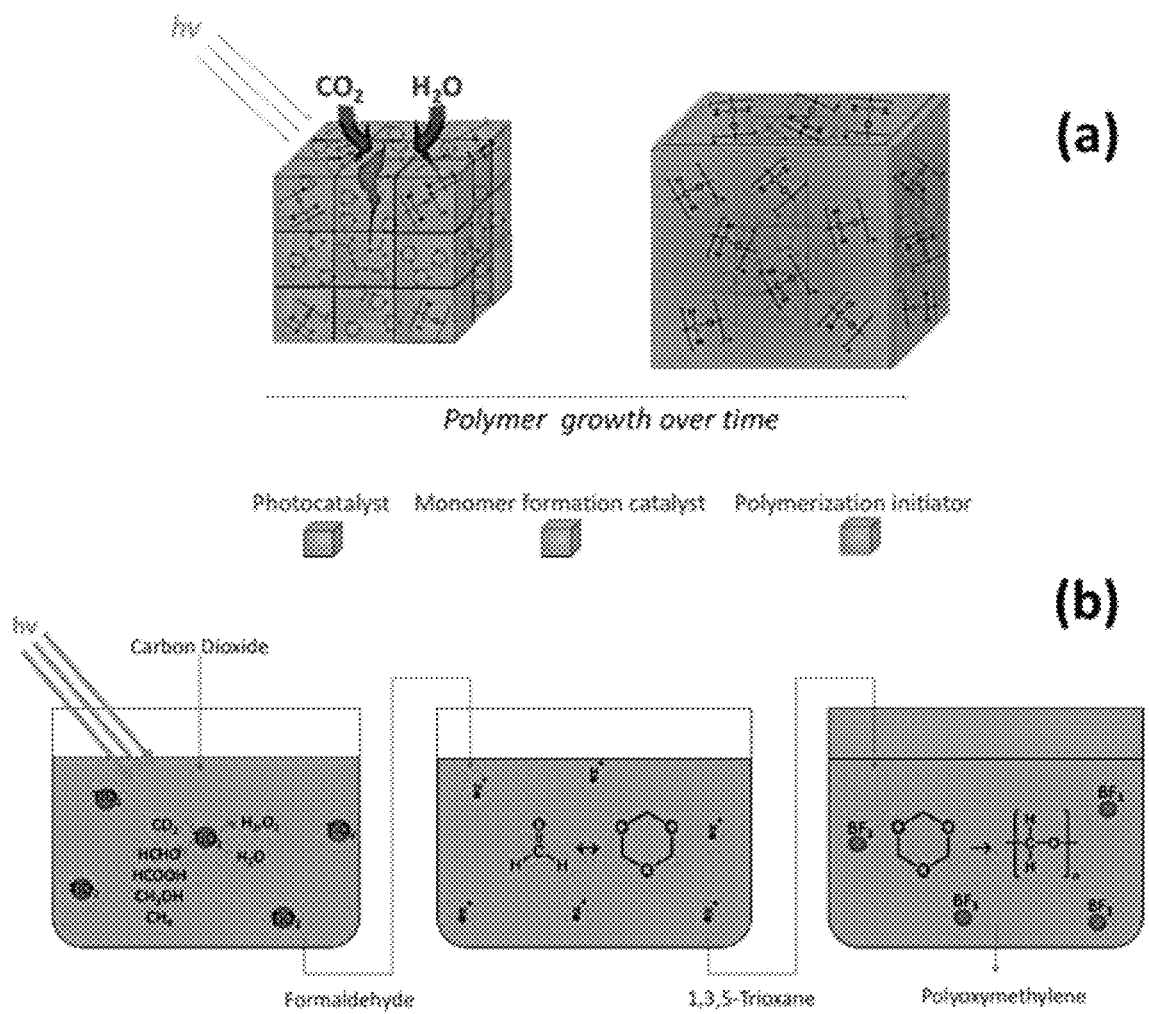
FIG. 23 depicts the novel carbon-fixing polyoxymethylene composite may be realized by an overall pathway featuring a compartmental catalytic system consisted of: (panel a) photocatalyst; monomer formation catalyst; and polymerization initiator exposed to atmospheric $CO_2$ and sunlight. Panel b shows the full chemical pathway consists of three steps: RXN 1: $CO_2$ photocatalytic reduction to formaldehyde, RXN 2: Formaldehyde conversion to 1,3,5-trioxane, RXN 3: Trioxane polymerization to POM.

Here, a thermodynamically feasible pathway from $CO_2$ to polyoxymethylene (POM) using kinetic engineering was evaluated. This pathway consists of two main reactions: (i) photocatalytic reduction of atmospheric $CO_2$ to formaldehyde and (ii) catalytic polymerization of formaldehyde to POM. POM contains repeating units of oxymethylene (—O—$CH_2$—) and is produced industrially by polymerization of 1,3,5-trioxane ($C_3H_6O_3$), a stable cyclic trimer of formaldehyde. Therefore, a full chemical pathway consists of three main compartments (FIG. 23): (1) $CO_2$ reduction to formaldehyde, (2) formaldehyde conversion to 1,3,5-trioxane, and (3) trioxane polymerization to POM.

For each step, a reaction mechanism based on the data previously reported in the literature and use the kinetic data to obtain the reaction rate constants in each step was proposed. Next, the reactions from each step were integrated into an overall reaction pathway from $CO_2$ to POM to evaluate the kinetics of the process. The POM yield and growth rate are calculated and used to determine rate limiting steps of the proposed pathways. Also, the required relative improvement of the kinetics of industrial process for obtaining plausible POM growth rates are calculated. Combining this compartmental catalytic system with $CO_2$ capturing technology is discussed in order to provide a roadmap for the efforts focused on kinetics improvement and enhancement of $CO_2$ adsorption.

This specific pathway is a case study to obtain further insight toward the overall strategy of production of macromolecular products from atmospheric $CO_2$. Certainly, other chemical pathways may be proposed and their thermodynamic and kinetic feasibility can be investigated in future. Pathways from formic acid, formaldehyde and methanol toward ethylene, acrylic acid, and simple sugars are among the feasible overall compartmental catalytic systems that can serve as building blocks for high-energy polymeric materials.

Analysis and Discussion:

In the following sections, the reaction pathway proposed for each compartment, kinetic models fitted to the experimental data available in the literature, and estimated/calculated reaction rate constants at 25-30° C. for all three compartments is presented.

RXN1: Photocatalytic Reduction of $CO_2$ to Formaldehyde.

Figure 24A:
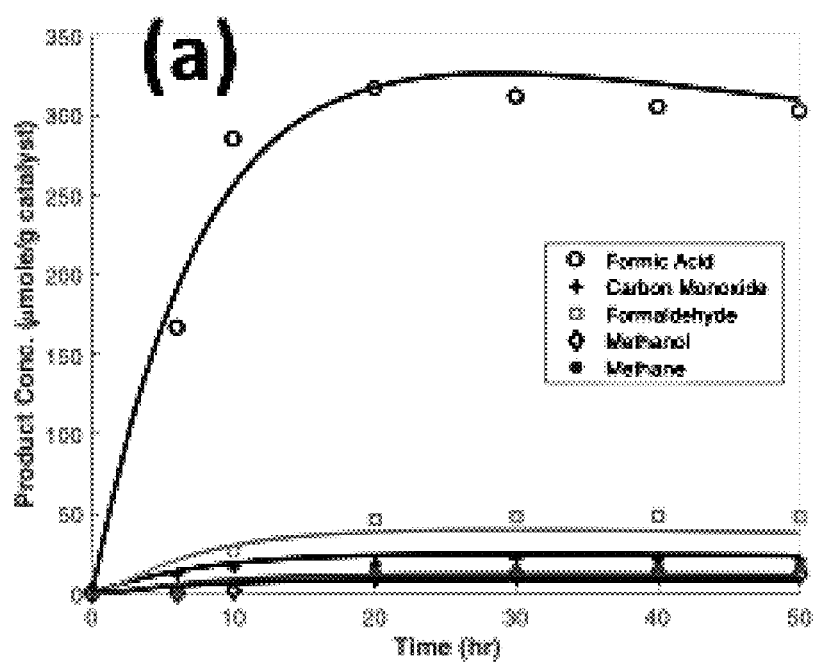
FIGS. 24A-24C depict kinetic experimental data and fitted model data for (FIG. 24A) RXN1: photocatalytic reduction of $CO_2$ to formaldehyde (experimental data obtained from Liu et al), (FIG. 24B) RXN2: Conversion of formaldehyde to trioxane (experimental data obtained from Yin et al), and (FIG. 24C) RXN3: Trioxane polymerization to polyoxymethylene (POM) (experimental data obtained from Shieh et al).

The experimental data provided by Liu et al. was used in this section (FIG. 24A). In the majority of the existing experimental literature, methanol and methane are mentioned as the main products of this photocatalytic process over $TiO_2$, the benchmark photocatalyst for this process. Less kinetic data is available for formates as products and/or intermediates, mainly because of the focused interest in methanol and methane as fuels and precursors for other chemical processes. Also, the difficulty of distinctive measurement of formates using common techniques such UV-vis spectroscopy is another reason to overlook the data for these products. The dataset chosen for the calculations has the advantage of reporting kinetic data for most prominent intermediate and products of the $CO_2$ reduction including formic acid, formaldehyde, carbon monoxide, methanol and methane. Additionally, the higher yield of formates reported in this dataset makes it of particular interest for the proposed overall pathway toward POM.

Photocatalytic reduction of $CO_2$ consists of a series of deoxygenation and hydrogenation reactions occurring through multiple electron and proton transfer steps. The concurrent photocatalytic water splitting reaction provide the hydrogens required for the reduction reactions and the photocatalyst provides the required electrons. Catalyst structure and morphology (type and availability of active sites, mode of adsorption of reactants on the surface, size and position of the semiconductor bandgap) and reaction condition (light source, temperature, pH, feed composition, presence of hole scavengers) determine the reaction mechanism. Reactions proceeds through different, sometimes competing, pathways and yield various products with different selectivity including formic acid, formaldehyde, carbon monoxide, methanol and methane, etc.

Many pathways have been proposed due to the wide range of experimentally observed intermediates and products. Among those, formaldehyde pathway or fast hydrogenation pathway follows $CO_2 \rightarrow HCOOH \rightarrow HCHO \rightarrow CH_3OH \rightarrow CH_4$. While this pathway is thermodynamically feasible, the kinetic models based on this mechanism are less explored as usually they cannot explain the concentration profiles of methanol as an intermediate toward methane. The alternative carbene pathway which proceeds as $CO_2 \rightarrow CO \rightarrow C^\bullet \rightarrow CH_3^\bullet \rightarrow CH_3OH/CH_4$ better explains the concentration profiles of methanol and methane, but cannot justify the presence of observed formates in the intermediate/product spectrum. It is plausible that different reactions pathways can occur in a system, however, some of them become more dominant in specific reaction condition and in presence of specific catalyst structures.

The experimental system under investigation by Liu et al. was saturated with 1 atm $CO_2$ in presence of 25 g of $TiO_2$ nanoparticles in 100 ml water. Sodium hydroxide (0.15 was added to act as hole scavenger and promote catalyst activity. A mercury UV lamp was used as the source of light and the reaction was carried at room temperature. The system was stirred during the reaction and the concentration of products were measured over 50 hours of reaction with 10 hours intervals. The chemical pathway and reaction rate constants were fit to the experimental data assuming a system limited by the surface reactions: ignoring any limitations in mass transfer, electron transfer, and adsorption/desorption of reagents, intermediates, and products. Since $CO_2$ and hydrogen evolution (water oxidation reaction) data was not reported in this study, a surface Langmuir-Hinshelwood model was not used and instead used bulk product concentration in the first order rate expressions to avoid overfitting the data and over parameterizing the kinetic model. Also, abundant proton was assumed to be provided in the system through the water oxidation reaction such that its concentration can be considered constant. lastly, the concentration of $CO_2$ in the liquid phase was calculated using Henry's law.

Fitting of various kinetic models to the experimental data and parameter estimation was performed in a single step using multi-objective optimization. The details of the objective function optimization are available in the supplementary information. Individual reaction rates were expressed as functions of the chemical concentrations and expressions for overtime concentration change of reactant and products were defined. Parameters were constrained in a range of $10^{-10}$ to 1 (1/s) and fitting was performed by simultaneous calculation and minimization of the following objective function using the ordinary least square (OLS) difference between the values of the experimental concentration of each products $(C_{exp})_i$ and the modeled one $(C_{model})_i$. The optimization algorithm was coded in MATLAB.

Among several reaction networks fitted to the data, including the formaldehyde and carbene pathways, the following reaction network (R1-R6)

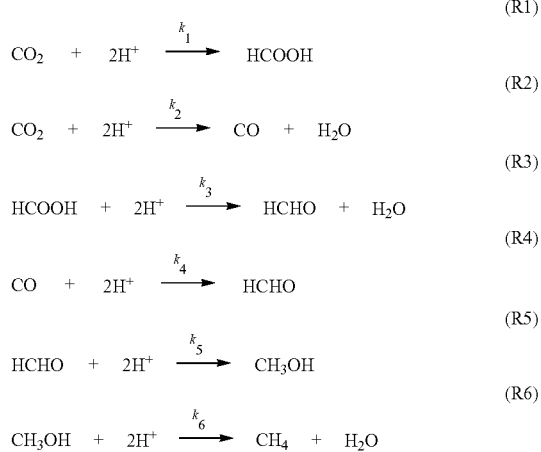

with concentration expressions including first-order reactions (eq1-eq7) fitted the data best (FIG. 24A).

$$d[CO_2]/dt=-k_1[CO_2]-k_2[CO_2] \quad (\text{eq. 1})$$

$$d[HCOOH]/dt=k_1[CO_2]-k_3[HCOOH] \quad (\text{eq. 2})$$

$$d[CO]/dt=k_2[CO_2]-k_4[CO] \quad (\text{eq. 3})$$

$$d[HCHO]/dt=k_3[HCOOH]+k_4[CO]-k_5[HCHO] \quad (\text{eq. 4})$$

$$d[CH_3OH]/dt=k_5[HCHO]-k_6[CH_3OH] \quad (\text{eq. 5})$$

$$d[CH_4]/dt=k_6[CH_3OH] \quad (\text{eq. 6})$$

This pathway contains a series of irreversible reactions in which two electron and protons are transferred to the reactant at each step. The two-electron transfer steps have been extensively studied in the theoretical studies of $CO_2$ reduction and it has been shown that they have lower energy barriers than single-electron transfer steps. The competing pathways from $CO_2$ to formaldehyde and CO lead to the formation of formaldehyde as an intermediate toward methanol, which is subsequently reduced to methane. Such reaction pathway has not been proposed in the literature and definitely not fitted against experimental kinetic data, however, Ji et al. have predicted that a pathway from $CO_2$ to formic acid and CO and from these product to formaldehyde has a lower energy barrier compared to well-established formaldehyde and carbene pathways. This new proposed mechanism can accurately fit the high formic acid and formaldehyde concentrations in this dataset while explaining the low methanol and methane concentrations. Neither of carbene and formaldehyde pathways and their combinations with and without reversible reactions at different steps can fit the data properly. However, one must remember that $CO_2$ photocatalytic reduction is a complicated process that depends on many aspects of the reaction condition and catalyst surface and this mechanism may be the dominant mechanism only in the specific experimental conditions that this data was collected at.

The estimated rate constants and their confidence intervals are shown in Table 2. The initial reduction of $CO_2$ to either formic acid or carbon monoxide is the rate-limiting step in the presented reaction pathway. The rate constants for the reductions of formic acid and CO to formaldehyde are three orders of magnitude larger. It is emphasized that the reduction of formaldehyde is comparably fast; as such, formaldehyde is expected to be a stable intermediate in the process, which may explain the lesser number of articles reporting observation of this chemical as a product.

RXN2: Formaldehyde Conversion to Trioxane.

Trioxane is industrially produced by acidic catalytic distillation of aqueous formaldehyde solution. This well-established chemical process suffers from high energy and low yield, with selectivity towards byproducts such as methyl formate and methyl glycols. In literature, the reaction is most often performed in batch at higher temperatures and the kinetic data are fitted to the overall reaction of $3HCHO \rightarrow C_3H_6O_3$. In reality, the reaction network involves hydration, oligomerization, and cyclization reactions of formaldehyde and other intermediates-requiring a more comprehensive reaction mechanisms to produce an accurate kinetic model.

Figure 24B:
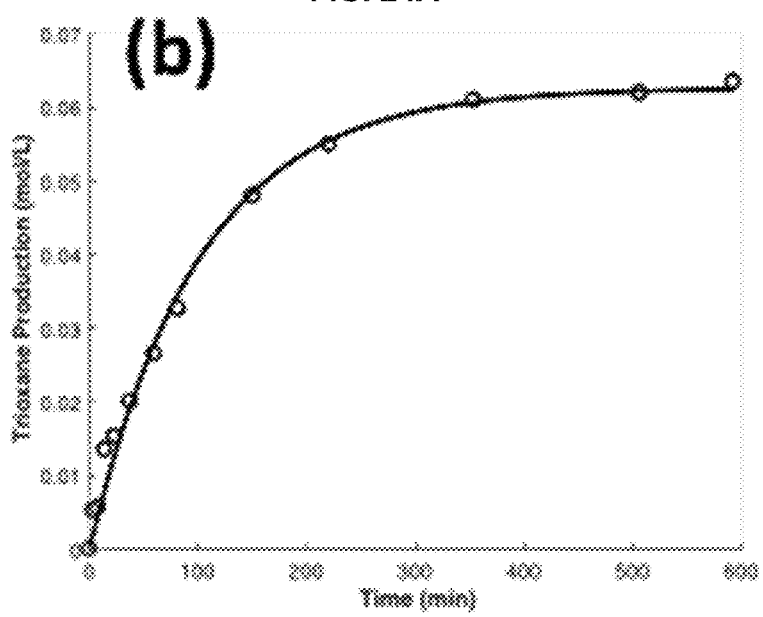

In the overall pathway from $CO_2$ to POM, trioxane must be produced at room temperature to avoid excessive energy input. The kinetic data available for trioxane reaction at 100° C. to find the relevant parameters at room temperature was used. The experimental data of trioxane formation reported by Yin et al. is presented in FIG. 24B. To capture the complicated pathway to trioxane formation and obtain more accurate rate constants at room temperature the following reaction pathway were used, consisting of hydration of formaldehyde (R7), dimerization (R8) and trimerization (R9) of formaldehyde, and finally a cyclization reaction (R10) to produce trioxane from the linear trimer:

$$HCHO + H_2O \rightleftharpoons HO(CH_2O)H \tag{R7}$$

$$2HO(CH_2O)H \rightleftharpoons HO(CH_2O)_2H \tag{R8}$$

$$HO(CH_2)H + HO(CH_2O)_2H \rightleftharpoons HO(CH_2O)_3H \tag{R9}$$

$$HO(CH_2O)_3H \rightleftharpoons (CH_2O)_3 + H_2O \tag{R10}$$

The following concentration expression based on elementary reactions were used to describe the concentration profiles of the reactant, intermediates, and product and the water concentration was assumed to be constant.

$$d[F]/dt = -k_7[F] + k_{r7}[HF] \tag{eq. 7}$$

$$d[HF]/dt = -k_8[HF]^2 + k_{r8}[D] - k_9[HF][D] + k_{r9}[T] \tag{eq. 8}$$

$$d[D]/dt = k_8[HF]^2 - k_{r8}[D] - k_9[HF][D] + k_{r9}[T] \tag{eq. 9}$$

$$d[T]/dt = k_9[HF][D] - k_{r9}[T] - k_{10}[T] + k_{r10}[Trioxane] \tag{eq. 10}$$

$$d[Trioxane]/dt = k_{10}[T] - k_{r10}[Trioxane] \tag{eq. 11}$$

The values of the rate constants at 25 C were calculated/estimated and are listed in Table 2. The reversible rate constants of reaction 7-9 were obtained from Ott et al. and Winkleman et al. at 360-371.15 C, the forward reaction rate constants were calculated using the equilibrium constants reported by Kuhnert et al. at 360-371K, and the rate constants for the reversible cyclization reaction were fitted to the experimental data of trioxane by Yin et al. at the same temperature Knowing the rate constants of the cyclization reaction at 371, the energy barrier estimated by Kua et al. using Density Functional theory calculations was used to obtain the rate constants at the room temperature. The rate constants for hydration and oligomerization reaction at room temperature were calculated using the same methodology.

The rate-limiting step in conversion of formaldehyde to trioxane is the cyclization reaction, having a rate constant that is 4-5 orders of magnitude smaller than the hydration and oligomerization reactions. While the polyglycol oligomers were experimentally observed at lower temperatures, formation of the trioxane only at higher temperatures confirms the cyclization reaction as the main bottleneck in formation of trioxane. At room temperature, the cyclization reaction (R10) imposes an kinetics as slow as that of $CO_2$ conversion to formic acid and CO and can equally affect the kinetics of the overall pathway toward POM production.

RXN3: Trioxane Polymerization.

POM is mainly produced through cationic polymerization of trioxane in presence of an initiator or copolymerization with co-monomer. While bulk polymerization occurs faster, the solution polymerization has been used more often to study the kinetics of process. Solution polymerization proceeds through multiple steps of initiation, chain growth, side polymerizations, termination, and chain transfer. Most studied system is the cationic polymerization in presence of acidic boron trifluoride ($BF_3$). In this polymerization process, the induction phase occurs fast, leaving the chain growth phase as the rate-limiting step. The induction period has been extensively studied in the literature with several reaction mechanisms proposed for this period. Conversely, few kinetic data sets and proposed reaction mechanisms exist for the rapid growth phase, as this phase is accompanied with phase separation and crystallization of insoluble long polymer chains. Therefore, it has been more convenient to report the total trioxane conversion and not production of the final polymer and its relevant details.

Figure 24C:
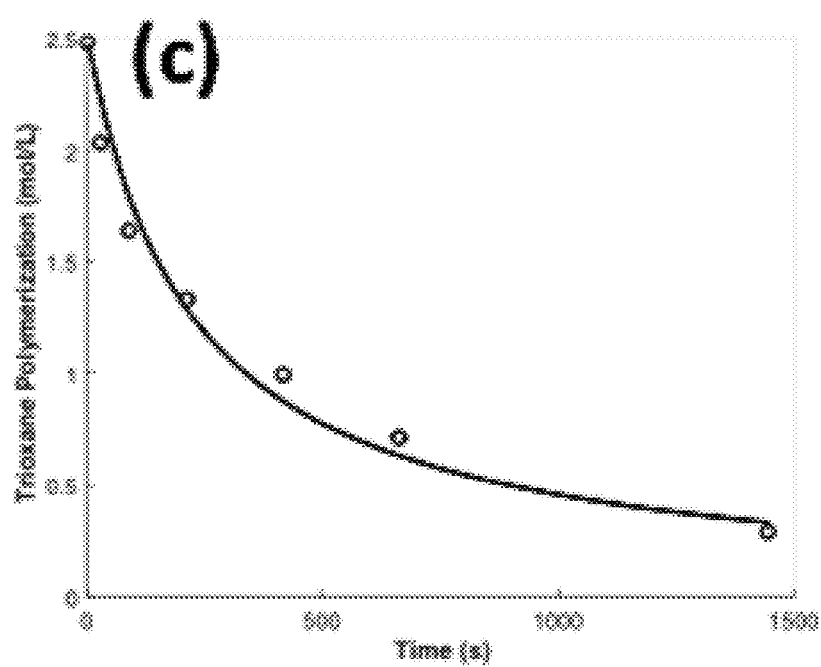

The chain growth phase of the reaction into consideration for the overall $CO_2$ to POM pathway was taken, as this phase dictates the rate of production of the final polymer. The trioxane conversion data reported by Shieh et al. (FIG. 24C) was used to fit the overall cationic chain growth reaction (R11):

$$(CH_2O)_3 \xrightarrow{k_{11}} (CH_2O)_n \tag{R11}$$

with the rate expression of:

$$d[Trioxane]/dt = -k_{11}[I][Trioxane]^2 \tag{eq. 12}$$

Shieh et al. carried the experiments for this kinetic dataset at 30 C using $BF_3$ as initiator in an organic solvent. They proposed a kinetic model that emphasizes on the crystallization and depolymerization steps and their rate constants depended on the initial monomer concentration. On the other hand, the proposed rate expression reflects the kinetics of chain propagation phase in a cationic polymerization process and counts for the initiator effect and monomer concentration. Total polymer production, regardless of the consecutive crystallization process, is the output of the model and moreover, the rate constant remains independent of the monomer concentration.

The trioxane polymerization follows a second-order reaction with respect to the monomer and a first order reaction with respect to initiator concentration. Commonly in the literature, the initiator initial concentration is about 2-3 orders of magnitude lower than trioxane concentration to assure the formation of longer chains in this chain-growth polymerization process. While the rate constant of this reaction at 30 C (Table 2) is generally a few orders of magnitudes larger than the trioxane cyclization reaction (R10), this reaction proceeds slowly at lower trioxane concentrations due to the dependence on the square of the trioxane concentration and low quantity of initiator. Therefore, depending on the trioxane initial concentration either of the trioxane formation (R10) or polymerization (R11) can be the main rate-limiting step for conversion of formaldehyde to POM.

Overall Compartmental Reaction from $CO_2$ to POM.

Figure 25:
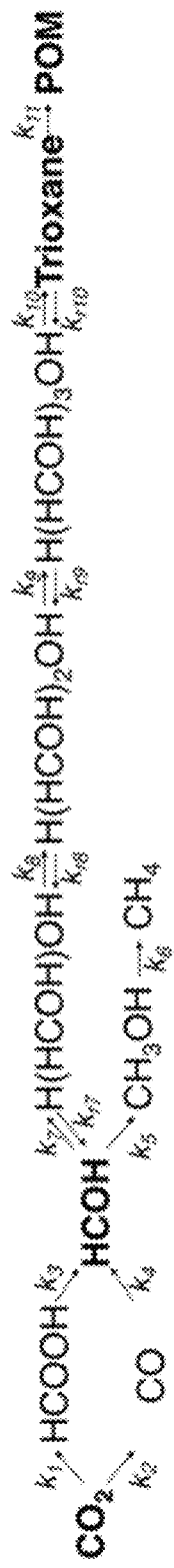
FIG. 25 depicts the proposed overall reaction network from $CO_2$ to: kinetic engineering is required to overcome two main bottlenecks in the process: (i) enhancing photocatalytic activity to improve the slow $CO_2$ reduction reaction (RXN1, the green section of the network), and (ii) engineering trioxane formation and polymerization to dominate the competing pathway toward methanol and methane (RXN2 and RXN3, blue section of the network).

The overall reaction pathway from $CO_2$ to POM includes reaction R1-R11 as shown in FIG. 25. This reaction mechanism assumes the simultaneous production and consumption of formaldehyde and trioxane as intermediates toward POM in the overall pathway. The rate constants indicated in Table 2 in FIG. 25 were used to evaluate the rate of production of POM under continuous supply of $CO_2$ over time. To capture the polymer production from trioxane conversion, any byproduct formation is neglected, and the final polymer is taken to be a chain of 500 repeat units, equivalent to a molecular weight ($M_w$) of ~45,000 g/mol (averaged over the literature data for POM molecular weight obtained at various synthesis conditions. Any discussion or incorporation of a molecular weight distribution of the products is beyond the scope of this work.

Such a kinetic model can be extremely limited by two main bottlenecks: first, the formaldehyde consumption in competing pathway toward methanol production instead of trioxane production and polymerization to POM production. Kinetic engineering is required to prevent the pathway from formaldehyde to methanol and instead favor the formaldehyde conversion to trioxane. Engineering the reaction media through pH adjustment at lower acidic values (favoring the pathway toward trioxane), minimizing hole scavenger concentration such that less electron-hole pairs are available for the methanol pathway are examples of such kinetic engineering strategies. More importantly, aqueous formaldehyde solutions usually exist in equilibrium with methanol in bulk; thus, the addition of minimal amount of methanol at the beginning of reaction encourages the reversible methanol to formaldehyde reaction. The dependence of the trioxane polymerization on the second power of the trioxane concentration can also slow down the polymerization process. In cationic polymerization of trioxane such kinetic dependence is inevitable, however, other polymerization routes can be explored to overcome this barrier in the overall scheme of the reaction. Second major bottleneck in the overall system is imposed by the slow $CO_2$ photocatalytic reduction and formaldehyde formation. Engineering catalytic surfaces with enhanced photocatalytic activity and selectivity for formaldehyde pathway is another important factor in achieving the proposed overall pathway toward POM.

Maximization of POM Growth Rate Via Kinetic Engineering and $CO_2$ Adsorption.

Figure 26A:
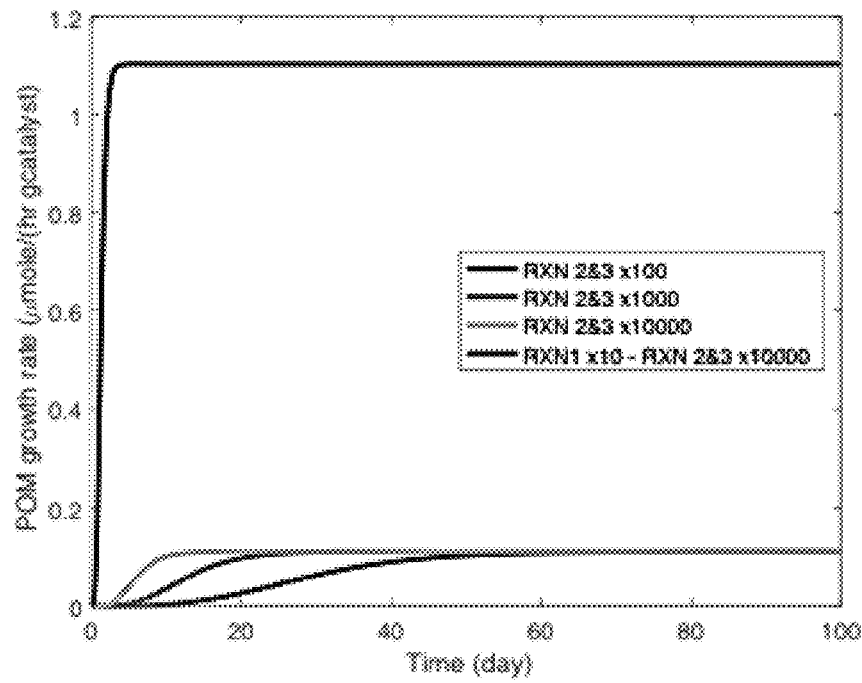
FIG. 26A depicts the effect of relative improvement in kinetics of RXN 1 (photocatalytic unit) and RXN 2&3 (formaldehyde polymerization unit) on POM growth rate over time under atmospheric $CO_2$ pressure. At any given $CO_2$ concentration, engineering of formaldehyde polymerization reaction units accelerates overall kinetics until it reaches the POM steady state growth rate. Above this point, the overall process can be improved only by enhancing the photocatalytic activity in RXN 1.

The effects of kinetic enhancement of each reaction unit on the overall growth rate of POM is shown in FIG. 26A. At atmospheric $CO_2$ pressure, engineering RXN2 and RXN3 units such that it overcomes the methanol production pathway accelerates the overall kinetic of the process until it reaches the steady state. After this point, the overall process can only be improved by improving the kinetics of RXN1 by engineering the photocatalyst for enhanced $CO_2$ reduction activity. Therefore, RXN2 and 3 mainly constrain the time to reach steady state growth rate and photocatalytic activity determines the upper limit of the POM growth rate at any given $CO_2$ pressure.

Figure 26B:
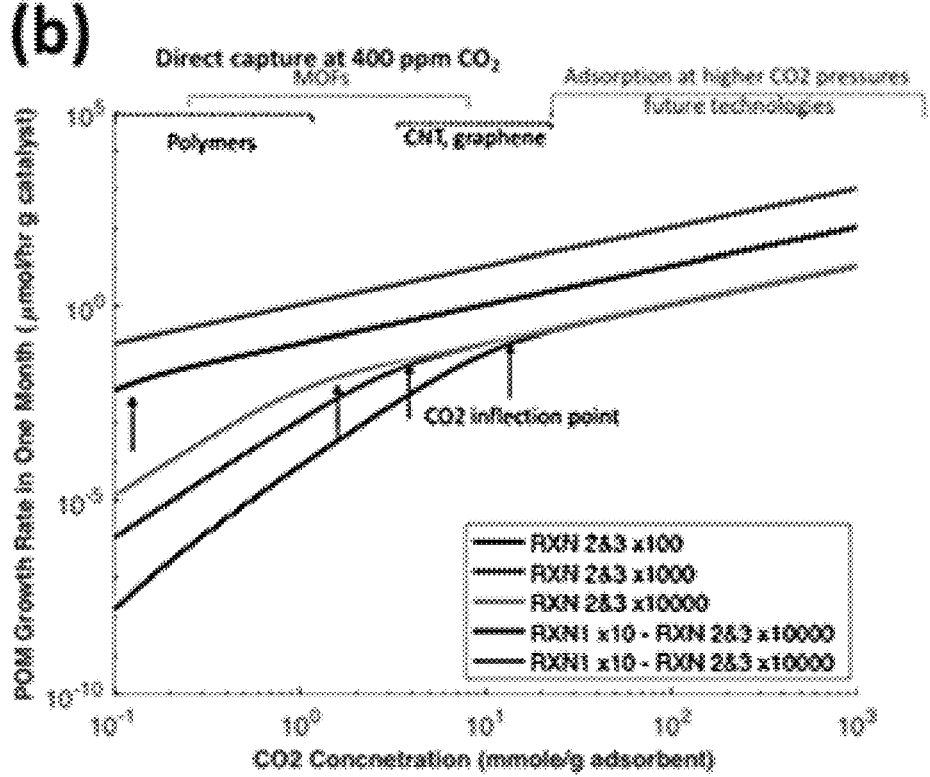
FIG. 26B depicts the effect of relative improvement in kinetics of reaction network at various $CO_2$ adsorption capacities: $CO_2$ inflection concentration separates two regimes: (i) below $CO_{2\_inf}$ formaldehyde polymerization is rate-limiting step and must be improved, (ii) above $CO_{2\_inf}$ POM growth rate linearly depends on the photocatalytic activity and $CO_2$ concentration at the photocatalyst surface.

So far, the POM growth rate has been calculated assuming the availability of atmospheric pressure at 400 ppm. However, it is feasible to increase the $CO_2$ concentration available at the photocatalyst surface by combining this compartmental catalytic unit with the $CO_2$ capture technologies. FIG. 26B indicates the POM growth rate achieved by the kinetic engineering of RXN1, 2, and 3 at higher $CO_2$ concentrations enabled by various capture mechanisms after one month of reaction. The CO2 inflection point in this graph separates two regimes: (i) below $CO_{2\_inf}$ where the trioxane formation and polymerization (RXN2 & 3) are the main-rate limiting steps and (ii) above $CO_{2\_inf}$ where the POM growth rate scales linearly with photocatalytic activity and $CO_2$ concentration. Hence, any hybrid catalytic/capture system designed for $CO_2$ to POM conversion can be evaluated using $CO_{2\_inf}$ as a metric; if effective concentration of $CO_2$ is below $CO_{2\_inf}$ the efforts must be focused on engineering the kinetic so the trioxane formation and polymerization and if it is above the $CO_{2\_inf}$ enhancing the capture capacity and photocatalytic activity is of higher priority.

Figure 27A:
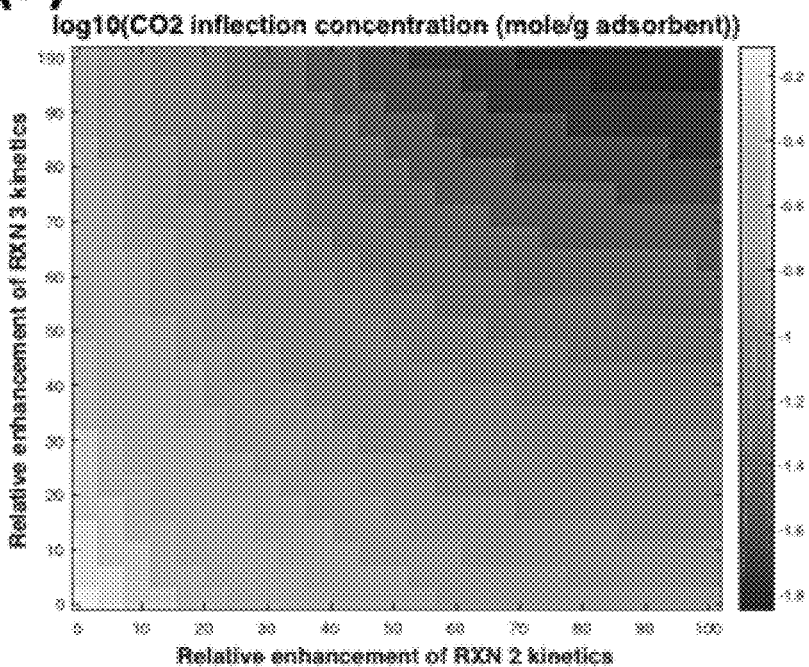
FIGS. 27A-27B depict the mapping of $CO_{2\_inf}$ with respect to the enhancement required for (FIG. 27A) RXN2 vs. RXN3 and (FIG. 27B) RXN1 vs. RXN2 & 3. Depending on the reaction condition, we can determine the specific focus of debottlenecking efforts, either polymerization engineering and photocatalytic improvement or CO2 capturing via adsorption.
Figure 27B:
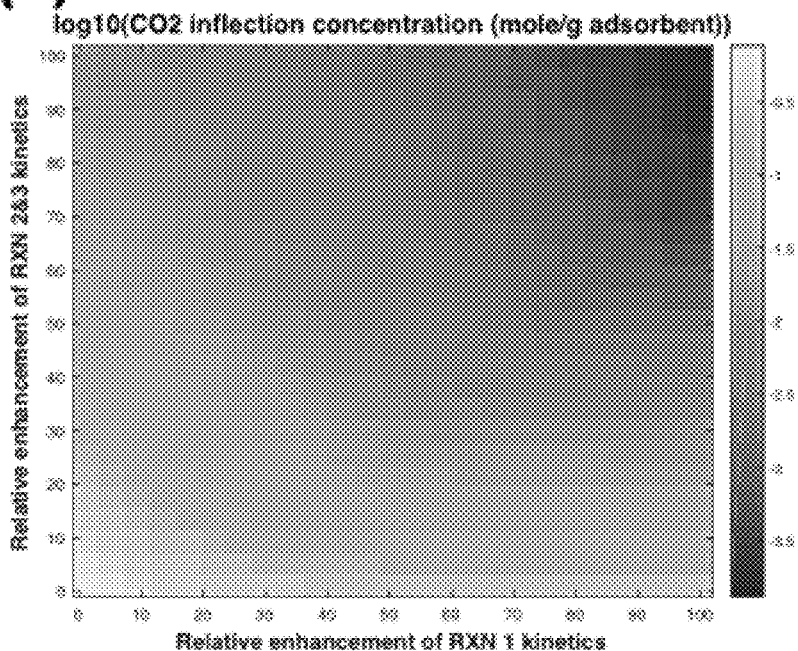

To obtain a better perception of the required reaction engineering required for each system, the $CO_{2\_inf}$ was mapped with respect to enhancements in polymerization (RXN3) and trioxane formation (RXN2) as well as photocatalytic activity (RXN1) and overall formaldehyde conversion to POM (RXN2 & 3) in FIG. 27. This map can be used a s guideline such that by knowing characteristics of the reaction system (e.g., $CO_2$ concentration, kinetics of polymerization, photocatalytic activity), other aspects of the system must be improved can be determined. Therefore, reaction engineering can be focused toward either debottlenecking the kinetics of a specific compartment or improving the $CO_2$ adsorption by in the catalytic unit.

Strategies for Enhancing the $CO_2$ Reduction to Monomers Via Coupling Photocatalyst with Solvent-Induced Electricity and/or Colloidal Batteries:

Traditional photocatalytic reduction of $CO_2$ with semiconductive materials utilizes solar energy as the sole energy source, but the slow reaction kinetics and lack of product selectivity withholds it from being an industrially viable solution for carbon fixation. Limited electron transfer from the semiconductor to the $CO_2$ is one of the main reasons for slow reaction rates and low product yield. A novel hybrid particulate photo-electro-catalytic platform can combine ambient solar energy harvesting with energy derived from a newly discovered solvent-nanomaterial electrical coupling or a colloidal battery that is dispersible in solvents. This platform consists of (1) a semiconducting photocatalysts and (2) a Janus carbon particle capable of electronic generation through a process termed Asymmetric Chemical Doping (ACD) and/or a micron-sized.

The pure photocatalytic transformation can be augmented using the solvent-derived electrical potential generated from ACD, establishing a hybrid process still untethered to external electrical inputs but potentially with much higher reactivity. Asymmetric Chemical Doping (ACD) utilizes a chemical potential gradient across a single-walled carbon nanotube network (SWNT), established via solvent molecular doping (e.g., $CH_3CN$ or $H_2O$), as means of electricity generation. In this process, the broken spatial symmetry in the Fermi levels of electrical carriers inside the SWNT network translates directly into a voltage potential. By coupling semiconductor photocatalyst with engineered SWNT particles capable of generating electron flow through the ACD process, the hindered and low-rate electron transfer to $CO_2$ can be overcome. With the photocatalyst-SWNT interface properly tuned, this hybrid system can create a high-rate electron transfer pathway to $CO_2$ molecules, thereby improving $CO_2$ reduction kinetics. Moreover, interfacing the photocatalysts with ACD-enabled SWNT particles creates additional active catalytic sites that allow us to alter or more precisely control the reaction pathways, and hence increase the selectivity of some products over the others.

Similarly, micron-sized colloidal batteries can be interfaced with the photocatalyst to facilitate the electron transfer to $CO_2$ and subsequent reduction reactions. The additional electrical potential prevents the electron-hole recombination and lowers the overpotential of the reduction reactions. To power these colloidal electronic state machines, "colloidal batteries", which are fabricated onto particles about 100 μm in size. The current version is based on metal-air battery, which is easy to fabricate and use, and has high energy density. An active metal serves as anode, while oxygen gas is the cathodic active material. The colloidal batteries can be fabricated with many different methods and have open circuit voltage around 1 V, short circuit current density about 0.5 $mA/cm^2$. These colloidal batteries can be dispersed in solution or potentially fixed in a hydrogel network.

Alternative Pathways from $CO_2$ to Other Carbon-Fixing Polymer Composites:

As mentioned earlier, the specific pathway from $CO_2$ to formaldehyde and to POM is a case study to obtain further insight toward the overall strategy of production of macromolecular products from atmospheric $CO_2$. Certainly, other chemical pathways may be proposed and their thermodynamic and kinetic feasibility can be investigated. Pathways from formic acid, formaldehyde and methanol toward ethylene, acrylic acid, and simple sugars are among the feasible overall compartmental catalytic systems that can serve as building blocks for high-energy polymeric materials.

Formaldehyde produced from the photocatalytic reduction of $CO_2$ can also serve as a building block of several resinous polymer materials. Under reaction with urea, formaldehyde will produce Urea formaldehyde (UF), also known as urea-methanal, a thermosetting polymer used in building materials such as particle and fiber board as well as in foam insulation. In addition, this polymeric material serves as a nitrogen source for slow-release fertilizers.

Another class of materials enabled through this production of formaldehyde are phenol formaldehyde resins (PF) or phenolic resins. Formaldehyde, upon reaction with phenolic compounds forms a resinous material. This finds use as a building material to produce laminates of fiberglass and paper as well as to increase the chemical and temperature resistance of plywood.

Additionally, formaldehyde can undergo an autocatalytic reaction known as the formose reaction to produce C5 and C6 sugar molecules-specifically glucose. Under basic conditions and in the presence of a divalent cation, these sugar molecules are formed. This presents a chemical pathway that mirrors natural photosynthesis, by creating formaldehyde through the photocatalytic reduction of atmospheric $CO_2$, and the subsequent production of sugar molecules from this formaldehyde, it would be possible to produce structural saccharides (such as amylose) as well as foodstuff (such as polydextrose) from ambient sources of carbon and sunlight.

The following references are incorporated by reference in their entirety.

[1] J. A. Syrett, C. R. Becer, D. M. Haddleton, *Polymer Chemistry* 2010, 1, 978.
[2] D. Y. Wu, S. Meure, D. Solomon, *Progress in Polymer Science* 2008, 33, 479.
[3] C. E. Diesendruck, N. R. Sottos, J. S. Moore, S. R. White, *Angewandte Chemie International Edition* 2015, 54, 10428.
[4] X. Chen, M. A. Dam, K. Ono, A. Mal, H. Shen, S. R. Nutt, K. Sheran, F. Wudl, *Science* 2002, 295, 1698.
[5] S. D. Bergman, F. Wudl, *Journal of Materials Chemistry* 2007, 18, 41.
[6] L. Li, B. Yan, J. Yang, L. Chen, H. Zeng, *Advanced Materials* 2015, 27, 1294.
[7] A. Phadke, C. Zhang, B. Arman, C.-C. Hsu, R. A. Mashelkar, A. K. Lele, M. J. Tauber, G. Arya, S. Varghese, *Proc. Natl. Acad. Sci. U.S.A.* 2012, 109, 4383.
[8] M. Nakahata, Y. Takashima, H. Yamaguchi, A. Harada, *Nat Commun* 2011, 2, 511.
[9] A. Harada, Y. Takashima, M. Nakahata, *Acc. Chem. Res.* 2014, 47, 2128.
[10] S. C. Grindy, R. Learsch, D. Mozhdehi, J. Cheng, D. G. Barrett, Z. Guan, P. B. Messersmith, N. Holten-Andersen, *Nature Materials* 2015, 14, 1210.
[11] S. Srivastava, M. Andreev, A. E. Levi, D. J. Goldfeld, J. Mao, W. T. Heller, V. M. Prabhu, J. J. de Pablo, M. V. Tirrell, *Nat Commun* 2017, 8, 14131.
[12] S. R. White, N. R. Sottos, P. H. Geubelle, J. S. Moore, *Nature* 2001, 409, 794.
[13] S. H. Cho, H. M. Andersson, S. R. White, N. R. Sottos, P. V. Braun, *Advanced Materials* 2006, 18, 997.
[14] K. S. Toohey, N. R. Sottos, J. A. Lewis, J. S. Moore, S. R. White, *Nature Materials* 2007, 6, 581.
[15] S. Gupta, S. D. Pang, H. W. Kua, *Construction and Building Materials* 2017, 146, 419.
[16] S. E. Weise, A. P. M. Weber, T. D. Sharkey, *Planta* 2004, 218, 474.
[17] K. Kobayashi, H. Sumitomo, Y. Ina, *Polymer Journal* 1983, 15, 667.
[18] R. P. Wool, *Soft Matter* 2008, 4, 400.
[19] J. S. Dordick, R. J. Linhardt, D. G. Rethwisch, *Chemtech* 1994, 24, 33.
[20] Q. Wang, J. S. Dordick, R. J Linhardt, *Chem. Mater.* 2002, 14, 3232.
[21] T. Yamada, H. Arakawa, T. Okajima, T. Shimada, A. Ikai, *Ultramicroscopy* 2002, 91, 261.
[22] H. Zhang, D. Zhai, Y. He, *RSC Adv.* 2014, 4, 44600.
[23] H.-P. Cong, P. Wang, S.-H. Yu, *Chem. Mater.* 2013, 25, 3357.
[24] M. A. Rafiee, J. Rafiee, Z. Wang, H. Song, Z. -Z. Yu, N. Koratkar, *ACS Nano* 2009, 3, 3884.
[25] S. Alwarappan, C. Liu, A. Kumar, C. -Z. Li, *The Journal of Physical Chemistry C* 2010, 114, 12920.
[26] G. Ritte, K. Raschke, *New Phytologist* 2003, 159, 195.
[27] D. A. Walker, *Photosynth Res* 2003, 76, 319.
[28] D. Joly, R. Carpentier, *Methods Mol. Biol.* 2011, 684, 321.
[29] S. P. Robinson, D. A. Walker, *FEBS Lett.* 1979, 107, 295.
[30] G. Schafer, U. Heber, *Plant Physiology* 1977, 60, 286.
[31] D. G. Peavey, M. Steup, M. Gibbs, *Plant Physiology* 1977, 60, 305.
[32] M. Stitt, H. W. Heldt, *Plant Physiology* 1981, 68, 755.
[33] H. E. Neuhaus, N. Schulte, *Biochemical Journal* 1996, 318 (Pt 3), 945.
[34] N. J. Kruger, T. A. Rees, *Planta* 1983, 158, 179.
[35] J. C. Servaites, D. R. Geiger, *J Exp Bot* 2002, 53, 1581.
[36] U. Heber, J. Viil, S. Neimanis, T. Mimura, K. J. dietz, *zeitschrift fur naturforschung C-A journal of biosciences* 1989, 44c, 524.
[37] I. M. Rao, N. Terry, *Plant Physiology* 1989, 90, 814.
[38] R. K. Monson, M. E. Rumpho, G. E. Edwards, *Planta* 1983, 159, 97.
[39] W. Cockburn, C. W. Baldry, D. A. Walker, *Biochimica et Biophysica Acta (BBA)-Bioenergetics* 1967, 131, 594.
[40] U. I. Flugge, M. Freisl, H. W. Heldt, *Plant Physiology* 1980, 65, 574.
[41] P. E. Giebel, *Extraction of Chloroplasts from Plant Tissue and Their Use in Demonstrating the Hill reaction*, Dept. of Biol. Virginia Commonwealth Univ., Richmond, Va., 2006. 31-47.
[42] J. C. Rooke, C. Meunier, A. Léonard, B.-L. Su, *Pure and Applied Chemistry* 2008, 80, 1249.
[43] A. A. Boghossian, F. Sen, B. M. Gibbons, S. Sen, S. M. Faltermeier, J. P. Giraldo, C. T. Zhang, J. Zhang, D. A. Heller, M. S. Strano, *Advanced Energy Materials* 2013, 3, 881.
[44] J. P. Giraldo, M. P. Landry, S. M. Faltermeier, T. P. McNicholas, N. M. Iverson, A. A. Boghossian, N. F. Reuel, A. J. Hilmer, F. Sen, J. A. Brew, M. S. Strano, *Nature Materials* 2014, 13, 400.
[45] Y. Nakano, K. Asada, *Plant Cell Physiol* 1980, 21, 1295.
[46] P. W. Barone, S. Baik, D. A. Heller, M. S. Strano, *Nature Materials* 2005, 4, 86.
[47] A. Elgawish, M. Glomb, M. Friedlander, V. M. Monnier, *J Biol. Chem.* 1996, 271, 12964.
[48] J. H. Baxendale, M. G. Evans, C. S. Park, *Trans. Faraday Soc.* 1946, 42, 155.

[49] U. S. Nandi, S. R. Palit, *Journal of Polymer Science Part A: Polymer Chemistry* 1955, 17, 65.
[50] R. K. Trench, J. E. Boyle, D. C. Smith, *Proceedings of the Royal Society B: Biological Sciences* 1973, 184, 51.
[51] B. J. Green, W.-Y. Li, J. R. Manhart, T. C. Fox, E. J. Summer, R. A. Kennedy, S. K. Pierce, M. E. Rumpho, *Plant Physiology* 2000, 124, 331.
[52] S. Igarashi, T. Ohtera, H. Yoshida, A. B. Witarto, K. Sode, *Biochemical and Biophysical Research Communications* 1999, 264, 820.
[53] L. Brunsveld, B. Folmer, E. W. Meijer, R. P. Sijbesma, *Chem. Rev.* 2001, 101, 4071.
[54] H. Kashiwagi, S. Enomoto, *Chem. Pharm. Bull.* 1981, 29, 913.
[55] H. Ueda, Z. Kuri, S. Shida, *Nippon kagaku zassi* 1961, 82, 8.
[56] M.-X. Fu, K. J. Wells-Knecht, J. A. Blackledge, T. J. Lyons, S. R. Thorpe, J. W. Baynes, *Diabetes* 1994, 43, 676.
[57] S. P. Robinson, *Photosynth Res* 1983, 4, 281.
[58] R. M. Lilley, M. P. Fitzgerald, K. G. Rienits, D. A. Walker, *New Phytologist* 1975, 75, 1.
[59] D. I. Amrnon, *Plant Physiology* 1949, 24, 1.
[60] B. E. Michel, M. R. Kaufmann, *Plant Physiology* 1973, 51, 914.
[61] R. J. Bondar, D. C. Mead, *Clinical Chemistry* 1974, 20, 586.
[62] R. Geiger, H. Fritz, *Methods of Enzymatic Analysis*, Edited by Bergmeyer, 1984.
[63] D. Southgate, *Measurement of Unavailable Carbohidrates. Structural and Non-Structural Polysaccharides, in. "Determination of Food Carbohydrate" Dat Southgate, Ed,* 1976.
[64] H. W. Heldt, C. J. Chon, D. Maronde, A. Herold, Z. S. Stankovic, D. A. Walker, M. Kraminer, M. R. Kirk, U. Heber, *Plant Physiology* 1977, 59, 1146.
[65] A. Asati, S. Santra, C. Kaittanis, J. M. Perez, *ACS Nano* 2010, 4, 5321.
[66] N. Nagasawa, T. Yagi, T. Kume, F. Yoshii, *Carbohydrate Polymers* 2004, 58, 109.
[67] Y. Pocker, E. Green, *Journal of the American Chemical Society* 1974, 96, 166.
[68] M. Galluzzi, C. S. Biswas, Y. Wu, Q. Wang, B. Du, F. J. Stadler, *NPG Asia Materials* 2016, 8, e327.
[69] V. B. Koman, N. R. von Moos, C. Santschi, V. I. Slaveykova, O. J. F. Martin, *Nanotoxicology* 2016, 10, 1041.
[70] V. B. Koman, C. Santschi, O. J. F. Martin, *Biomedical Optics Express* 2015, 6, 2353.
[71] White, J. L. et al. Light-Driven Heterogeneous Reduction of Carbon Dioxide: Photocatalysts and Photoelectrodes. *Chem. Rev.* 115, 12888-12935 (2015).
[72] Habisreutinger, S. N., Schmidt-Mende, L. & Stolarczyk, J. K. Photocatalytic reduction of $CO_2$ on $TiO_2$ and other semiconductors. *Angewandte Chemie International Edition* 52, 7372-7408 (2013).
[73] Bartholomé, E., Köhler, W., Schecker, H. G. & Schulz, G. Reaktionstechnische und kinetische Untersuchungen zur Trioxan-Synthese. *Chemie Ingenieur Technik* 43, 597-601 (2004).
[74] Koči, K., Obalová, L. & Šolcová, O. Kinetic study of photocatalytic reduction of $CO_2$ over $TiO_2$. (2010).
[75] Tahir, M. & Amin, N. S. Photocatalytic $CO_2$ reduction and kinetic study over In/$TiO_2$ nanoparticles supported microchannel monolith photoreactor. *Applied Catalysis A: General* 467, 483-496 (2013).
[76] Peng, Y.-P., Yeh, Y.-T., Shah, S. I. & Huang, C. P. Concurrent photoelectrochemical reduction of $CO_2$ and oxidation of methyl orange using nitrogen-doped $TiO_2$. *Applied Catalysis B: Environmental* 123-124, 414-423 (2012).
[77] Chandrashekara, M. N., Desai, D. & Chanda, M. Kinetics of solution polymerisation of trioxane-I. Polymerisation during induction period. *European Polymer Journal* 21, 833-840 (1985).
[78] Tahir, M. & Amin, N. S. Photocatalytic $CO_2$ reduction and kinetic study over In/$TiO_2$ nanoparticles supported microchannel monolith photoreactor. *Applied Catalysis A: General* 467, 483-496 (2013).
[79] Morgan, J. A. & Rhodes, D. Mathematical Modeling of Plant Metabolic Pathways. *Metabolic Engineering* 4, 80-89 (2002).

Details of one or more embodiments are set forth in the accompanying drawings and description. Other features, objects, and advantages will be apparent from the description, drawings, and claims. Although a number of embodiments of the invention have been described, it will be understood that various modifications may be made without departing from the spirit and scope of the invention. It should also be understood that the appended drawings are not necessarily to scale, presenting a somewhat simplified representation of various features and basic principles of the invention.

What is claimed is:

1. A method of self-healing a polymer matrix comprising:
exposing a polymer matrix including a catalyst to carbon dioxide and an energy source; and
generating additional material to the polymer matrix from the carbon dioxide.

2. The method of claim 1, wherein the catalyst includes a chloroplast, a nanocatalyst, or a colloidal battery.

3. The method of claim 1, wherein the polymer matrix includes a chloroplast in a hydrogel.

4. The method of claim 3, wherein the polymer matrix further comprises a nanoparticle.

5. The method of claim 4, wherein the nanoparticle includes ceria.

6. The method of claim 3, wherein the polymer matrix further comprises a glucosidase, a glucose dehydrogenase or a hexokinase.

7. The method of claim 3, wherein the polymer matrix further comprises a graphene oxide.

8. The method of claim 3, wherein the polymer matrix further comprises an acrylamide.

9. The method of claim 1, wherein the energy source includes light energy, chemical energy or electrical energy.

* * * * *